US010952686B2

(12) United States Patent
Gunderson et al.

(10) Patent No.: US 10,952,686 B2
(45) Date of Patent: Mar. 23, 2021

(54) MOBILE APPLICATION TO PROMPT PHYSICAL ACTION TO MEASURE PHYSIOLOGIC RESPONSE IN IMPLANTABLE DEVICE

(71) Applicant: Medtronic, Inc., Minneapolis, MN (US)

(72) Inventors: Bruce D. Gunderson, Plymouth, MN (US); Eduardo N. Warman, Maple Grove, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 13 days.

(21) Appl. No.: 15/607,945

(22) Filed: May 30, 2017

(65) Prior Publication Data
US 2018/0035956 A1 Feb. 8, 2018

Related U.S. Application Data

(60) Provisional application No. 62/370,146, filed on Aug. 2, 2016.

(51) Int. Cl.
*A61B 5/00* (2006.01)
*A61B 5/0205* (2006.01)
(Continued)

(52) U.S. Cl.
CPC ............ *A61B 5/747* (2013.01); *A61B 5/0031* (2013.01); *A61B 5/0205* (2013.01);
(Continued)

(58) Field of Classification Search
CPC ..... A61B 5/747; A61B 5/0031; A61B 5/0205; A61B 5/0215; A61B 5/0422;
(Continued)

(56) References Cited

U.S. PATENT DOCUMENTS 2,009,393 A 7/1935 Gioacchino
4,374,382 A 2/1983 Markowitz
(Continued)

FOREIGN PATENT DOCUMENTS

CN 1031481 A 3/1989
CN 2621634 Y 6/2004
(Continued)

OTHER PUBLICATIONS

Giuberti et al., "Automatic UPDRS Evaluation in the Sit-to-Stand Task of Parkinsonians: Kinetic Analysis and Comparative Outlook on the Leg Agility Task", IEEE Journal of Biomedical and Health Informatics, May 2015, pp. 2168-2194, vol. 19, No. 3.
(Continued)

*Primary Examiner* — Mallika D Fairchild
*Assistant Examiner* — Minh Duc G Pham
(74) *Attorney, Agent, or Firm* — Shumaker & Sieffert, P.A.

(57) ABSTRACT

A user equipment that includes a touchscreen, and at least one processor configured to generate first timestamp data based upon detection of a first touch event on the touchscreen, and second timestamp data based upon detection of a second touch event on the touchscreen, for calculation by a medical device system of a patient-specific functional status parameter associated with a Sit-To-Stand performance test over a time segment inclusively bounded by a first time defined by the first timestamp data and a second time defined by the second timestamp data.

20 Claims, 36 Drawing Sheets

(51) Int. Cl.
| | | |
|---|---|---|
| *A61N 1/08* | (2006.01) | |
| *A61N 1/372* | (2006.01) | |
| *G06F 19/00* | (2018.01) | |
| *G08B 1/08* | (2006.01) | |
| *A61B 5/042* | (2006.01) | |
| *A61B 5/11* | (2006.01) | |
| *A61B 5/0215* | (2006.01) | |
| *A61B 5/0538* | (2021.01) | |
| *G06Q 50/24* | (2012.01) | |
| *A61B 5/08* | (2006.01) | |
| *A61N 1/36* | (2006.01) | |

(52) U.S. Cl.
CPC .......... *A61B 5/0215* (2013.01); *A61B 5/0422* (2013.01); *A61B 5/0538* (2013.01); *A61B 5/1116* (2013.01); *A61B 5/686* (2013.01); *A61B 5/6882* (2013.01); *A61N 1/08* (2013.01); *A61N 1/37282* (2013.01); *G06F 19/3418* (2013.01); *G06Q 50/24* (2013.01); *G08B 1/08* (2013.01); *A61B 5/0809* (2013.01); *A61B 2560/0209* (2013.01); *A61B 2560/0462* (2013.01); *A61N 1/36* (2013.01); *G06F 19/00* (2013.01)

(58) Field of Classification Search
CPC ..... A61B 5/0538; A61B 5/1116; A61B 5/686; A61B 5/6882; A61B 5/0809; A61N 1/08; A61N 1/37282; A61N 1/36
USPC .......................................................... 607/60
See application file for complete search history.

(56) References Cited

U.S. PATENT DOCUMENTS

| | | |
|---|---|---|
| 4,823,797 A | 4/1989 | Heinze et al. |
| 4,915,686 A | 4/1990 | Frederick |
| 5,107,833 A | 4/1992 | Barsness |
| 5,117,824 A | 6/1992 | Keimel et al. |
| 5,127,404 A | 7/1992 | Wyborny et al. |
| 5,168,871 A | 12/1992 | Grevious |
| 5,271,395 A | 12/1993 | Wahlstrand et al. |
| 5,292,343 A | 3/1994 | Blanchette et al. |
| 5,304,119 A | 4/1994 | Balaban et al. |
| 5,314,450 A | 5/1994 | Thompson |
| 5,324,315 A | 6/1994 | Grevious |
| 5,354,319 A | 10/1994 | Wyborny et al. |
| 5,383,909 A | 1/1995 | Keimel |
| 5,484,403 A | 1/1996 | Yoakum et al. |
| 5,545,186 A | 8/1996 | Olson et al. |
| 5,755,736 A | 5/1998 | Gillberg et al. |
| 5,772,671 A | 6/1998 | Harmon |
| 5,836,975 A | 11/1998 | DeGroot |
| 5,842,999 A | 12/1998 | Pruitt et al. |
| 5,876,353 A | 3/1999 | Riff |
| 5,954,670 A | 9/1999 | Baker |
| 5,957,861 A | 9/1999 | Combs et al. |
| 5,987,352 A | 11/1999 | Klein et al. |
| 6,045,513 A | 4/2000 | Stone et al. |
| 6,102,874 A | 8/2000 | Stone et al. |
| 6,104,949 A | 8/2000 | Pitts Crick et al. |
| 6,148,233 A | 11/2000 | Owen et al. |
| 6,154,674 A | 11/2000 | Meier |
| 6,221,011 B1 | 4/2001 | Bardy |
| 6,230,059 B1 | 5/2001 | Duffin |
| 6,263,243 B1 | 7/2001 | Lang |
| 6,277,072 B1 | 8/2001 | Bardy |
| 6,280,380 B1 | 8/2001 | Bardy |
| 6,280,409 B1 | 8/2001 | Stone et al. |
| 6,336,903 B1 | 1/2002 | Bardy |
| 6,405,085 B1 | 6/2002 | Graupner et al. |
| 6,412,490 B1 | 7/2002 | Lee |
| 6,449,509 B1 | 9/2002 | Park et al. |
| 6,459,929 B1 | 10/2002 | Hopper et al. |
| 6,463,326 B1 | 10/2002 | Hartley et al. |
| 6,473,640 B1 | 10/2002 | Erlebacher |
| 6,480,733 B1 | 11/2002 | Turcott |
| 6,512,940 B1 | 1/2003 | Brabec et al. |
| 6,512,949 B1 | 1/2003 | Combs et al. |
| 6,522,915 B1 | 2/2003 | Ceballos et al. |
| 6,572,557 B2 | 6/2003 | Tchou et al. |
| 6,595,927 B2 | 7/2003 | Pitts-Crick et al. |
| 6,622,046 B2 | 9/2003 | Fraley et al. |
| 6,671,549 B2 | 12/2003 | Van Dam et al. |
| 6,719,701 B2 | 4/2004 | Lade |
| 6,821,249 B2 | 11/2004 | Casscells, III et al. |
| 6,866,629 B2 | 3/2005 | Bardy |
| 6,892,094 B2 | 5/2005 | Ousdigian et al. |
| 6,895,275 B2 | 5/2005 | Markowitz et al. |
| 6,907,288 B2 | 6/2005 | Daum |
| 6,931,272 B2 | 8/2005 | Burnes |
| 6,945,934 B2 | 9/2005 | Bardy |
| 6,960,167 B2 | 11/2005 | Bardy |
| 7,035,684 B2 | 4/2006 | Lee |
| 7,127,290 B2 | 10/2006 | Girouard et al. |
| 7,141,026 B2 * | 11/2006 | Aminian ............... A61B 5/1116 600/595 |
| 7,149,584 B1 | 12/2006 | Koh et al. |
| 7,177,681 B2 | 2/2007 | Zhu |
| 7,177,684 B1 | 2/2007 | Kroll et al. |
| 7,184,821 B2 | 2/2007 | Belalcazar et al. |
| 7,248,916 B2 | 7/2007 | Bardy |
| 7,272,442 B2 | 9/2007 | Freeberg |
| 7,308,309 B1 | 12/2007 | Koh |
| 7,310,551 B1 | 12/2007 | Koh et al. |
| 7,313,434 B2 | 12/2007 | Belalcazar et al. |
| 7,340,296 B2 | 3/2008 | Stahmann et al. |
| 7,387,610 B2 | 6/2008 | Stahmann et al. |
| 7,389,143 B2 | 6/2008 | Hopper et al. |
| 7,937,135 B2 | 5/2011 | Ghanem et al. |
| 7,991,471 B2 | 8/2011 | Ghanem et al. |
| 7,996,087 B2 | 8/2011 | Cowan et al. |
| 8,206,325 B1 | 6/2012 | Najafi et al. |
| 8,255,046 B2 | 8/2012 | Sarkar et al. |
| 8,491,504 B2 | 7/2013 | Hirth |
| 8,744,572 B1 | 6/2014 | Greenhut et al. |
| 8,818,505 B2 | 8/2014 | Bhunia et al. |
| 8,845,557 B1 | 9/2014 | Giuffrida et al. |
| 8,888,745 B2 | 11/2014 | Van Der Graaf et al. |
| 8,990,041 B2 | 3/2015 | Grabiner et al. |
| 9,403,000 B2 | 8/2016 | Lyons et al. |
| 10,264,997 B1 | 4/2019 | Romrell et al. |
| 10,335,047 B2 | 7/2019 | Gunderson |
| 2001/0011153 A1 | 8/2001 | Bardy |
| 2001/0021801 A1 | 9/2001 | Bardy |
| 2001/0039504 A1 | 11/2001 | Lindberg et al. |
| 2002/0026104 A1 | 2/2002 | Bardy |
| 2002/0115939 A1 | 8/2002 | Mulligan et al. |
| 2003/0028221 A1 | 2/2003 | Zhu et al. |
| 2003/0055461 A1 | 3/2003 | Girouard et al. |
| 2003/0125611 A1 | 7/2003 | Bardy |
| 2003/0149367 A1 | 8/2003 | Kroll et al. |
| 2003/0212445 A1 | 11/2003 | Weinberg |
| 2003/0220580 A1 | 11/2003 | Alt |
| 2004/0015197 A1 | 1/2004 | Gunderson |
| 2004/0082969 A1 | 4/2004 | Kerr |
| 2004/0102712 A1 | 5/2004 | Belalcazar et al. |
| 2004/0112151 A1 | 6/2004 | Maxwell et al. |
| 2004/0122484 A1 | 6/2004 | Hatlestad et al. |
| 2004/0172080 A1 | 9/2004 | Stadler et al. |
| 2004/0193154 A1 | 9/2004 | Leatherbury et al. |
| 2004/0249388 A1 | 12/2004 | Michelson |
| 2005/0090852 A1 | 4/2005 | Layne et al. |
| 2005/0096645 A1 | 5/2005 | Wellman et al. |
| 2005/0107768 A1 | 5/2005 | Ting |
| 2005/0124908 A1 | 6/2005 | Belalcazar et al. |
| 2006/0020295 A1 | 1/2006 | Brockway et al. |
| 2006/0030892 A1 | 2/2006 | Kadhiresan et al. |
| 2006/0074434 A1 | 4/2006 | Wenstrom et al. |
| 2006/0097331 A1 | 5/2006 | Hattori et al. |
| 2006/0106415 A1 | 5/2006 | Gabbay |
| 2006/0174898 A1 | 8/2006 | Brown |

(56) References Cited

U.S. PATENT DOCUMENTS

| | | |
|---|---|---|
| 2006/0241701 A1 | 10/2006 | Markowitz et al. |
| 2006/0276848 A1 | 12/2006 | Min et al. |
| 2006/0293609 A1 | 12/2006 | Stahmann et al. |
| 2007/0010738 A1 | 1/2007 | Mark et al. |
| 2007/0021678 A1 | 1/2007 | Beck et al. |
| 2007/0067005 A1* | 3/2007 | Schatz ............... A61N 1/37211 607/59 |
| 2007/0088394 A1 | 4/2007 | Jacobson |
| 2007/0088397 A1 | 4/2007 | Jacobson |
| 2007/0142732 A1 | 6/2007 | Brockway et al. |
| 2007/0156061 A1 | 7/2007 | Hess |
| 2007/0179515 A1 | 8/2007 | Matsutani et al. |
| 2007/0249992 A1 | 10/2007 | Bardy |
| 2008/0024293 A1 | 1/2008 | Stylos |
| 2008/0027349 A1 | 1/2008 | Stylos |
| 2008/0154298 A1 | 6/2008 | Grayzel et al. |
| 2008/0161657 A1 | 7/2008 | Bullens et al. |
| 2008/0255626 A1 | 10/2008 | Fricke et al. |
| 2008/0281550 A1 | 11/2008 | Hogle et al. |
| 2008/0288200 A1 | 11/2008 | Noble |
| 2009/0030426 A1 | 1/2009 | Zinn et al. |
| 2009/0036917 A1 | 2/2009 | Anderson |
| 2009/0137946 A1 | 5/2009 | Nassiri et al. |
| 2009/0312649 A1 | 12/2009 | Lian et al. |
| 2010/0010361 A1 | 1/2010 | Boute et al. |
| 2010/0030090 A1 | 2/2010 | Zhang et al. |
| 2010/0030227 A1 | 2/2010 | Kast et al. |
| 2010/0030292 A1 | 2/2010 | Sarkar et al. |
| 2010/0030293 A1 | 2/2010 | Sarkar et al. |
| 2010/0087745 A1 | 4/2010 | Fischell et al. |
| 2010/0094252 A1 | 4/2010 | Wengreen et al. |
| 2010/0011424 A1 | 5/2010 | Donofrio et al. |
| 2010/0114241 A1 | 5/2010 | Donofrio et al. |
| 2010/0198097 A1 | 8/2010 | Sowelam |
| 2010/0198140 A1 | 8/2010 | Lawson |
| 2010/0210975 A1 | 8/2010 | Anthony, III et al. |
| 2010/0228308 A1 | 9/2010 | Cowan et al. |
| 2010/0331868 A1 | 12/2010 | Bardy |
| 2011/0040572 A1* | 2/2011 | Chmiel ............... A61B 5/0002 705/2 |
| 2011/0071586 A1 | 3/2011 | Jacobson |
| 2011/0077865 A1 | 3/2011 | Chen et al. |
| 2011/0082350 A1 | 4/2011 | Koh |
| 2011/0106201 A1 | 5/2011 | Bhunia |
| 2011/0148400 A1 | 6/2011 | Doerr et al. |
| 2011/0172545 A1 | 7/2011 | Grudic et al. |
| 2011/0190835 A1 | 8/2011 | Brockway et al. |
| 2012/0083705 A1 | 4/2012 | Yuen et al. |
| 2012/0109235 A1 | 5/2012 | Jacobson |
| 2012/0109236 A1 | 5/2012 | Jacobson et al. |
| 2012/0109237 A1 | 5/2012 | Xiao et al. |
| 2012/0283705 A1 | 11/2012 | Lee et al. |
| 2013/0079861 A1 | 3/2013 | Reinert et al. |
| 2013/0085677 A1 | 4/2013 | Modi et al. |
| 2013/0123684 A1 | 5/2013 | Giuffrida et al. |
| 2013/0066169 A1 | 9/2013 | Rys et al. |
| 2013/0304414 A1 | 11/2013 | Levy et al. |
| 2014/0024871 A1 | 1/2014 | Yanagawa et al. |
| 2014/0128778 A1 | 5/2014 | Chan et al. |
| 2014/0128963 A1 | 5/2014 | Quill et al. |
| 2014/0276928 A1 | 9/2014 | Vanderpool et al. |
| 2014/0330172 A1* | 11/2014 | Jovanov ............... A61B 5/6898 600/595 |
| 2014/0358193 A1 | 12/2014 | Lyons et al. |
| 2014/0364769 A1 | 12/2014 | Chang et al. |
| 2015/0185044 A1 | 7/2015 | Nie et al. |
| 2015/0286285 A1 | 10/2015 | Pantelopoulos et al. |
| 2015/0342540 A1 | 12/2015 | An et al. |
| 2016/0038093 A1 | 2/2016 | Sharma et al. |
| 2016/0045140 A1 | 2/2016 | Kitamura et al. |
| 2016/0100776 A1 | 4/2016 | Najafi et al. |
| 2016/0155313 A1 | 6/2016 | Chang et al. |
| 2016/0175007 A1 | 6/2016 | Valbuena et al. |
| 2016/0209232 A1 | 7/2016 | Yang et al. |
| 2016/0220153 A1* | 8/2016 | Annegarn ............ G08B 21/0446 |
| 2017/0067933 A1 | 3/2017 | Miller et al. |
| 2017/0188897 A1 | 7/2017 | Thein et al. |
| 2017/0258346 A1 | 9/2017 | Vanderpool et al. |
| 2017/0344919 A1 | 11/2017 | Chang et al. |
| 2018/0035898 A1 | 2/2018 | Gunderson |
| 2018/0035920 A1 | 2/2018 | Gunderson et al. |
| 2018/0035924 A1 | 2/2018 | Gunderson et al. |
| 2018/0035956 A1 | 2/2018 | Gunderson et al. |

FOREIGN PATENT DOCUMENTS

| | | |
|---|---|---|
| CN | 2702718 Y | 6/2005 |
| CN | 202342097 U | 7/2012 |
| DE | 469951 C | 1/1929 |
| DE | 4243641 A1 | 9/1994 |
| DE | 10148440 A1 | 4/2003 |
| EP | 1997427 A1 | 3/2008 |
| EP | 3034128 A1 | 6/2016 |
| JP | 2001502937 A | 3/2001 |
| JP | 2007516031 A | 6/2007 |
| JP | 2008528084 A | 7/2008 |
| JP | 2011092065 A | 5/2011 |
| WO | 9813091 A1 | 4/1998 |
| WO | 9833554 A1 | 8/1998 |
| WO | 200064336 A1 | 11/2000 |
| WO | 2001032260 A1 | 5/2001 |
| WO | 2002067449 A2 | 8/2002 |
| WO | 2005044116 A2 | 5/2005 |
| WO | 2005060306 A1 | 6/2005 |
| WO | 2006/070124 A1 | 7/2006 |
| WO | 2006081432 A1 | 8/2006 |
| WO | 2007033194 A2 | 3/2007 |
| WO | 2007079354 A2 | 7/2007 |
| WO | 2008016551 A1 | 2/2008 |
| WO | 2012/098356 A1 | 7/2012 |
| WO | 2014083538 A1 | 6/2014 |

OTHER PUBLICATIONS

Veltink, et al., "Detection of Static and Dynamic Activities Using Uniaxial Accelerometers", IEEE Transacations on Rehabilitation Engineering, Dec. 1996, pp. 1063-6528, vol. 4, No. 4.

Wieling et al., "Testing for Autonomic Neuropathy: Heart Rate Changes After Orthostatic Manoeuvers and Static Muscle Contractions," Clinical Science (London), 1983, pp. 581-586, vol. 64, No. 6.

(PCT/US2017/041451) PCT Notification of Transmittal of the International Search Report and the Written Opinion of the International Searching Authority, or the Declaration, dated Sep. 21, 2017, 14 pages.

(PCT/US2017/041483) PCT Notification of Transmittal of the International Search Report and the Written Opinion of the International Searching Authority, or the Declaration, dated Sep. 25, 2017, 14 pages.

(PCT/US2017/041713) PCT Notification of Transmittal of the International Search Report and the Written Opinion of the International Searching Authority, or the Declaration, dated Sep. 27, 2017, 14 pages.

(PCT/US2017/041701) PCT Notification of Transmittal of the International Search Report and the Written Opinion of the International Searching Authority, or the Declaration, dated Oct. 18, 2017, 14 pages.

(PCT/US2017/041621) PCT Notification of Transmittal of the International Search Report and the Written Opinion of the International Searching Authority, or the Declaration, dated Oct. 27, 2017, 14 pages.

Adamson et al, "Continuous Autonomic Assessment in Patients with Symptomatic Heart Failure . . . " Circulation Journal of American Heart Association, pp. 2389-2394. 110: 16, Jun. 30, 2004.

Baer, et al. "Electronic Home Monitoring of Congestive Heart Failure Patients: Design and Feasibility", Congestive Heart Failure, 5:105-113, May/Jun. 1999.

Berman et al. "Transthoracic Electrical Impedance as a Guide to Intravascular Overload", Archives Surgery, 102, pp. 61-62, Jan. 1971.

(56) References Cited

OTHER PUBLICATIONS

Lusignan, et al. "Compliance and Effectiveness of 1 Year's Home Telemonitoring,The Report of a Pilot Study . . . " European Journal of Heart Failure, 3:723-730, Apr. 2001.
U.S. Appl. No. 16/552,925, filed Aug. 27, 2019 by Gunderson et al.
Wuerz et al., "Effects of Prehospital Medications on Mortality and Length of Stay in Congestive Heart Failure", Annals of Emergency Medicine 21:6 pp. 669-674. Jun. 1992.
Alberts et al., "Using Accelerometer and Gyroscopic Measures to Quantify Postural Stability," Journal of Athletic Training, vol. 50, No. 6, Jun. 2015, 11 pp.
Barde, "What to use to express the variability of data: Standard deviation or standard error of mean?," Perspectives in clinical Research, Jul. 2012, 5 pp.
Chang et al., "A Wireless Accelerometer-Based Body Posture Stability Detection System and Its Application for Meditation Practitioners," Sensors, ISSN: 1424-8220, Dec. 18, 2012, 13 pp.
Hubble et al., "Wearable Sensor Use for Assessing Standing Balance and Walking Stability in People with Parkinson's Disease: A Systematic Review," PLOS ONE, Apr. 20, 2015, 22 pp.
Rigoberto et al., "Postural sway parameters using a triaxial accelerometer: Comparing elderly and young healthy adults," Computer Methods in Biomechanics and Biomedical Engineering, Feb. 21, 2011, 12 pp.

\* cited by examiner

MOBILE APPLICATION TO PROMPT PHYSICAL ACTION TO MEASURE PHYSIOLOGIC RESPONSE IN IMPLANTABLE DEVICE

RELATED APPLICATIONS

This application claims the benefit of U.S. provisional application No. 62/370,146, filed Aug. 2, 2016 and is incorporated by reference herein.

FIELD

The disclosure relates generally to medical device systems, and more particularly to medical device systems configured for determining patient functional status based on accelerometer-generated data.

BACKGROUND

Implantable medical devices (IMDs) and external, e.g., wearable, medical devices, including implantable pacemakers and implantable cardioverter-defibrillators (ICDs), record cardiac electrogram (EGM) signals for sensing cardiac events, e.g., P-waves and R-waves. IMDs detect episodes of bradycardia, tachycardia and/or fibrillation from the sensed cardiac events, and respond to the episodes as needed with pacing therapy or high-voltage anti-tachyarrhythmia shocks, e.g., cardioversion or defibrillation shocks. Some such medical devices include, or are or part of a system that includes, sensors that generate other physiological-based signals, such as signals that vary based on patient movement or activity, cardiovascular pressure, blood oxygen saturation, edema, or thoracic impedance.

SUMMARY

In general, this disclosure is directed to techniques for determining patient functional status based on accelerometer-generated data. Although not so limited, a number of example implementations of such techniques are contemplated, such as:

A medical device system that includes or comprises: accelerometer circuitry configured to generate a plurality of signals including a sagittal axis signal, a vertical axis signal and a transverse axis signal; and processing circuitry configured to: calculate a patient-specific functional status parameter associated with a Sit-To-Stand test from at least one of the sagittal axis signal, the vertical axis signal and the transverse axis signal over a time segment inclusively bounded by a first and second time each generated by a user equipment and received by the system as timestamp data from the user equipment over a communication link.

A method that includes or comprises: generating, by a medical device system, a plurality of signals including a sagittal axis signal, a vertical axis signal and a transverse axis signal; and calculating, by the medical device system, a patient-specific functional status parameter associated with a Sit-To-Stand test from at least one of the sagittal axis signal, the vertical axis signal and the transverse axis signal over a time segment inclusively bounded by a first and second time each generated by a user equipment and received by the system as timestamp data from the user equipment over a communication link.

An implantable medical device (IMD) that includes or comprises: communication circuitry configured to establish a communication link and transfer data between the IMD intra-corpus and a computing device extra-corpus; accelerometer circuitry configured to generate a plurality of signals including a sagittal axis signal, a vertical axis signal and a transverse axis signal; and processing circuitry configured to: acquire first timestamp data and second timestamp data each one generated by the computing device and received by the IMD via the communication circuitry; calculate a patient-specific functional status parameter associated with a Sit-To-Stand test from at least one of the sagittal axis signal, the vertical axis signal and the transverse axis signal over a time segment inclusively bounded by a first time defined by the first timestamp data and a second time defined by the second timestamp data; and in response to a command, activate the communication circuitry to transmit the patient-specific functional status parameter from the IMD to the computing device.

A method that includes or comprises: by an implantable medical device, intra-corpus: generating a plurality of signals including a sagittal axis signal, a vertical axis signal and a transverse axis signal; receiving, from a computing device extra-corpus, first timestamp data and second timestamp data each one generated by the computing device and received by the implantable medical device over a communication link; calculating a patient-specific functional status parameter associated with a Sit-To-Stand test from at least one of the sagittal axis signal, the vertical axis signal and the transverse axis signal over a time segment inclusively bounded by a first time defined by the first timestamp data and a second time defined by the second timestamp data; and in response to a command, transmitting the patient-specific functional status parameter to the computing device.

A user equipment that includes or comprises: a touchscreen; and at least one processor configured to: generate first timestamp data based upon detection of a first touch event on the touchscreen, and second timestamp data based upon detection of a second touch event on the touchscreen, for calculation by a medical device system of a patient-specific functional status parameter associated with a Sit-To-Stand performance test over a time segment inclusively bounded by a first time defined by the first timestamp data and a second time defined by the second timestamp data.

A method that includes or comprises: by a user equipment, generating first timestamp data based upon detection of a first touch event on a touchscreen of the user equipment, and second timestamp data based upon detection of a second touch event on the touchscreen, for calculation by a medical device system of a patient-specific functional status parameter associated with a Sit-To-Stand performance test over a time segment inclusively bounded by a first time defined by the first timestamp data and a second time defined by the second timestamp data.

A user equipment that includes or comprises: communication circuitry configured to establish a communication link and transfer data between the user equipment extra-corpus and an implantable medical device (IMD) intra-corpus; and processing circuitry configured to: generate first timestamp data based upon detection of a first touch event on a touchscreen of the user equipment; generate second timestamp data based upon detection of a second touch event on the touchscreen; and in response to a command, activate the communication circuitry to transmit the patient-specific functional status parameter to the IMD for calculation of a patient-specific functional status parameter associated with a Sit-To-Stand performance test over a time segment inclusively bounded by a first time defined by the first timestamp data and a second time defined by the second timestamp data.

A method comprising: by a user equipment, generating first timestamp data based upon detection of a first touch event on a touchscreen of the user equipment; generating second timestamp data based upon detection of a second touch event on the touchscreen; and in response to a command, transmitting the patient-specific functional status parameter to an implantable medical device (IMD) for calculation of a patient-specific functional status parameter associated with a Sit-To-Stand performance test over a time segment inclusively bounded by a first time defined by the first timestamp data and a second time defined by the second timestamp data.

In other examples, a medical device system comprises means for performing any of the methods or techniques described herein.

In other examples, non-transitory computer-readable media comprise program instructions that, when executed by processing circuitry of a medical device system, cause the medical device system to perform any of the methods or techniques described herein.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

DETAILED DESCRIPTION

Implantable medical devices (IMDs) and external, e.g., wearable, medical devices, including implantable pacemakers and implantable cardioverter-defibrillators (ICDs), record cardiac electrogram (EGM) signals for sensing cardiac events, e.g., P-waves and R-waves. IMDs detect episodes of bradycardia, tachycardia and/or fibrillation from the sensed cardiac events, and respond to the episodes as needed with pacing therapy or high-voltage anti-tachyarrhythmia shocks, e.g., cardioversion or defibrillation shocks. Some such medical devices include, or are or part of a system that includes, sensors that generate other physiological-based signals, such as signals that vary based on patient movement or activity, cardiovascular pressure, blood oxygen saturation, edema, or thoracic impedance. According to the features or aspects of this disclosure, one or more of such signals may be leveraged to provide on objective measure of patient functional status.

For example, a medical device system according to certain features or aspects of this disclosure includes accelerometer circuitry configured to generate a plurality of signals including a sagittal axis signal, a vertical axis signal and a transverse axis signal, and processing circuitry configured to calculate a patient-specific functional status parameter associated with a Sit-To-Stand test from at least one of the sagittal axis signal, the vertical axis signal and the transverse axis signal over a time segment inclusively bounded by a first and second time each generated by a user equipment and received by the system as timestamp data from the user equipment over a communication link.

As another example, a user equipment according to certain features or aspects of this disclosure includes a touchscreen, and at least one processor configured to generate first timestamp data based upon detection of a first touch event on the touchscreen, and second timestamp data based upon detection of a second touch event on the touchscreen, for calculation by a medical device system of a patient-specific functional status parameter associated with a Sit-To-Stand performance test over a time segment inclusively bounded by a first time defined by the first timestamp data and a second time defined by the second timestamp data.

Such an implementation(s) may, among other things, provide an objective measure of change (or not) in well-being to help guide therapies, because a patient-specific functional status parameter associated with a Sit-To-Stand test can help determine whether health is improving, declining, or stable. Although not so limited, an appreciation of the various aspects of the present disclosure may be gained from the following discussion in connection with the drawings.

Figure 1:
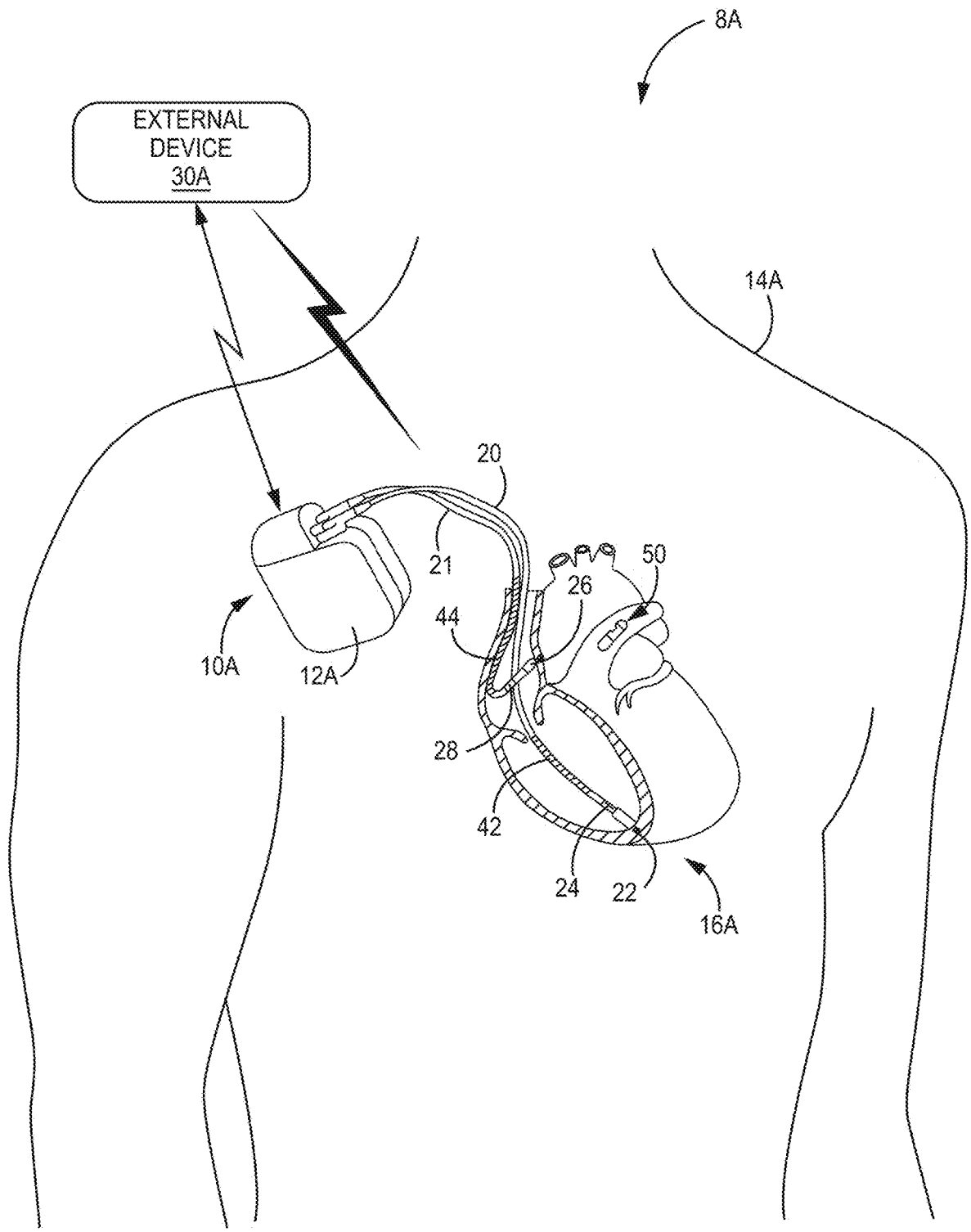
FIG. 1 is a conceptual drawing illustrating an example medical device system in conjunction with a patient.

For example, FIG. 1 is a conceptual drawing illustrating an example medical device system 8A in conjunction with a patient 14A. Medical device system 8A is an example of a medical device system configured to implement the techniques described herein for determining patient functional status based on accelerometer-generated data. In the illustrated example, medical device system 8A includes an implantable medical device (IMD) 10A coupled to a ventricular lead 20 and an atrial lead 21. IMD 10A is an implantable cardioverter-defibrillator (ICD) capable of delivering pacing, cardioversion and defibrillation therapy to the heart 16A of a patient 14A, and will be referred to as ICD 10A hereafter.

Ventricular lead 20 and atrial lead 21 are electrically coupled to ICD 10A and extend into the patient's heart 16A. Ventricular lead 20 includes electrodes 22 and 24 shown positioned on the lead in the patient's right ventricle (RV) for sensing ventricular EGM signals and pacing in the RV. Atrial lead 21 includes electrodes 26 and 28 positioned on the lead in the patient's right atrium (RA) for sensing atrial EGM signals and pacing in the RA.

Ventricular lead 20 additionally carries a high voltage coil electrode 42, and atrial lead 21 carries a high voltage coil electrode 44, used to deliver cardioversion and defibrillation shocks. The term "anti-tachyarrhythmia shock" may be used herein to refer to both cardioversion shocks and defibrillation shocks. In other examples, ventricular lead 20 may carry both of high voltage coil electrodes 42 and 44, or may carry a high voltage coil electrode in addition to those illustrated in the example of FIG. 1.

ICD 10A may use both ventricular lead 20 and atrial lead 21 to acquire cardiac electrogram (EGM) signals from patient 14A and to deliver therapy in response to the acquired data. Medical device system 8A is shown as having a dual chamber ICD configuration, but other examples may include one or more additional leads, such as a coronary sinus lead extending into the right atrium, through the coronary sinus and into a cardiac vein to position electrodes along the left ventricle (LV) for sensing LV EGM signals and delivering pacing pulses to the LV. In other examples, a medical device system may be a single chamber system, or otherwise not include atrial lead 21.

Processing circuitry, sensing circuitry, and other circuitry configured for performing the techniques described herein are housed within a sealed housing 12. Housing 12 (or a portion thereof) may be conductive so as to serve as an electrode for pacing or sensing or as an active electrode during defibrillation. As such, housing 12 is also referred to herein as "housing electrode" 12.

ICD 10A may transmit EGM signal data and cardiac rhythm episode data acquired by ICD 10A, as well as data regarding delivery of therapy by ICD 10A, as well as data in manipulated and/or in raw form, possibly compressed, encoded, and/or the like, associated with patient functional status as derived from accelerometer-generated data, to an external device 30A. External device 30A may be a computing device, e.g., used in a home, ambulatory, clinic, or hospital setting, to communicate with ICD 10A via wireless telemetry. External device 30A may be coupled to a remote patient monitoring system, such as Carelink®, available from Medtronic plc, of Dublin, Ireland. External device 30A may be, as examples, a programmer, external monitor, or consumer device, e.g., a smartphone, such as the iPhone® by Apple Inc. of Cupertino, Calif.

External device 30A may be used to program commands or operating parameters into ICD 10A for controlling its functioning, e.g., when configured as a programmer for ICD 10A, or when configured to provide timestamp data for calculating a patient-specific functional status parameter associated with a Sit-To-Stand test. External device 30A may be used to interrogate ICD 10A to retrieve data, including device operational data as well as physiological data accumulated in IMD memory, such as data associated with a patient-specific functional status parameter associated with a Sit-To-Stand test. The interrogation may be automatic, e.g., according to a schedule, or in response to a remote or local user command. Programmers, external monitors, and consumer devices are examples of external devices 30A that may be used to interrogate ICD 10A. Examples of communication techniques used by ICD 10A and external device 30A include radiofrequency (RF) telemetry, which may be an RF link established via Bluetooth, WiFi, or medical implant communication service (MICS).

In some examples, as illustrated in FIG. 1, medical device system 8A may also include a pressure-sensing IMD 50. In the illustrated example, pressure-sensing IMD 50 is implanted in the pulmonary artery of patient 14A. In some examples, one or more pressure-sensing IMDs 50 may additionally or alternatively be implanted within a chamber of heart 16A, or generally at other locations in the circulatory system.

In one example, pressure-sensing IMD 50 is configured to sense blood pressure of patient 14A. For example, pressure-sensing IMD 50 may be arranged in the pulmonary artery and be configured to sense the pressure of blood flowing from the right ventricle outflow tract (RVOT) from the right ventricle through the pulmonary valve to the pulmonary artery. Pressure-sensing IMD 50 may therefore directly measure pulmonary artery diastolic pressure (PAD) of patient 14A. The PAD value is a pressure value that can be employed in patient monitoring. For example, PAD may be used as a basis for evaluating congestive heart failure in a patient.

In other examples, however, pressure-sensing IMD 50 may be employed to measure blood pressure values other than PAD. For example, pressure-sensing IMD 50 may be arranged in right ventricle 28 of heart 14 to sense RV systolic or diastolic pressure, or may sense systolic or diastolic pressures at other locations of the cardiovascular system, such as within the pulmonary artery. As shown in FIG. 1, pressure-sensing IMD 50 is positioned in the main trunk of pulmonary artery 39. In other examples, a sensor, such as pressure-sensing IMD 50 may be either positioned in the right or left pulmonary artery beyond the bifurcation of the pulmonary artery.

Moreover, the placement of pressure-sensing IMD 50 is not restricted necessarily to the pulmonary side of the circulation. The pressure-sensing IMD 50 could potentially be placed in the systemic side of the circulation. For example, under certain conditions and with appropriate safety measures, pressure-sensing IMD 50 could even be placed in the left atrium, left ventricle, or aorta. Additionally, pressure-sensing IMD 50 is not restricted to placement within the cardiovascular system. For example, the pressure-sensing IMD 50 might be placed in the renal circulation. Placement of pressure-sensing IMD 50 in the renal circulation may be beneficial, for example, to monitor the degree of renal insufficiency in the patient based on the monitoring of pressure or some other indication of renal circulation by pressure-sensing IMD 50.

In some examples, pressure-sensing IMD 50 includes a pressure sensor configured to respond to the absolute pressure inside the pulmonary artery of patient 14A. Pressure-sensing IMD 50 may be, in such examples, any of a number of different types of pressure sensors. One form of pressure sensor that may be useful for measuring blood pressure is a capacitive pressure sensor. Another example pressure sensor is an inductive sensor. In some examples, pressure-sensing IMD 50 may also comprise a piezoelectric or piezoresistive pressure transducer. In some examples, pressure-sensing IMD 50 may comprise a flow sensor.

In one example, pressure-sensing IMD 50 comprises a leadless pressure sensor including capacitive pressure sensing elements configured to measure blood pressure within the pulmonary artery. Pressure-sensing IMD 50 may be in wireless communication with ICD 10A and/or external device 30A, e.g., in order to transmit blood pressure measurements to one or both of the devices. Pressure-sensing IMD 50 may employ, e.g., radio frequency (RF) or other telemetry techniques for communicating with ICD 10A and other devices, including, e.g., external device 30A. In another example, pressure-sensing IMD 50 may include a tissue conductance communication (TCC) system by which the device employs tissue of patient 14A as an electrical communication medium over which to send and receive information to and from ICD 10A and/or external device 30A.

Figure 2:
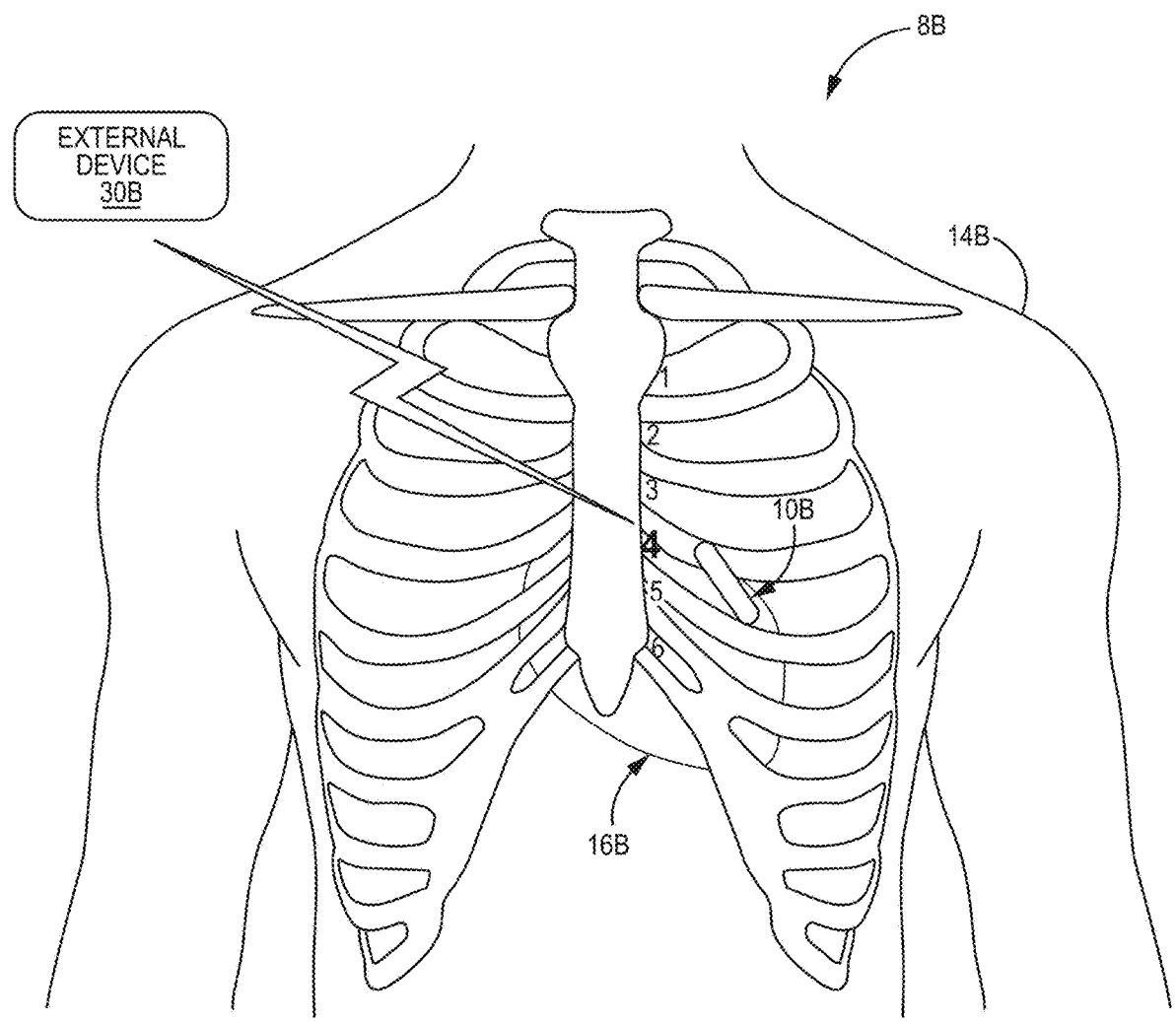
FIG. 2 is a conceptual drawing illustrating another example medical device system in conjunction with a patient.

Medical device system 8A is an example of a medical device system configured for determining patient functional status based on accelerometer-generated data. Such techniques as contemplated may be performed by processing circuitry of medical device system 8A, such as processing circuitry of one or both of ICD 10A and external device 30A, individually, or collectively, as discussed in further detail below. Other example medical device systems that may be configured to implement the techniques are described with respect to FIGS. 2-9. Although described herein primarily in the context of implantable medical devices generating signals and, in some examples, delivering therapy, a medical device system that implements the techniques described in this disclosure may additionally or alternatively include an external medical device, e.g., a smartphone, configured to at least generate timestamp data for measuring or determining patient functional status based on accelerometer-generated data FIG. 2 is a conceptual drawing illustrating another example medical device system 8B in conjunction with a patient 14B. Medical device system 8B is another example of a medical device system configured to implement the techniques described herein for determining patient functional status based on accelerometer-generated data. In the illustrated example, medical device system 8B includes an IMD 10B and an external device 30B.

IMD 10B is an insertable cardiac monitor (ICM) capable of sensing and recording cardiac EGM signals from a position outside of heart 16B, and will be referred to as ICM 10B hereafter. Further, ICM 10B is capable of implementing one or more techniques for determining patient functional status based on accelerometer-generated data in accordance with the present disclosure. In some examples, ICM 10B includes or is coupled to one or more additional sensors that generate one or more other physiological signals, such as signals that vary based on patient motion and/or posture, blood flow, or respiration. ICM 10B may be implanted outside of the thorax of patient 14B, e.g., subcutaneously or submuscularly, such as the pectoral location illustrated in FIG. 2. In some examples, ICM 10B may take the form of a Reveal LINQ™ ICM, available from Medtronic plc, of Dublin, Ireland.

External device 30B may be configured in a manner substantially similar to that described above with respect to external device 30A and FIG. 1. External device 30B may wirelessly communicate with ICM 10B, e.g., to program the functionality of the ICM, and to retrieve recorded physiological signals and/or patient parameter values or other data derived from such signals from the ICM. Both ICM 10B and external device 30B include processing circuitry, and the processing circuitry of either or both device may perform the techniques described herein for determining patient functional status based on accelerometer-generated data, as discussed in further detail below.

Although not illustrated in the example of FIG. 2, a medical device system configured to implement the techniques of this disclosure may include one or more implanted or external medical devices in addition to or instead of ICM 10B. For example, a medical device system may include a pressure sensing IMD 50, vascular ICD (e.g., ICD 10A of FIG. 1), extravascular ICD (e.g., ICD 10C of FIGS. 4A-5), or cardiac pacemaker (e.g., IPD 10D of FIGS. 4A-6 or a cardiac pacemaker implanted outside the heart but coupled to intracardiac or epicardial leads). One or more such devices may generate accelerometer signals, and include processing circuitry configured to perform, in whole or in part, the techniques described herein for determining patient functional status based on accelerometer-generated data. The implanted devices may communicate with each other and/or an external device 30, and one of the implanted or external devices may ultimately calculate a patient-specific functional status parameter associated with a Sit-To-Stand test from at least one of a sagittal axis signal, a vertical axis signal and a transverse axis signal.

Figure 3:
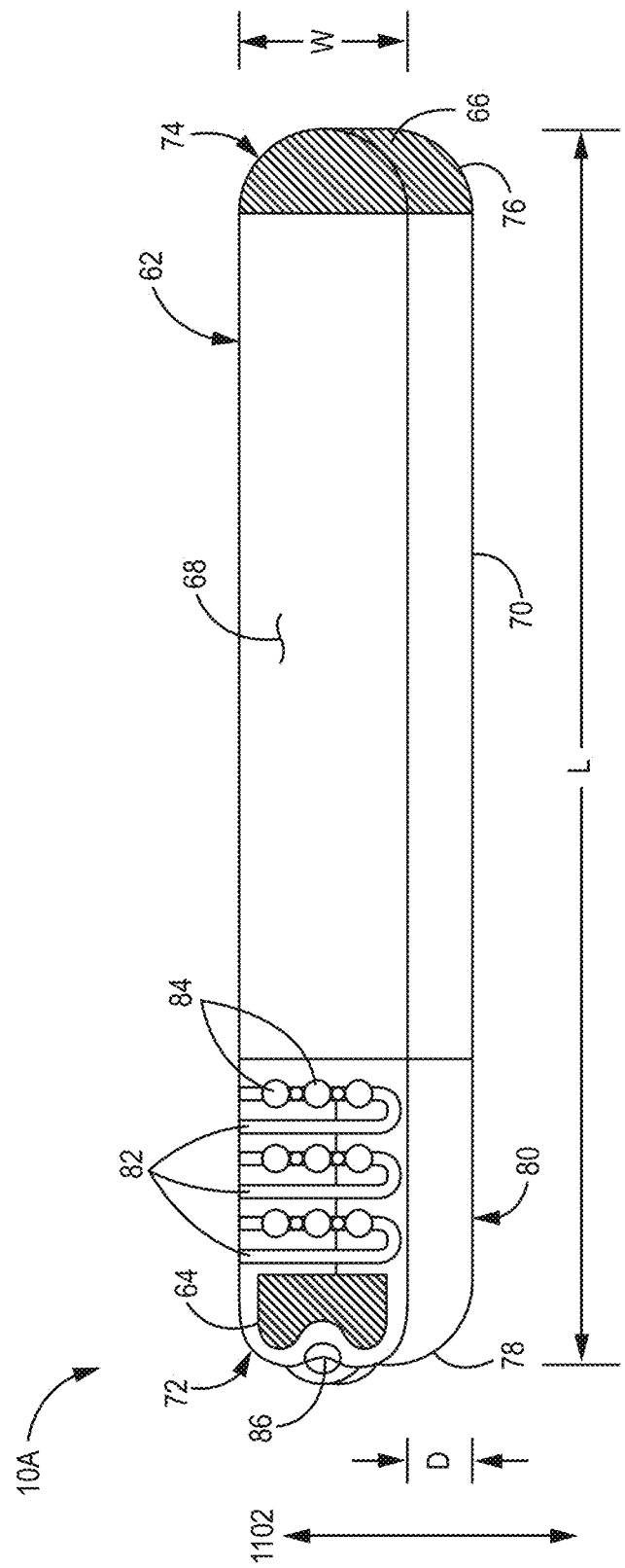
FIG. 3 is a perspective drawing illustrating an example configuration of the implantable cardiac monitor of FIG. 2.

FIG. 3 is a conceptual drawing illustrating an example configuration of ICM 10B. In the example shown in FIG. 3, ICM 300 may be embodied as a monitoring device having housing 62, proximal electrode 64 and distal electrode 66. Housing 62 may further comprise first major surface 68, second major surface 70, proximal end 72, and distal end 74. Housing 62 encloses electronic circuitry located inside the ICM 10B and protects the circuitry contained therein from body fluids. Electrical feedthroughs provide electrical connection of electrodes 64 and 66.

In the example shown in FIG. 3, ICM 10B is defined by a length L, a width W and thickness or depth D and is in the form of an elongated rectangular prism wherein the length L is much larger than the width W which in turn is larger than the depth D. In one example, the geometry of the ICM 10B—in particular a width W greater than the depth D—is selected to allow ICM 10B to be inserted under the skin of the patient using a minimally invasive procedure and to remain in the desired orientation during insertion. For example, the device shown in FIG. 3 includes radial asymmetries (notably, the rectangular shape) along the longitudinal axis that maintains the device in the proper orientation following insertion. For example, in one example the spacing between proximal electrode 64 and distal electrode 66 may range from 30 millimeters (mm) to 55 mm, 35 mm to 55 mm, and from 40 mm to 55 mm and may be any range or individual spacing from 25 mm to 60 mm. In addition, ICM 10B may have a length L that ranges from 30 mm to about 70 mm. In other examples, the length L may range from 40 mm to 60 mm, 45 mm to 60 mm and may be any length or range of lengths between about 30 mm and about 70 mm. In addition, the width W of major surface 68 may range from 3 mm to 10 mm and may be any single or range of widths between 3 mm and 10 mm. The thickness of depth D of ICM 10B may range from 2 mm to 9 mm. In other examples, the depth D of ICM 10B may range from 2 mm to 5 mm and may be any single or range of depths from 2 mm to 9 mm. In addition, ICM 10B according to an example of the present disclosure is has a geometry and size designed for ease of implant and patient comfort. Examples of ICM 10B described in this disclosure may have a volume of three cubic centimeters (cm) or less, 1.5 cubic cm or less or any volume between three and 1.5 cubic centimeters. And, as discussed in further detail below, it is contemplated that an axis coincident with an axis along D may correspond to a sagittal axis of an accelerometer, and that a sagittal axis signal(s) can be leveraged for measuring or determining patient functional status, as part of a SST (Sit-To-Stand) performance test for example. This is because 3D accelerometers in the ICM 10B, for example, which is implanted in the chest, and are relatively stationary over the lifetime of the implant. The stationary chest location presents an opportunity to monitor changes in the upper body that occur during various activities. As a person gets in and out of a chair for example the upper body has a reproducible motion (similar to a "bowing" motion) that may be identified with signals produced by the accelerometers.

In the example shown in FIG. 3, once inserted within the patient, the first major surface 68 faces outward, toward the skin of the patient while the second major surface 70 is located opposite the first major surface 68. In addition, in the example shown in FIG. 3, proximal end 72 and distal end 74 are rounded to reduce discomfort and irritation to surrounding tissue once inserted under the skin of the patient. ICM 10B, including instrument and method for inserting ICM 10B is described, for example, in U.S. Patent Publication No. 2014/0276928, incorporated herein by reference in its entirety.

Proximal electrode 64 and distal electrode 66 are used to sense cardiac signals, e.g. ECG signals, intra-thoracically or extra-thoracically, which may be sub-muscularly or subcutaneously. ECG signals may be stored in a memory of the ICM 10B, and ECG data may be transmitted via integrated antenna 82 to another medical device, which may be another implantable device or an external device, such as external device 30B. In some example, electrodes 64 and 66 may additionally or alternatively be used for sensing any biopotential signal of interest, which may be, for example, an EGM, EEG, EMG, or a nerve signal, from any implanted location.

In the example shown in FIG. 3, proximal electrode 64 is in close proximity to the proximal end 72 and distal electrode 66 is in close proximity to distal end 74. In this example, distal electrode 66 is not limited to a flattened, outward facing surface, but may extend from first major surface 68 around rounded edges 76 and/or end surface 78 and onto the second major surface 70 so that the electrode 66 has a three-dimensional curved configuration. In the example shown in FIG. 3, proximal electrode 64 is located on first major surface 68 and is substantially flat, outward facing. However, in other examples proximal electrode 64 may utilize the three-dimensional curved configuration of distal electrode 66, providing a three-dimensional proximal electrode (not shown in this example). Similarly, in other examples distal electrode 66 may utilize a substantially flat, outward facing electrode located on first major surface 68 similar to that shown with respect to proximal electrode 64.

The various electrode configurations allow for configurations in which proximal electrode 64 and distal electrode 66 are located on both first major surface 68 and second major surface 70. In other configurations, such as that shown in FIG. 3, only one of proximal electrode 64 and distal electrode 66 is located on both major surfaces 68 and 70, and in still other configurations both proximal electrode 64 and distal electrode 66 are located on one of the first major surface 68 or the second major surface 70 (i.e., proximal electrode 64 located on first major surface 68 while distal electrode 66 is located on second major surface 70). In another example, ICM 10B may include electrodes on both major surface 68 and 70 at or near the proximal and distal ends of the device, such that a total of four electrodes are included on ICM 10B. Electrodes 64 and 66 may be formed of a plurality of different types of biocompatible conductive material, e.g. stainless steel, titanium, platinum, iridium, or alloys thereof, and may utilize one or more coatings such as titanium nitride or fractal titanium nitride.

In the example shown in FIG. 3, proximal end 72 includes a header assembly 80 that includes one or more of proximal electrode 64, integrated antenna 82, anti-migration projections 84, and/or suture hole 86. Integrated antenna 82 is located on the same major surface (i.e., first major surface 68) as proximal electrode 64 and is also included as part of header assembly 80. Integrated antenna 82 allows ICM 10B to transmit and/or receive data. In other examples, integrated antenna 82 may be formed on the opposite major surface as proximal electrode 64, or may be incorporated within the housing 82 of ICM 10B. In the example shown in FIG. 3, anti-migration projections 84 are located adjacent to integrated antenna 82 and protrude away from first major surface 68 to prevent longitudinal movement of the device. In the example shown in FIG. 3, anti-migration projections 84 includes a plurality (e.g., nine) small bumps or protrusions extending away from first major surface 68. As discussed above, in other examples anti-migration projections 84 may be located on the opposite major surface as proximal electrode 64 and/or integrated antenna 82. In addition, in the example shown in FIG. 3 header assembly 80 includes suture hole 86, which provides another means of securing ICM 10B to the patient to prevent movement following insert. In the example shown, suture hole 86 is located adjacent to proximal electrode 64. In one example, header assembly 80 is a molded header assembly made from a polymeric or plastic material, which may be integrated or separable from the main portion of ICM 10B.

Figure 4A:
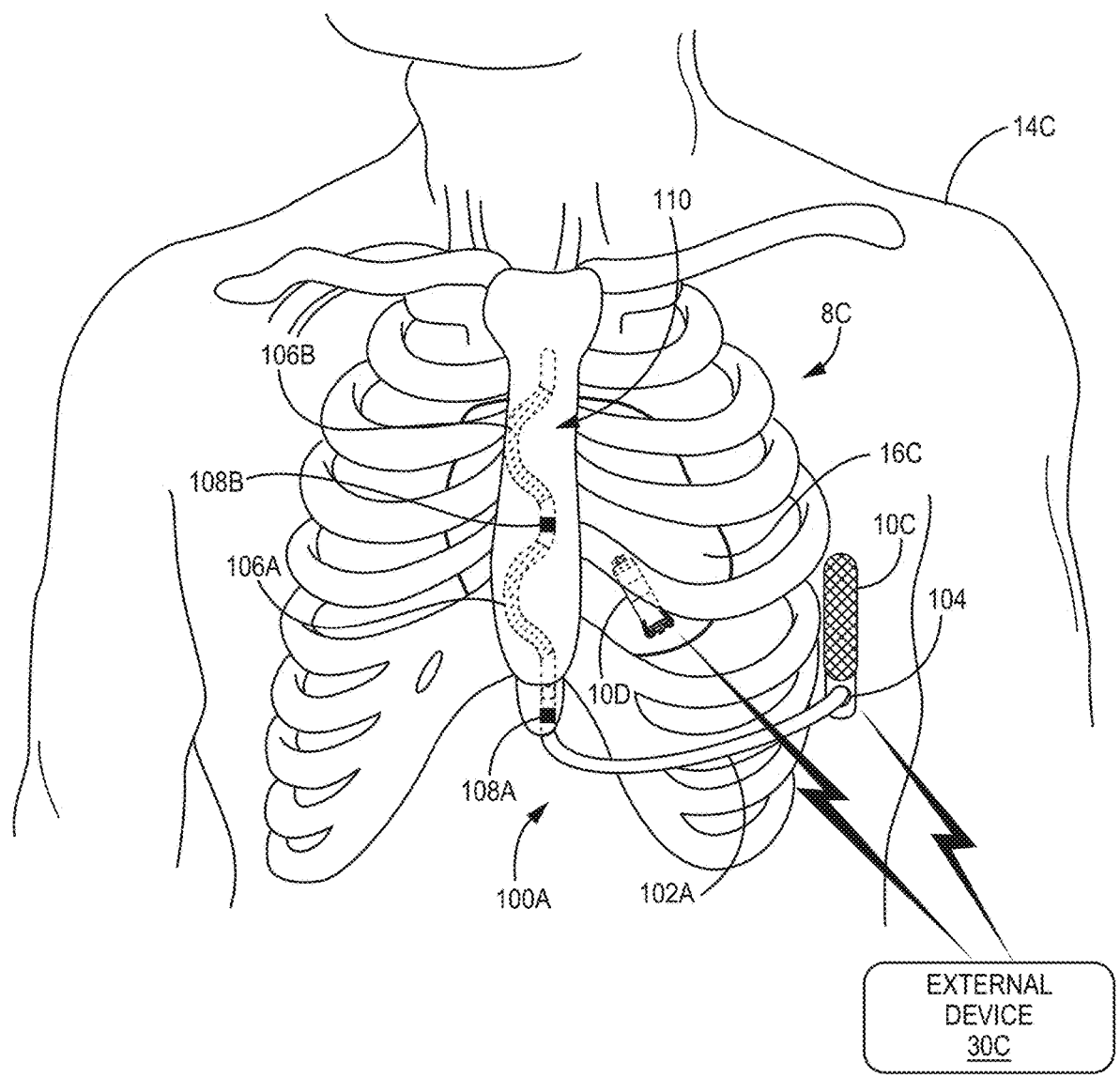
FIGS. 4A-4C is a front-view, side-view, and top-view conceptual drawings, respectively, illustrating another example medical device system in conjunction with a patient.
Figure 4B:
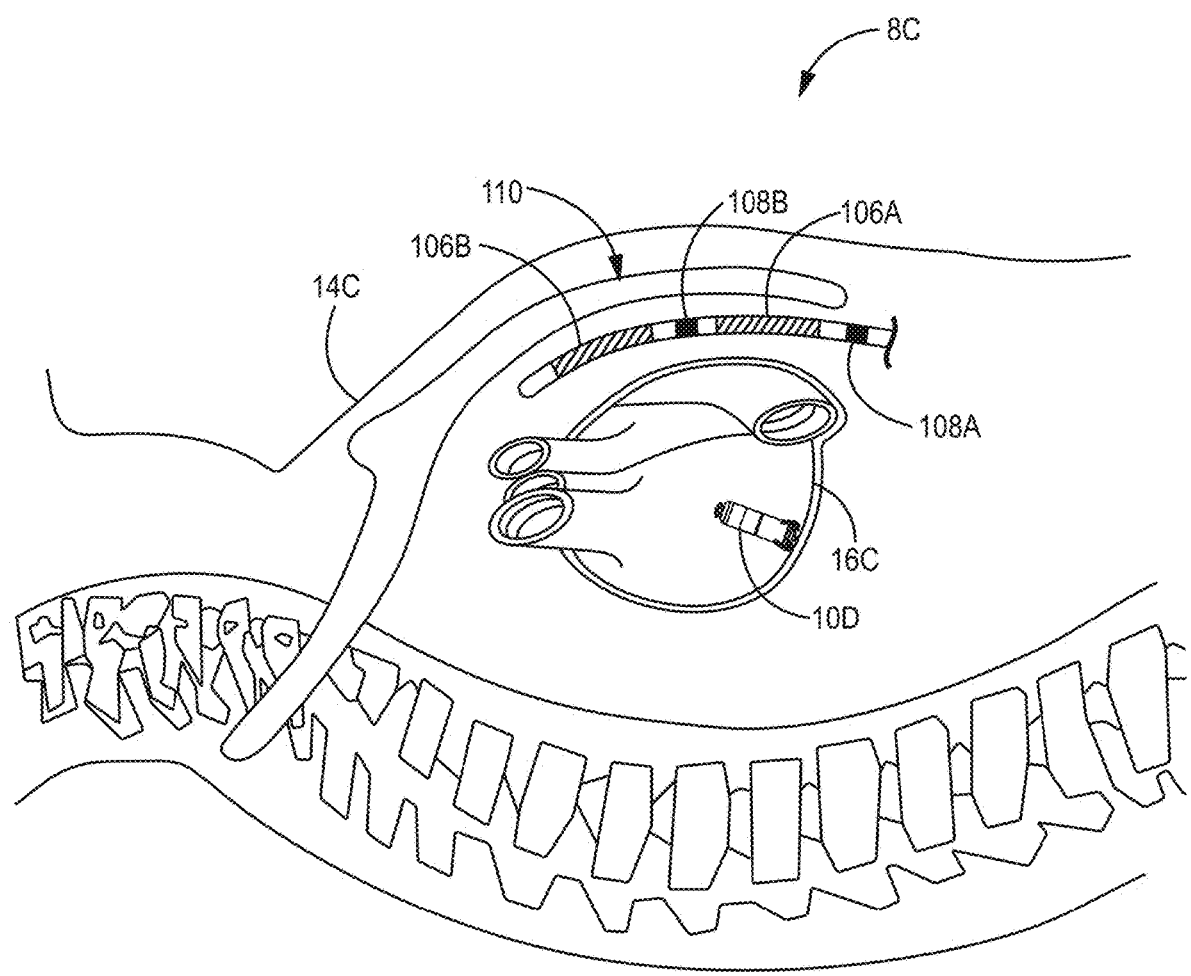
Figure 4C:
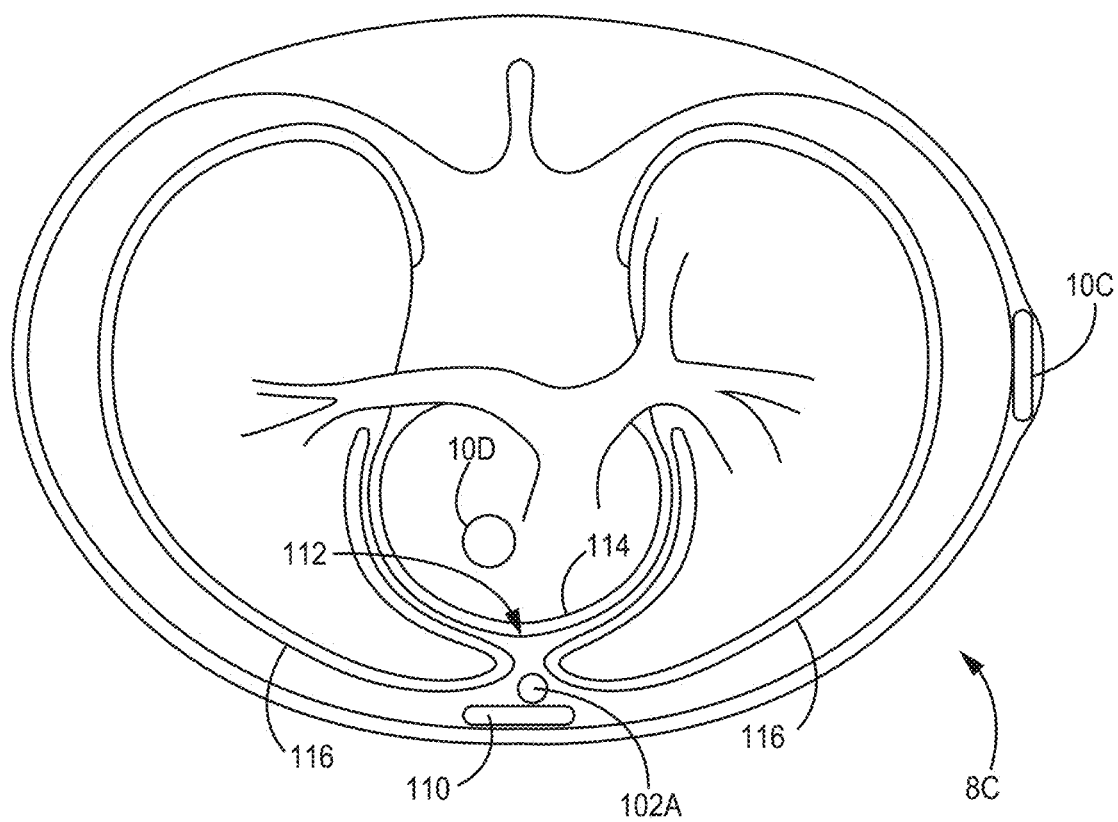

FIGS. 4A-4C are front-view, side-view, and top-view conceptual drawings, respectively, illustrating another example medical device system 8C in conjunction with a patient 14C. Medical device system 8C is another example of a medical device system configured to implement the techniques described herein for determining patient functional status based on accelerometer-generated data.

In the illustrated example, medical device system 8C includes an extracardiovascular ICD system 100A implanted within a patient 14C. ICD system 100A includes an IMD 10C, which is an ICD and is referred to hereafter as ICD 10C, connected to at least one implantable cardiac defibrillation lead 102A. ICD 10C is configured to deliver high-energy cardioversion or defibrillation pulses to a patient's heart 16C when atrial or ventricular fibrillation is detected. Cardioversion shocks are typically delivered in synchrony with a detected R-wave when fibrillation detection criteria are met. Defibrillation shocks are typically delivered when fibrillation criteria are met, and the R-wave cannot be discerned from signals sensed by ICD 10C.

ICD 10C is implanted subcutaneously or submuscularly on the left side of patient 14C above the ribcage. Defibrillation lead 102A may be implanted at least partially in a substernal location, e.g., between the ribcage and/or sternum 110 and heart 16C. In one such configuration, a proximal portion of lead 102A extends subcutaneously from ICD 10C toward sternum 110 and a distal portion of lead 102A extends superior under or below the sternum 110 in the anterior mediastinum 112 (FIG. 4C). The anterior mediastinum 112 is bounded laterally by the pleurae 116 (FIG. 1C), posteriorly by the pericardium 114 (FIG. 4C), and anteriorly by the sternum 110. In some instances, the anterior wall of the anterior mediastinum may also be formed by the transversus thoracis and one or more costal cartilages. The anterior mediastinum includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 102A extends along the posterior side of the sternum 110 substantially within the loose connective tissue and/or substernal musculature of the anterior mediastinum. Lead 102A may be at least partially implanted in other intrathoracic locations, e.g., other non-vascular, extra-pericardial locations, including the gap, tissue, or other anatomical features around the perimeter of and adjacent to, but not attached to, the pericardium or other portion of the heart and not above the sternum 110 or ribcage.

In other examples, lead 102A may be implanted at other extracardiovascular locations. For example, defibrillation lead 102A may extend subcutaneously above the ribcage from ICD 10C toward a center of the torso of patient 14C, bend or turn near the center of the torso, and extend subcutaneously superior above the ribcage and/or sternum 110. Defibrillation lead 102A may be offset laterally to the left or the right of the sternum 110 or located over the sternum 110. Defibrillation lead 102A may extend substantially parallel to the sternum 110 or be angled lateral from the sternum 110 at either the proximal or distal end.

Defibrillation lead 102A includes an insulative lead body having a proximal end that includes a connector 104 configured to be connected to ICD 10C and a distal portion that includes one or more electrodes. Defibrillation lead 102A also includes one or more conductors that form an electrically conductive path within the lead body and interconnect the electrical connector and respective ones of the electrodes.

Defibrillation lead 102A includes a defibrillation electrode that includes two sections or segments 106A and 106B, collectively (or alternatively) defibrillation electrode 106. The defibrillation electrode 106 is toward the distal portion of defibrillation lead 102A, e.g., toward the portion of defibrillation lead 102A extending along the sternum 110. Defibrillation lead 102A is placed below and/or along sternum 110 such that a therapy vector between defibrillation electrodes 106A or 106B and a housing electrode formed by or on ICD 10C (or other second electrode of the therapy vector) is substantially across a ventricle of heart 16C. The therapy vector may, in one example, be viewed as a line that extends from a point on defibrillation electrode 106 (e.g., a center of one of the defibrillation electrode sections 106A or 106B) to a point on the housing electrode of ICD 10C. Defibrillation electrode 106 may, in one example, be an elongated coil electrode.

Defibrillation lead 102A may also include one or more sensing electrodes, such as sensing electrodes 108A and 108B (individually or collectively, "sensing electrode(s) 108"), located along the distal portion of defibrillation lead 102A. In the example illustrated in FIG. 4A and FIG. 4B, sensing electrodes 108A and 108B are separated from one another by defibrillation electrode 106A. In other examples, however, sensing electrodes 108A and 108B may be both distal of defibrillation electrode 106 or both proximal of defibrillation electrode 106. In other examples, lead 102A may include more or fewer electrodes at various locations proximal and/or distal to defibrillation electrode 106. In the same or different examples, ICD 10C may include one or more electrodes on another lead (not shown).

ICD system 100A may sense electrical signals via one or more sensing vectors that include combinations of electrodes 108A and 108B and the housing electrode of ICD 10C. In some instances, ICD 10C may sense cardiac electrical signals using a sensing vector that includes one of the defibrillation electrode sections 106A and 106B and one of sensing electrodes 108A and 108B or the housing electrode of ICD 9. The sensed electrical intrinsic signals may include electrical signals generated by cardiac muscle and indicative of depolarizations and repolarizations of heart 16C at various times during the cardiac cycle. ICD 10C analyzes the electrical signals sensed by the one or more sensing vectors to detect tachyarrhythmia, such as ventricular tachycardia or ventricular fibrillation. In response to detecting the tachyarrhythmia, ICD 10C may begin to charge a storage element, such as a bank of one or more capacitors, and, when charged, deliver one or more defibrillation pulses via defibrillation electrode 106 of defibrillation lead 102A if the tachyarrhythmia is still present.

Medical device system 8C also includes an IMD 10D, which is implanted within heart 16C and configured to deliver cardiac pacing to the heart, e.g., is an intracardiac pacing device (IPD). IMD 10D is referred to as IPD 10D hereafter. In the illustrated example, IPD 10D is implanted within the right ventricle of heart 16C. However, in other examples, system 8C may additionally or alternatively include one or more IPDs 10D within other chambers of heart 16C, or similarly configured pacing devices attached to an external surface of heart 16C (e.g., in contact with the epicardium) such that the pacing device is disposed outside of heart 16C.

IPD 10D is configured to sense electrical activity of heart 16C and deliver pacing therapy, e.g., bradycardia pacing therapy, cardiac resynchronization therapy (CRT), anti-tachycardia pacing (ATP) therapy, and/or post-shock pacing, to heart 16C. IPD 10D may be attached to an interior wall of heart 16C via one or more fixation elements that penetrate the tissue. These fixation elements may secure IPD 10D to the cardiac tissue and retain an electrode (e.g., a cathode or an anode) in contact with the cardiac tissue.

IPD 10D may be capable sensing electrical signals using the electrodes carried on the housing of IPD 10D. These electrical signals may be electrical signals generated by cardiac muscle and indicative of depolarizations and repolarizations of heart 16C at various times during the cardiac cycle. IPD 10D may analyze the sensed electrical signals to detect bradycardia and tachyarrhythmias, such as ventricular tachycardia or ventricular fibrillation. In response to detecting bradycardia, IPD 10D may deliver bradycardia pacing via the electrodes of IPD 10D. In response to detecting tachyarrhythmia, IPD 10D may, e.g., depending on the type of tachyarrhythmia, deliver ATP therapy via the electrodes of IPD 10D. In some examples, IPD 10D may deliver post-shock pacing in response to determining that another medical device, e.g., ICD 10C, delivered an anti-tachyarrhythmia shock.

IPD 10D and ICD 10C may be configured to coordinate their arrhythmia detection and treatment activities. In some examples IPD 10D and ICD 10C may be configured to operate completely independently of one another. In such a case, IPD 10D and ICD 10C are not capable of establishing telemetry communication sessions with one another to exchange information about sensing and/or therapy using one-way or two-way communication. Instead, each of IPD 10D and ICD 10C analyze the data sensed via their respective electrodes to make tachyarrhythmia detection and/or therapy decisions. As such, each device does not know if the other will detect the tachyarrhythmia, if or when it will provide therapy, and the like. In some examples, IPD 10D may be configured to detect anti-tachyarrhythmia shocks delivered by ICD system 100A, which may improve the coordination of therapy between subcutaneous ICD 10C and IPD 10D without requiring device-to-device communication. In this manner, IPD 10D may coordinate the delivery of cardiac stimulation therapy, including the termination of ATP and the initiation of the delivery of post-shock pacing, with the application of an anti-tachyarrhythmia shock merely through the detection of defibrillation pulses and without the need to communicate with the defibrillation device applying the anti-tachyarrhythmia shock.

In other examples, IPD 10D and ICD 10C may engage in communication to facilitate the appropriate detection of arrhythmias and/or delivery of therapy. The communication may include one-way communication in which one device is configured to transmit communication messages and the other device is configured to receive those messages. The communication may instead include two-way communication in which each device is configured to transmit and receive communication messages. Two-way communication and coordination of the delivery of patient therapies between IPD 10D and ICD 10C is described in commonly-assigned U.S. patent application Ser. No. 13/756,085, titled, "SYSTEMS AND METHODS FOR LEADLESS PACING AND SHOCK THERAPY," filed Jan. 31, 2013, the entire content of which is incorporated by reference herein.

External device 30C may be configured substantially similarly to external device 30A described above with respect to FIG. 1. External device 30C may be configured to communicate with one or both of ICD 10C and IPD 10D. In examples where external device 30C only communicates with one of ICD 10C and IPD 10D, the non-communicative device may receive instructions from or transmit data to the device in communication with external device 30C. In some examples, a user may interact with device 30C remotely via a networked computing device. The user may interact with external device 30C to communicate with IPD 10D and/or ICD 10C.

For example, the user may interact with external device 30C to send an interrogation request and retrieve sensed physiological data or therapy delivery data stored by one or both of ICD 10C and IPD 10D, and program or update therapy parameters that define therapy, or perform any other activities with respect to ICD 10C and IPD 10D. Although the user is a physician, technician, surgeon, electrophysiologist, or other healthcare professional, the user may be patient 14C in some examples. For example, external device 30C may allow a user to program any coefficients, weighting factors, or techniques for determining difference metrics, scores, and/or thresholds, or other data described herein as being used by a medical device system to determine patient functional status based on accelerometer-generated data. As another example, external device 30C may be used to program commands or operating parameters into ICD 10C for controlling its functioning. External device 30C may be used to interrogate ICD 10C to retrieve data, including device operational data as well as physiological data accumulated in IMD memory, such as data associated with a patient-specific functional status parameter associated with a Sit-To-Stand test. ICD 10C may be configured to implement the various features or aspects of the present disclosure for determining patient functional status based on accelerometer-generated data.

Figure 33:
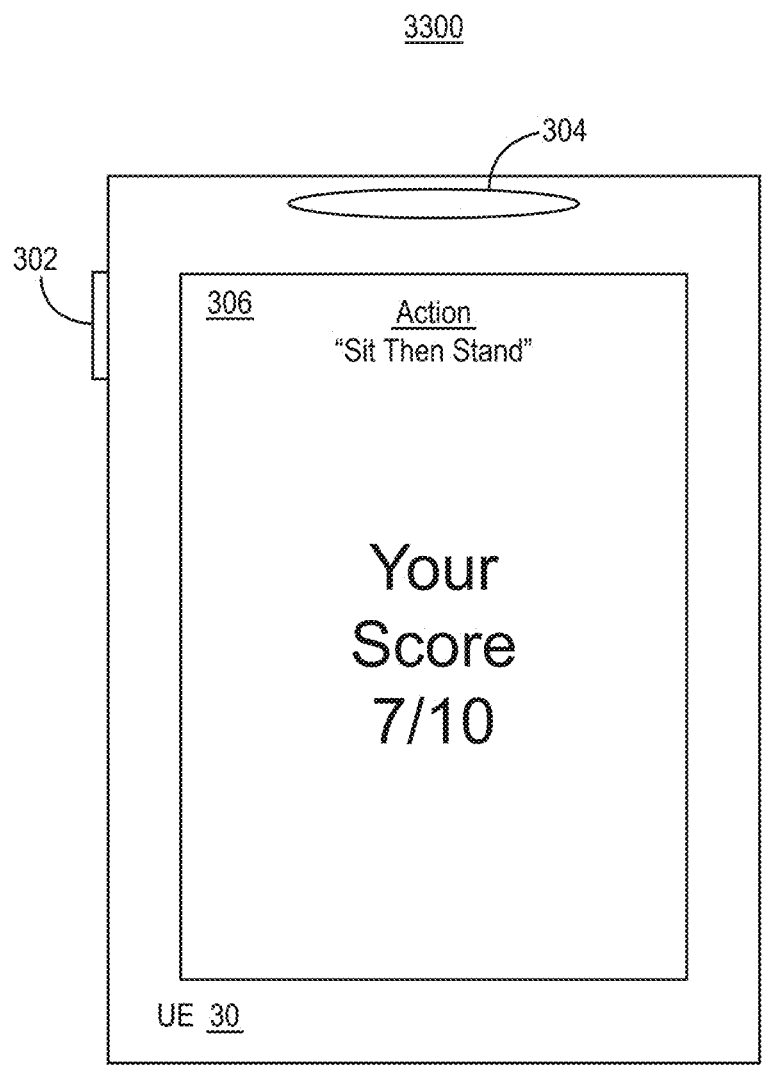

Medical device system 10D is an example of a medical device system configured for determining patient functional status based on accelerometer-generated data. Such techniques as contemplated may be performed by processing circuitry of medical device system 10D, such as processing circuitry of one or both of system 10D and external device 30C, individually, or collectively, as discussed in further detail below following a description provided in connection with FIG. 33. Other example medical device systems that may be configured to implement the techniques are described below.

Figure 5:
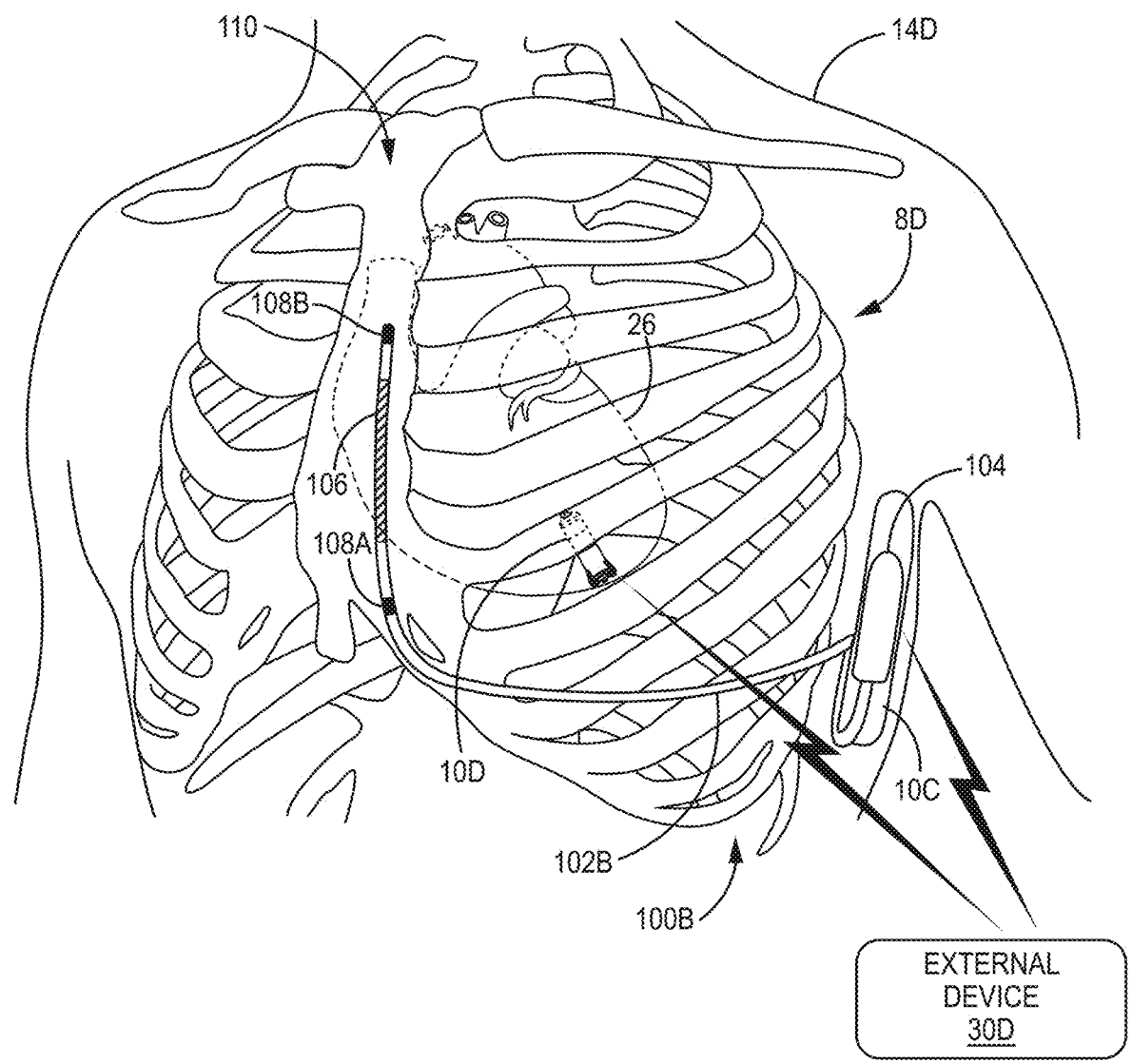
FIG. 5 is a conceptual drawing illustrating another example medical device system in conjunction with a patient.

FIG. 5 is a conceptual drawing illustrating another example medical device system 8D that includes an extra-cardiovascular ICD system 100B and IPD 10D implanted within a patient. Medical device system 8B may be configured to perform any of the techniques described herein with respect to medical device system 8C of FIGS. 4A-4C. Components with like numbers in FIGS. 4A-4C and FIG. 5 may be similarly configured and provide similar functionality.

In the example of FIG. 5, extracardiovascular ICD system 100B includes ICD 10C coupled to a defibrillation lead 102B. Unlike defibrillation lead 102A of FIGS. 4A-4C, defibrillation lead 102B extends subcutaneously above the ribcage from ICD 10C. In the illustrated example, defibrillation lead 102B extends toward a center of the torso of patient 14D, bends or turns near the center of the torso, and extends subcutaneously superior above the ribcage and/or sternum 110. Defibrillation lead 102B may be offset laterally to the left or the right of sternum 110 or located over sternum 110. Defibrillation lead 102B may extend substantially parallel to sternum 102 or be angled lateral from the sternum at either the proximal or distal end.

Defibrillation lead 102B includes an insulative lead body having a proximal end that includes a connector 104 configured to be connected to ICD 10C and a distal portion that includes one or more electrodes. Defibrillation lead 102B also includes one or more conductors that form an electrically conductive path within the lead body and interconnect the electrical connector and respective ones of the electrodes. In the illustrated example, defibrillation lead 102B includes a single defibrillation electrode 106 toward the distal portion of defibrillation lead 102B, e.g., toward the portion of defibrillation lead 102B extending along sternum 110. Defibrillation lead 102B is placed along sternum 110 such that a therapy vector between defibrillation electrode 106 and a housing electrode formed by or on ICD 10C (or other second electrode of the therapy vector) is substantially across a ventricle of heart 16D.

Defibrillation lead 102B may also include one or more sensing electrodes, such as sensing electrodes 108A and 108B, located along the distal portion of defibrillation lead 102B. In the example illustrated in FIG. 5, sensing electrodes 108A and 108B are separated from one another by defibrillation electrode 106. In other examples, however, sensing electrodes 108A and 108B may be both distal of defibrillation electrode 106 or both proximal of defibrillation electrode 106. In other examples, lead 102B may include more or fewer electrodes at various locations proximal and/or distal to defibrillation electrode 106, and lead 102B may include multiple defibrillation electrodes, e.g., defibrillation electrodes 106A and 106B as illustrated in the example of FIGS. 4A-4C.

Medical device system 8D is an example of a medical device system configured for determining patient functional status based on accelerometer-generated data. Such techniques as contemplated may be performed by processing circuitry of medical device system 8D, such as processing circuitry of one or both of system 8D and external device 30D, individually, or collectively, as discussed in further detail below.

Figure 6:
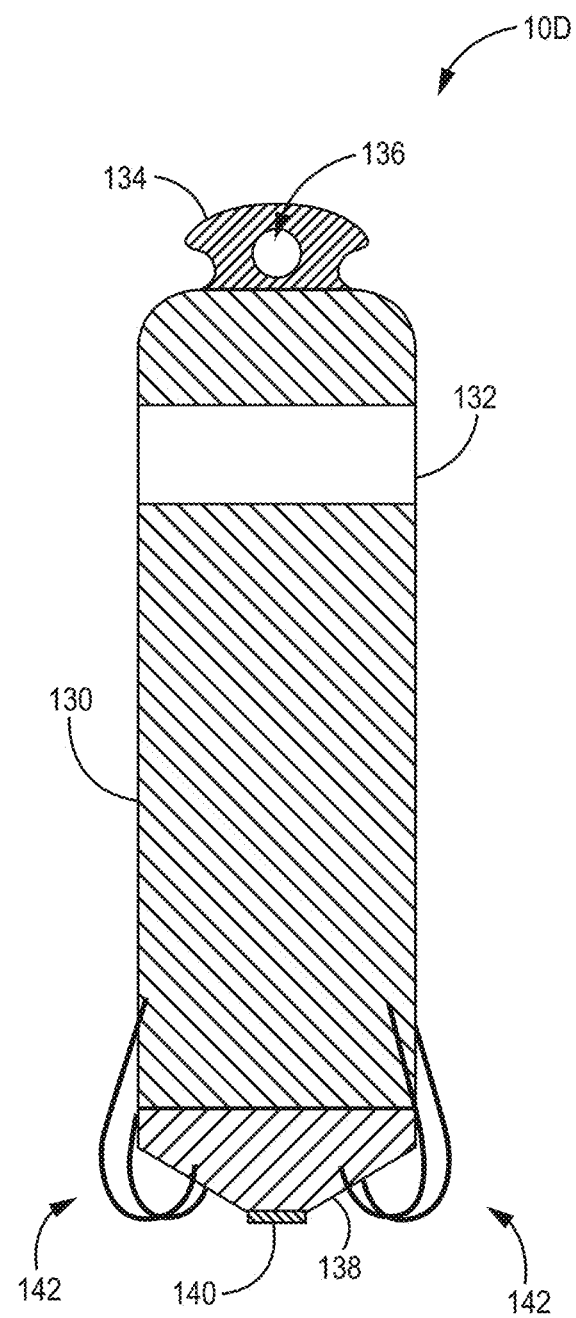
FIG. 6 is a conceptual diagram illustrating an example configuration of the intracardiac pacing device of FIGS. 4A-5.

FIG. 6 is a conceptual drawing illustrating an example configuration of IPD 10D. As shown in FIG. 6, IPD 10D includes case 130, cap 138, electrode 140, electrode 132, fixation mechanisms 142, flange 134, and opening 136. Together, case 130 and cap 138 may be considered the housing of IPD 10D. In this manner, case 130 and cap 138 may enclose and protect the various electrical components, e.g., circuitry, within IPD 10D. Case 130 may enclose substantially all of the electrical components, and cap 138 may seal case 130 and create the hermetically sealed housing of IPD 10D. Although IPD 10D is generally described as including one or more electrodes, IPD 10D may typically include at least two electrodes (e.g., electrodes 132 and 140) to deliver an electrical signal (e.g., therapy such as cardiac pacing) and/or provide at least one sensing vector.

Electrodes 132 and 140 are carried on the housing created by case 130 and cap 138. In this manner, electrodes 132 and 140 may be considered leadless electrodes. In the example of FIG. 6, electrode 140 is disposed on the exterior surface of cap 138. Electrode 140 may be a circular electrode positioned to contact cardiac tissue upon implantation. Electrode 132 may be a ring or cylindrical electrode disposed on the exterior surface of case 130. Both case 130 and cap 138 may be electrically insulating.

Electrode 140 may be used as a cathode and electrode 132 may be used as an anode, or vice versa, for delivering cardiac pacing such as bradycardia pacing, CRT, ATP, or post-shock pacing. However, electrodes 132 and 140 may be used in any stimulation configuration. In addition, electrodes 132 and 140 may be used to detect intrinsic electrical signals from cardiac muscle.

Fixation mechanisms 142 may attach IPD 10D to cardiac tissue. Fixation mechanisms 142 may be active fixation tines, screws, clamps, adhesive members, or any other mechanisms for attaching a device to tissue. As shown in the example of FIG. 6, fixation mechanisms 142 may be constructed of a memory material, such as a shape memory alloy (e.g., nickel titanium), that retains a preformed shape. During implantation, fixation mechanisms 142 may be flexed forward to pierce tissue and allowed to flex back towards case 130. In this manner, fixation mechanisms 142 may be embedded within the target tissue.

Flange 144 may be provided on one end of case 130 to enable tethering or extraction of IPD 10D. For example, a suture or other device may be inserted around flange 144 and/or through opening 146 and attached to tissue. In this manner, flange 144 may provide a secondary attachment structure to tether or retain IPD 10D within heart 16C (or 16D) if fixation mechanisms 142 fail. Flange 144 and/or opening 146 may also be used to extract IPD 10D once the IPD needs to be explanted (or removed) from patient 14D if such action is deemed necessary.

Referring back to FIGS. 4A-5, medical device systems 8C and 8D are examples of medical device systems configured for determining patient functional status based on accelerometer-generated data. Such techniques may be performed by processing circuitry of medical device system 8C or 8D, such as processing circuitry of one or more of ICD 10C, IPD 10D, and external device 30C or 30D, individually, or collectively. Although the example medical devices systems 8C and 8D of FIGS. 4A-5 are illustrated as including both ICD 10C and IPD 10D, other examples may include only one of ICD 10C or IPD 10D, alone, or in combination with other implanted or external devices.

Figure 7:
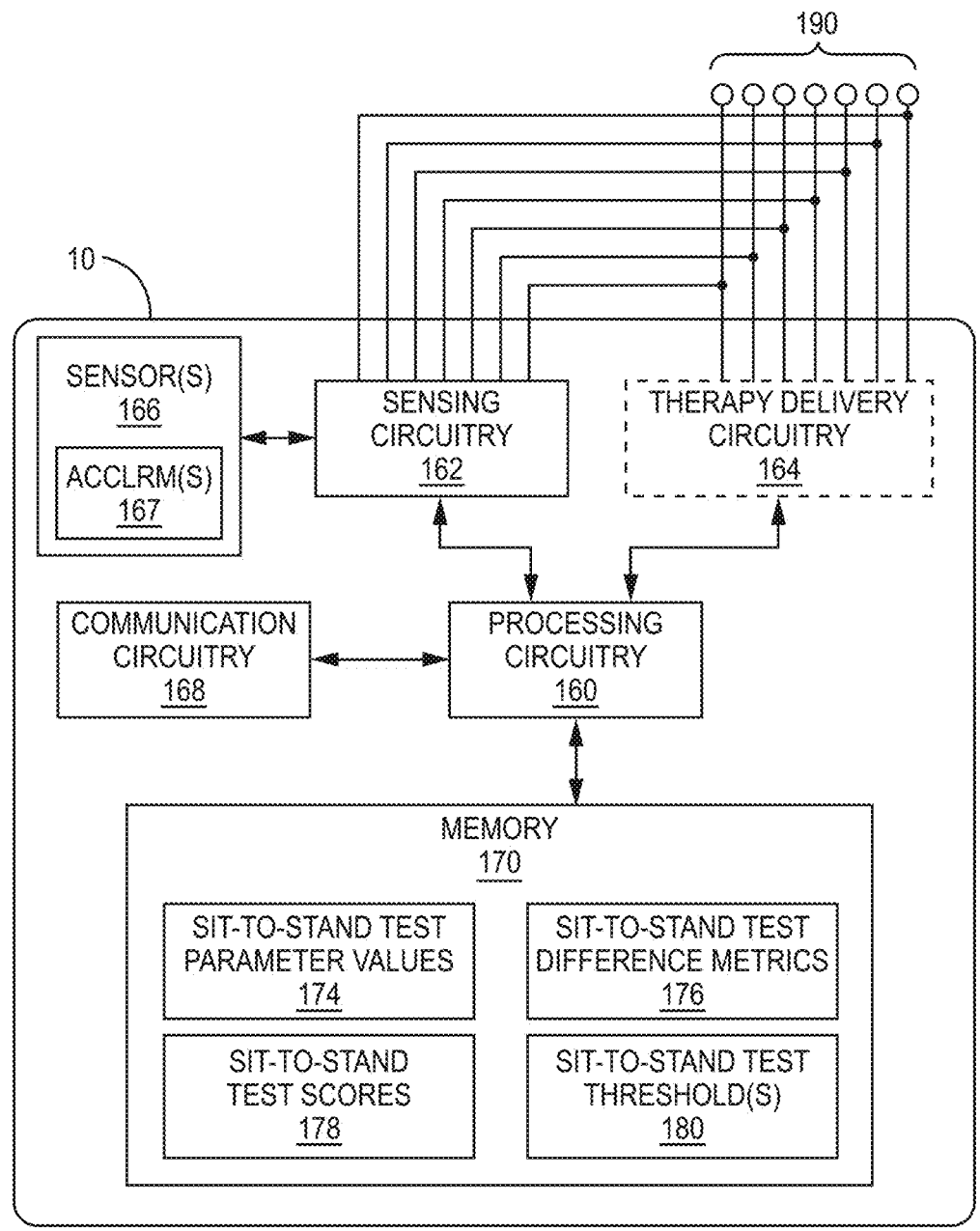
FIG. 7 is a functional block diagram illustrating an example configuration of an implantable medical device.

FIG. 7 is a functional block diagram illustrating an example configuration of an IMD 10. IMD 10 may correspond to any of ICD 10A, ICM 10B, ICD 10C, IPD 10D, or another IMD configured to implement the techniques for determining patient functional status based on accelerometer-generated data described in this disclosure. In the illustrated example, IMD 10 includes processing circuitry 160 and an associated memory 170, sensing circuitry 162, therapy delivery circuitry 164, one or more sensors 166, and communication circuitry 168. However, ICD 10A, ICM 10B, ICD 10C, and IPD 10D need not include all of these components, or may include additional components. For example, ICM 10B may not include therapy delivery circuitry 164, in some examples (illustrated by intermittent line).

Memory 170 includes computer-readable instructions that, when executed by processing circuitry 160, cause IMD 10 and processing circuitry 160 to perform various functions attributed to IMD 10 and processing circuitry 160 herein (e.g., calculate a patient-specific functional status parameter associated with a Sit-To-Stand test from at least one of the sagittal axis signal, the vertical axis signal and the transverse axis signal). Memory 170 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 160 may include fixed function circuitry and/or programmable processing circuitry. Processing circuitry 160 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 160 may include multiple components, such as any combination of one or more microprocessors, one or more controllers, one or more DSPs, one or more ASICs, or one or more FPGAs, as well as other discrete or integrated logic circuitry. The functions attributed to processing circuitry 160 herein may be embodied as software, firmware, hardware or any combination thereof.

Sensing circuitry 162 and therapy delivery circuitry 164 are coupled to electrodes 190. Electrodes 190 illustrated in FIG. 7 may correspond to, for example: electrodes 12, 22, 24, 26, 28, 44, and 44 of ICD 10A (FIG. 1); electrodes 64 and 66 of ICM 10B (FIG. 3); electrodes 106, 108, and one or more housing electrodes of ICD 10C (FIGS. 4A-5); or electrodes 132 and 140 of IPD 10D (FIG. 6).

Sensing circuitry 162 monitors signals from a selected two or more of electrodes 190 in order to monitor electrical activity of heart 26, impedance, or other electrical phenomenon. Sensing of a cardiac electrical signal may be done to determine heart rates or heart rate variability, or to detect arrhythmias (e.g., tachyarrhythmias or bradycardia) or other electrical signals. In some examples, sensing circuitry 162 may include one or more filters and amplifiers for filtering and amplifying a signal received from electrodes 190.

The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter. Sensing circuitry 162 outputs an indication to processing circuitry 160 in response to sensing of a cardiac event (e.g., detected P-waves or R-waves).

In this manner, processing circuitry 160 may receive detected cardiac event signals corresponding to the occurrence of detected R-waves and P-waves in the respective chambers of heart 26. Indications of detected R-waves and P-waves may be used for detecting ventricular and/or atrial tachyarrhythmia episodes, e.g., ventricular or atrial fibrillation episodes. Some detection channels may be configured to detect cardiac events, such as P- or R-waves, and provide indications of the occurrences of such events to processing circuitry 160, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

Sensing circuitry 162 may also include a switch module to select which of the available electrodes 190 (or electrode polarities) are used to sense the heart activity. In examples with several electrodes 190, processing circuitry 160 may select the electrodes that function as sense electrodes, i.e., select the sensing configuration, via the switch module within sensing circuitry 162. Sensing circuitry 162 may also pass one or more digitized EGM signals to processing circuitry 160 for analysis, e.g., for use in cardiac rhythm discrimination.

Processing circuitry 160 may implement programmable counters. If IMD 10 is configured to generate and deliver pacing pulses to heart 26, such counters may control the basic time intervals associated with bradycardia pacing (e.g., DDD, VVI, DVI, VDD, AAI, DDI, DDDR, VVIR, DVIR, VDDR, AAIR, DDIR pacing) and other modes of pacing. Intervals defined by processing circuitry 160 may include atrial and ventricular pacing escape intervals, refractory periods during which sensed P-waves and R-waves are ineffective to restart timing of the escape intervals, and the pulse widths of the pacing pulses. The durations of these intervals may be determined by processing circuitry 160 in response to pacing mode parameters stored in memory 170.

Interval counters implemented by processing circuitry 160 may be reset upon sensing of R-waves and P-waves with detection channels of sensing circuitry 162, or upon the generation of pacing pulses by therapy delivery circuitry 164, and thereby control the basic timing of cardiac pacing functions, including bradycardia pacing, CRT, ATP, or post-shock pacing. The value of the count present in the interval counters when reset by sensed R-waves and P-waves may be used by processing circuitry 160 to measure the durations of R-R intervals, P-P intervals, P-R intervals and R-P intervals, which are measurements that may be stored in memory 170. Processing circuitry 160 may use the count in the interval counters to detect a tachyarrhythmia event, such as atrial fibrillation (AF), atrial tachycardia (AT), VF, or VT. These intervals may also be used to detect the overall heart rate, ventricular contraction rate, and heart rate variability. A portion of memory 170 may be configured as a plurality of recirculating buffers, capable of holding series of measured intervals, which may be analyzed by processing circuitry 160 in response to the occurrence of a pace or sense interrupt to determine whether the patient's heart 26 is presently exhibiting atrial or ventricular tachyarrhythmia.

In some examples, an arrhythmia detection method may include any suitable tachyarrhythmia detection algorithms. In one example, processing circuitry 160 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies, such as those methodologies that utilize timing and morphology of the electrocardiogram, may also be employed by processing circuitry 160 in other examples.

In some examples, processing circuitry 160 may determine that tachyarrhythmia has occurred by identification of shortened R-R (or P-P) interval lengths. Generally, processing circuitry 160 detects tachycardia when the interval length falls below 220 milliseconds and fibrillation when the interval length falls below 180 milliseconds. In other examples, processing circuitry 160 may detect ventricular tachycardia when the interval length falls between 330 milliseconds and ventricular fibrillation when the interval length falls below 240 milliseconds. These interval lengths are merely examples, and a user may define the interval lengths as desired, which may then be stored within memory 170. This interval length may need to be detected for a certain number of consecutive cycles, for a certain percentage of cycles within a running window, or a running average for a certain number of cardiac cycles, as examples. In other examples, additional patient parameters may be used to detect an arrhythmia. For example, processing circuitry 160 may analyze one or more morphology measurements, impedances, or any other physiological measurements to determine that patient 14 is experiencing a tachyarrhythmia.

In addition to detecting and identifying specific types of cardiac events, e.g., cardiac depolarizations, sensing circuitry 162 may also sample the detected intrinsic signals to generate an electrogram or other time-based indication of cardiac events. Sensing circuitry 162 may include an analog-to-digital converter or other circuitry configured to sample and digitize the electrical signal sensed via electrodes 190. Processing circuitry 160 may analyze the digitized signal for a variety of purposes, including morphological identification or confirmation of tachyarrhythmia of heart 26. As another example, processing circuitry 160 may analyze the digitized cardiac electrogram signal to identify and measure a variety of morphological features of the signal.

In some examples, sensing circuitry 162 is configured to sense other physiological signals of patient. For example, sensing circuitry 162 may be configured to sense signals that vary with changing thoracic impedance of patient 14. The thoracic impedance may vary based on fluid volume or edema in patient 14.

Sensing circuitry 162 may use any two or more of electrodes 190 to sense thoracic impedance. As the tissues within the thoracic cavity of patient 14 change in fluid content, the impedance between two electrodes may also change. For example, the impedance between a defibrillation coil electrode (42, 44, 106) and the housing electrode may be used to monitor changing thoracic impedance.

In some examples, processing circuitry 160 measured thoracic impedance values to determine a fluid index. As more fluid is retained within patient 14, e.g., edema increases, and the thoracic impedance decreases or remains relatively high, the fluid index increases. Conversely, as the thoracic impedance increases or remains relatively low, the fluid index decreases. An example system for measuring thoracic impedance and determining a fluid index is described in U.S. Patent Publication No. 2010/0030292 to Sarkar et al., entitled, "DETECTING WORSENING HEART FAILURE BASED ON IMPEDANCE MEASUREMENTS," which published on Feb. 4, 2010 and is incorporated herein by reference in its entirety.

The thoracic impedance may also vary with patient respiration. In some examples, processing circuitry 160 may determine values of one or more respiration-related patient parameters based on thoracic impedance sensed by sensing circuitry 162. Respiration-related patient parameters may include, as examples, respiration rate, respiration depth, or the occurrence or magnitude of dyspnea or apneas.

The magnitude of the cardiac electrogram may also vary based on patient respiration, e.g., generally at a lower frequency than the cardiac cycle. In some examples, processing circuitry 160 and/or sensing circuitry 162 may filter the cardiac electrogram to emphasize the respiration component of the signal. Processing circuitry 160 may analyze the filtered cardiac electrogram signal to determine values of respiration-related patient parameters.

In the example of FIG. 7, IMD 10 includes one or more sensors 166 coupled to sensing circuitry 162. Although illustrated in FIG. 7 as included within IMD 10, one or more of sensors 166 may be external to IMD 10, e.g., coupled to IMD 10 via one or more leads, or configured to wirelessly communicate with IMD 10. In some examples, sensors 166 transduce a signal indicative of a patient parameter, which may be amplified, filtered, or otherwise processed by sensing circuitry 162. In such examples, processing circuitry 160 determines values of patient parameters based on the signals. In some examples, sensors 166 determine the patient parameter values, and communicate them, e.g., via a wired or wireless connection, to processing circuitry 160.

In some examples, sensors 166 include one or more accelerometers 167, e.g., one or more 3-axis accelerometers. Signals generated by the one or more accelerometers 167, such as one or more of a sagittal axis signal, a vertical axis signal and a transverse axis signal, may be indicative of, as examples, gross body movement (e.g., activity) of patient 14, patient posture, heart sounds or other vibrations or movement associated with the beating of the heart, or coughing, rales, or other respiration abnormalities. In some examples, sensors 166 include one or more microphones configured to detect heart sounds or respiration abnormalities, and/or other sensors configured to detect patient activity or posture, such as gyroscopes and/or strain gauges. In some examples, sensors 166 may include sensors configured to transduce signals indicative of blood flow, oxygen saturation of blood, or patient temperature, and processing circuitry 160 may determine patient parameters values based on these signals.

In some examples, sensors 166 include one or more pressure sensors that transduce one or more signals indicative of blood pressure, and processing circuitry 160 determines one or more patient parameter values based on the pressure signals. Patient parameter values determined based on pressure may include, as examples, systolic or diastolic pressure values, such as pulmonary artery diastolic pressure values. In some examples, a separate pressure-sensing IMD 50 includes one or more sensors and sensing circuitry configured to generate a pressure signal, and processing circuity 160 determines patient parameter values related to blood pressure based on information received from IMD 50.

Therapy delivery circuitry 164 is configured to generate and deliver electrical therapy to the heart. Therapy delivery circuitry 164 may include one or more pulse generators, capacitors, and/or other components capable of generating and/or storing energy to deliver as pacing therapy, defibrillation therapy, cardioversion therapy, other therapy or a combination of therapies. In some instances, therapy delivery circuitry 164 may include a first set of components configured to provide pacing therapy and a second set of components configured to provide anti-tachyarrhythmia shock therapy. In other instances, therapy delivery circuitry 164 may utilize the same set of components to provide both pacing and anti-tachyarrhythmia shock therapy. In still other instances, therapy delivery circuitry 164 may share some of the pacing and shock therapy components while using other components solely for pacing or shock delivery.

Therapy delivery circuitry 164 may include charging circuitry, one or more charge storage devices, such as one or more capacitors, and switching circuitry that controls when the capacitor(s) are discharged to electrodes 190 and the widths of pulses. Charging of capacitors to a programmed pulse amplitude and discharging of the capacitors for a programmed pulse width may be performed by therapy delivery circuitry 164 according to control signals received from processing circuitry 160, which are provided by processing circuitry 160 according to parameters stored in memory 170. Processing circuitry 160 controls therapy delivery circuitry 164 to deliver the generated therapy to the heart via one or more combinations of electrodes 190, e.g., according to parameters stored in memory 170. Therapy delivery circuitry 164 may include switch circuitry to select which of the available electrodes 190 are used to deliver the therapy, e.g., as controlled by processing circuitry 160.

In some examples, processing circuitry 160 periodically, i.e., for each of a plurality of periods, determines a respective value for each of a plurality of patient parameters. The determined patient parameter values are stored as patient parameter values 174 in memory 170. In some examples, the length of each period is greater than one hour, such as a predetermined integer number of hours or days. In some examples, the period length is between eight hours and three days, such as one day.

Each of patient parameter values 174 may be the single value of a patient parameter determined during the period. In other examples, each of patient parameter values 174 is a representative value determined based on a plurality of values determined during the period. In some examples, patient parameter values 174 may include one or more means, medians, modes, sums, or other values determined based on a plurality of values of a patient parameter determined during the period.

The plurality of patient parameters may include one or more parameters determined based on the cardiac electrogram, such as one or more heart rate parameters, and/or one or more tachyarrhythmia episode parameters. Example heart rate parameters include average heart rate during the period, average daytime heart rate during the period, average nighttime heartrate during the period, and one or more measures of heart rate variability during the period. Example tachyarrhythmia episode parameters include the number, frequency and/or duration (total, mean, or median) of tachyarrhythmia episodes during the period, such as atrial tachycardia episodes, atrial fibrillation episodes, or non-sustained tachyarrhythmia (NST) episodes. NST episodes may be a series of short R-R intervals greater than an NST threshold number of short R-R intervals, but fewer than a number of intervals to detect (NID) for ventricular tachyarrhythmia. Another example patient parameter that processing circuitry 160 may determine based on the cardiac electrogram is the ventricular rate during atrial tachyarrhythmia, e.g., atrial fibrillation, which may be a mean or median value during the period.

Other patient parameters determined based on the cardiac electrogram include morphological features of the cardiac electrogram, such as QRS width or duration, QT interval length, T-wave amplitude, R-R interval length, an interval between a peak and the end of the T-wave, a ratio between the T-wave peak to end interval and the QT interval lengths, or T-wave alternan. The presence of T-wave alternan may be detected as a periodic (e.g., beat-to-beat) variation in the amplitude or morphology of the T-wave. A T-wave alternan patient parameter value 174 may be an indication of the presence, number, frequency, or duration (total, mean, or median) of T-wave alternan episodes. Other patient parameter values 174 based cardiac electrogram morphological interval lengths may be means or medians of a plurality of measurements made during the period, e.g., daily mean or median values.

The plurality of patient parameters may additionally or alternatively include at least one patient parameter indicative of edema, and processing circuitry 160 may determine values 174 of such patient parameters based on sensed thoracic impedance, as described above. In some examples, a patient parameter value 174 may be a maximum, minimum, mean, or median thoracic impedance value during a period. In some examples, a patient parameter value 174 may be a fluid index value during the period. Processing circuitry 160 may increment and decrement a fluid index value based on an accumulation of differences between a thoracic impedance value (or short-term average of impedance values) and a threshold determined based on a long-term average of thoracic impedance values.

The plurality of patient parameters may additionally or alternatively include at least one patient parameter indicative of patient activity, e.g., gross patient body movement or motion. In some examples, processing circuitry 160 determines a number of activity counts based on one or more accelerometer signals crossing exceeding one or more thresholds. A patient parameter value 174 during a period may be a total, mean, or median number of counts during the period.

The plurality of patient parameters may additionally or alternatively include at least one patient parameter indicative of cardiovascular pressure, and processing circuitry 160 may determine values 174 of such patient parameters based on generated pressure waveform, e.g., generated by a sensor 166 or pressure-sensing IMD 50, as described above. The patient parameter values 174 for the period may include a maximum, minimum, mean, or median of systolic pressure and/or diastolic pressure, e.g., pulmonary artery diastolic pressure.

The plurality of patient parameters may additionally or alternatively include at least one patient parameter determined based on patient respiration, and processing circuitry 160 may determine values 174 of such parameters based on a generated signal that varies based on respiration as described above, such as a signal that varies based on thoracic impedance. The patient parameter values 174 for the period may include a maximum, minimum, mean, or median of respiration rate, e.g., for a day, daytime, or nighttime. The patient parameter values 174 for the period may include an indication of the presence, a number, a frequency, or a duration (total, mean, or median) of respiration episodes, such as apneas or dyspneas.

Processing circuitry 160 may additionally or alternatively determine values 174 of one or more patient parameters based on a generated signal that varies based on sound or other vibrations, which may indicate heart sounds, coughing, or rales. Patient parameter values may include morphological measurements of the S1 and S2 heart sounds, the presence or frequency of occurrence of S3 and/or S4 heart sounds, or the presence, number, frequency, or duration (total, mean or media) of episodes or coughing or rales. Other patient parameter values 174 that processing circuitry 160 may additionally or alternatively periodically determine based on signals generated by sensors 166 include maximum, minimum, mean, or median values of blood flow, blood oxygen saturation, or temperature.

The plurality of patient parameters may additionally or alternatively include at least one patient parameter determined based on delivery of therapy to patient 14, e.g., by IMD 10. In some examples, a patient parameter value 174 for a period indicates an amount of cardiac pacing delivered to the patient during the period, such as a total duration or percentage of the period during which atrial pacing, ventricular pacing, and/or CRT was delivered.

In some examples, the plurality of patient parameter values 174 determined for each period includes: a percentage of the period during which IMD 10 delivered ventricular pacing to patient 14; a percentage of the period during which IMD 10 delivered atrial pacing to patient 14; an average daytime ventricular heart rate; an average nighttime ventricular heart rate; a frequency or duration of atrial tachycardia event, atrial fibrillation events, and/or NSTs during the period; a total number of patient activity counts during the period; a measure of heart rate variability during the period; a daily thoracic impedance value; and a fluid index value. In some examples, the plurality of patient parameter values 174 includes all or subset of the parameters included in Cardiac Compass® trends generated by IMDs available from Medtronic, plc, of Dublin Ireland. In some examples, the plurality of patient parameter values 174 additionally includes one or more cardiac electrogram morphology parameters.

The plurality of patient parameters may additionally or alternatively include at least one patient parameter determined or derived based on the shape or form of at least one of a sagittal axis signal, a vertical axis signal and a transverse axis signal as produced, generated or provided by the accelerometer(s) 166. In some examples, a patient parameter value(s) 174 is a quantified score associated with a Sit-To-Stand test. In some examples, a patient parameter value(s) 174 is at least one of: a rate of change metric(s) associated with a Sit-To-Stand test; a definite integral metric(s) associated with a Sit-To-Stand test; a length of time metric(s) associated with a Sit-To-Stand test; a peak amplitude metric (s) associated with a Sit-To-Stand test; a peak-peak amplitude metric(s) associated with a Sit-To-Stand test; an averaged patient-specific functional status parameter associated with a Sit-To-Stand test; a time occurrence of at least one inflection point associated with a Sit-To-Stand test; a symmetry characteristic(s) or metric(s) associated with a Sit-To-Stand test; a velocity metric(s) associated with a Sit-To-Stand test; a distance metric(s) associated with a Sit-To-Stand test; a kinetic energy metric(s) associated with a Sit-To-Stand test; a potential energy metric(s) associated with a Sit-To-Stand test; a derivative metric(s) associated with a Sit-To-Stand test; a metric(s) to distinguish a sit-to-stand movement from a stand-to-sit movement; identify a metric(s) to a stand-to-sit morphology; a metric(s) to identify sit-to-stand morphology. Still other examples are possible.

Processing circuitry 160 determines a difference metric 176 for each of the plurality patient parameters for the period. Processing circuitry 160 determines the difference metric 176 for each patient parameter based on a difference between a current value 174 of the patient parameter for the current period, and an immediately preceding value 174 of the patient parameter for the immediately preceding period. In some examples, processing circuitry 160 determines the difference metric 176 for each of the patient parameters according to the following equation:

$$V_{t,parm_n} = \text{Value}_{t-1} - \text{Value}_{t-2} \quad \text{(Eq. 1)}$$

In some examples, processing circuitry 160 determines the difference metric 176 for each of the plurality patient parameters for the period based on the difference between the current and preceding values, and a standard deviation (or other measure of variation) of values 174 of the patient parameter for N preceding periods. N is an integer constant, e.g., between 5 and 50, such as between 7 and 15 or, in one example, 15. In examples in which each period is a day, the N preceding periods may be N preceding days. Determining the difference metric based on the difference between the current and preceding values and a standard deviation or other measure of variation allow the difference metric to better represent the difference in the patient parameter during the current period rather than baseline variation of the patient parameter and/or noise. In some examples, processing circuitry 160 determines the difference metric 176 for each of the patient parameters according to the following equation:

$$V_{t,param_n} = \frac{\text{Value}_{t-1} - \text{Value}_{t-2}}{SD_t} \quad \text{(Eq. 2)}$$

Processing circuitry 160 determines a score 178 for the period based on the plurality of patient parameter-specific difference metrics 176 for the period. In some examples, processing circuitry 160 determines the score 178 for the period based on a sum of squares of the difference metrics 176 for the period or a sum of absolute values of the difference metrics 176. The difference metrics 176 may be positive or negative, and use of the sum of squares or absolute values may enable the score 178 to reflect the absolute magnitudes of change of the plurality of patient parameters during the period. In some examples, processing circuitry 160 determines the score 178 for the period using a sum of squares of difference metrics 176 according to the following equation, where n is the number of patient parameters for which difference metrics 176 are determined during the period (in this case 8):

$$\text{score}_t = \Sigma_{n=1}^{8} V_{t,parm_n}^2 \quad \text{(Eq. 3)}$$

In some examples, processing circuitry 160 applies coefficients or weights to one or more of difference metrics 176 when determining a score 178 for a period. The weights may be determined and/or adjusted empirically based on an analysis of the sensitivity and specificity of the score 178 for determining patient functional status based on accelerometer-generated data. The values of the weights may be adjusted over time, e.g., on a period-by-period or less frequent basis.

Processing circuitry 160 also determines a threshold 180 for the period based on scores 178 for N preceding periods, wherein N is the integer constant, e.g., 15. In some examples, processing circuitry 160 determines the threshold 180 based on a mean or median of the N preceding scores, e.g., by multiplying a median of the N scores and a coefficient. The coefficient may be, for example, between 1 and 3, and determined for a given patient 14 or patient population based on a receiver operator characteristic (ROC).

Communication circuitry 168 includes any suitable hardware, firmware, software or any combination thereof for communicating with another device, such as an external device 30 or another IMD or sensor. Under the control of processing circuitry 160, communication circuitry 168 may receive downlink telemetry from and send uplink telemetry to external device 30 or another device with the aid of an antenna, which may be internal and/or external. In some examples, communication circuitry 168 may communicate with a local external device, and processing circuitry 160 may communicate with a networked computing device via the local external device and a computer network, such as the Medtronic CareLink® Network developed by Medtronic, plc, of Dublin, Ireland.

A clinician or other user may retrieve data from IMD 10 using external device 30 or another local or networked computing device configured to communicate with processing circuitry 160 via communication circuitry 168. The clinician may also program parameters of IMD 10 using external device 30 or another local or networked computing device. In some examples, the clinician may select patient parameters used to quantify patient-specific functional status associated with a Sit-To-Stand test. In general, such parameters may include single data points (i.e., a single score that quantifies patient-specific functional status associated with a particular Sit-To-Stand test) or a sequence of data points that may be plotted as a trend over time.

Figure 8:
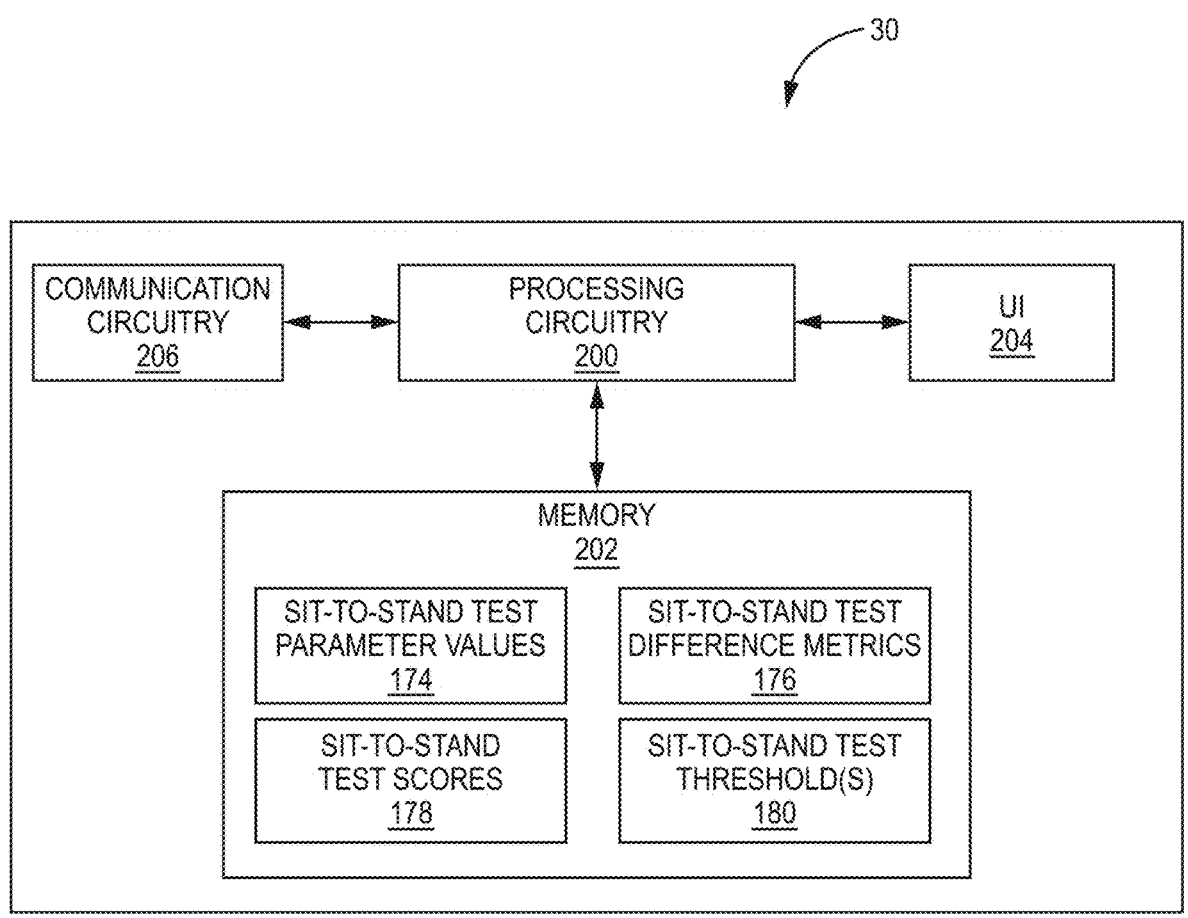
FIG. 8 is a functional block diagram illustrating an example configuration of an external device configured to communicate with one or more implantable medical devices.

FIG. 8 is a functional block diagram illustrating an example configuration of an external device 30 configured to communicate with one or more IMDs 10. In the example of FIG. 8, external device 30 includes processing circuitry 200, memory 202, user interface (UI) 204, and communication circuitry 206. External device 30 may correspond to any of external devices 30A-30C described with respect to FIGS. 1, 2, and 4A-5. External device 30 may be a dedicated hardware device with dedicated software for the programming and/or interrogation of an IMD 10. Alternatively, external device 30 may be an off-the-shelf computing device, e.g., a smartphone running a mobile application that enables external device 30 to program and/or interrogate IMD 10.

In some examples, a user uses external device 30 to select or program any of the values for operational parameters of IMD 10, e.g., for measuring or determining patient functional status based on accelerometer-generated data. In some examples, a user uses external device 30 to receive data collected by IMD 10, such as patient parameter values 174 or other operational and performance data of IMD 10. The user may also receive alerts provided by IMD 10 that indicate that an acute cardiac event, e.g., ventricular tachyarrhythmia, is predicted. The user may interact with external device 30 via UI 204, which may include a display to present a graphical user interface to a user, and a keypad or another mechanism (such as a touch sensitive screen) for receiving input from a user. External device 30 may communicate wirelessly with IMD 10 using communication circuitry 206, which may be configured for RF communication with communication circuitry 168 of IMD 10.

Processing circuitry 200 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 200 may include multiple components, such as any combination of one or more microprocessors, one or more DSPs, one or more ASICs, or one or more FPGAs, as well as other discrete or integrated logic circuitry, and/or analog circuitry.

Memory 202 may store program instructions, which may include one or more program modules, which are executable by processing circuitry 200. When executed by processing circuitry 200, such program instructions may cause processing circuitry 200 and external device 30 to provide the functionality ascribed to them herein. The program instructions may be embodied in software, firmware and/or RAMware. Memory 202 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In some examples, processing circuitry 200 of external device 30 may be configured to provide some or all of the functionality ascribed to processing circuitry 160 of IMD 10 herein. For example, processing circuitry 200 may receive physiological signals generated by one or more IMDs 10 and determine values 174 of each of a plurality of patient parameters during each of a plurality of periods, and/or may receive patient parameter values 174 for the plurality of periods from one or more IMDs 10. Processing circuitry 200 may determine metrics 176, scores 178, and thresholds 180 based on the patient parameter values 174 in the manner described above with respect to processing circuitry 160 of IMD 10 for determining patient functional status based on accelerometer-generated data.

Figure 9:
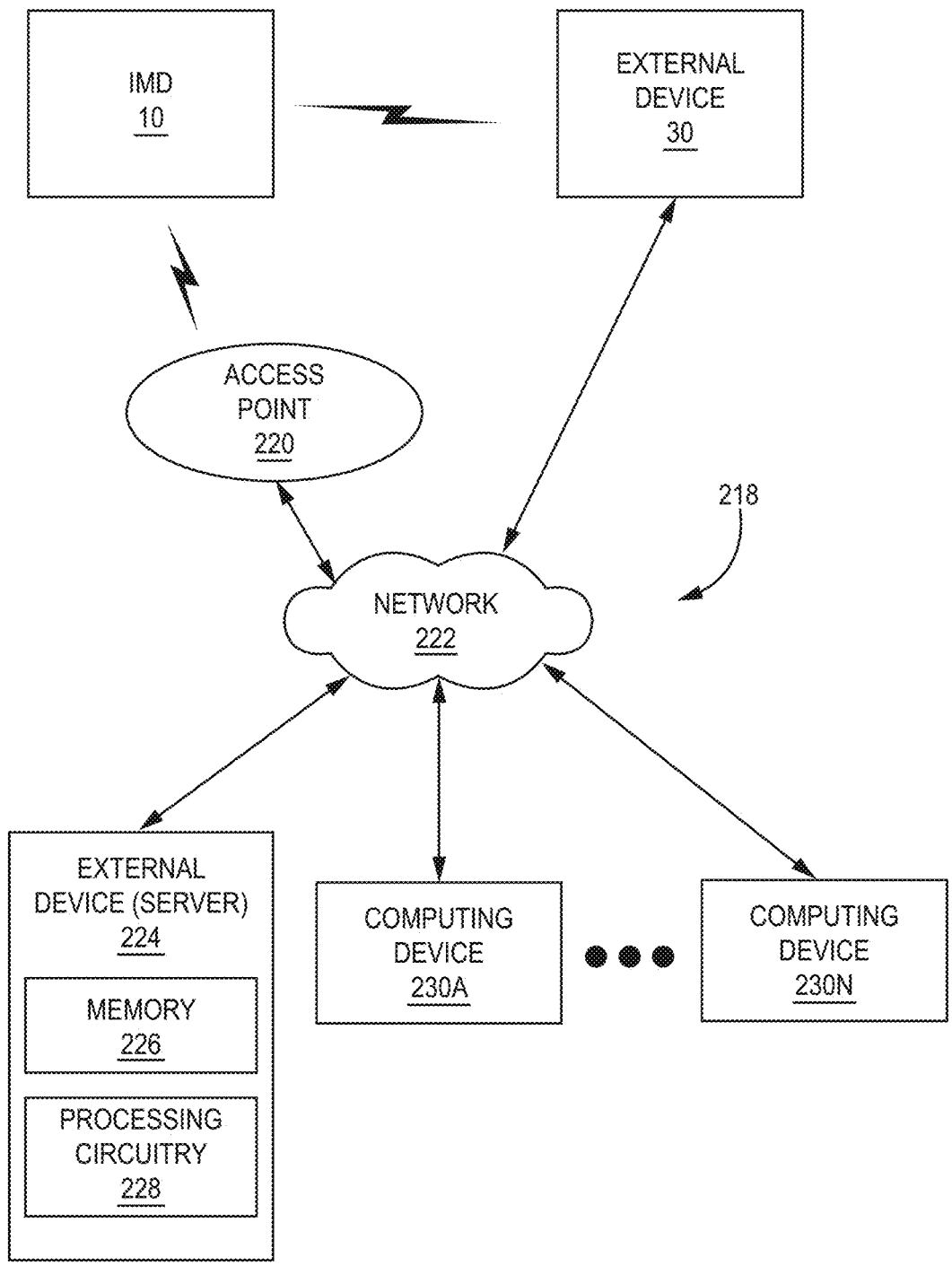
FIG. 9 is a functional block diagram illustrating an example system that includes remote computing devices, such as a server and one or more other computing devices, that are connected to an implantable medical device and/or external device via a network.

FIG. 9 is a functional block diagram illustrating an example system that includes external computing devices, such as a server 224 and one or more other computing devices 230A-230N, that are coupled to IMD 10 and external device 30 via a network 222. In this example, IMD 10 may use its communication module 168 to, e.g., at different times and/or in different locations or settings, communicate with external device 30 via a first wireless connection, and to communication with an access point 220 via a second wireless connection. In the example of FIG. 9, access point 220, external device 30, server 224, and computing devices 230A-230N are interconnected, and able to communicate with each other, through network 222.

Access point 220 may comprise a device that connects to network 222 via any of a variety of connections, such as telephone dial-up, digital subscriber line (DSL), or cable modem connections. In other examples, access point 220 may be coupled to network 222 through different forms of connections, including wired or wireless connections. In some examples, access point 220 may be co-located with patient 14. Access point 220 may interrogate IMD 10, e.g., periodically or in response to a command from patient 14 or network 222, to retrieve physiological signals, patient parameter values 174, difference metrics 176, scores 178, thresholds 180, alerts of acute cardiac events, and/or other operational or patient data from IMD 10. Access point 220 may provide the retrieved data to server 224 via network 222.

In some cases, server 224 may be configured to provide a secure storage site for data that has been collected from IMD 10 and/or external device 30. In some cases, server 224 may assemble data in web pages or other documents for viewing by trained professionals, such as clinicians, via computing devices 230A-230N. The illustrated system of FIG. 9 may be implemented, in some aspects, with general network technology and functionality similar to that provided by the Medtronic CareLink® Network developed by Medtronic plc, of Dublin, Ireland.

In some examples, one or more of access point 220, server 224, or computing devices 230 may be configured to perform, e.g., may include processing circuitry configured to perform, some or all of the techniques described herein, e.g., with respect to processing circuitry 160 of IMD 10 and processing circuitry 200 of external device 30, relating to determining patient functional status based on accelerometer-generated data. In the example of FIG. 9, server 224 includes a memory 226 to store signals or patient parameter values 174 received from IMD 10 and/or external device 30, and processing circuitry 228, which may be configured to provide some or all of the functionality ascribed to processing circuitry 160 of IMD 10 and processing circuitry 200 of external device 30 herein. For example, processing circuitry 228 may determine values 174 of each of a plurality of patient parameters during each of a plurality of periods, and/or may receive patient parameter values 174 for the plurality of periods from one or more IMDs 10. Processing circuitry 228 may determine metrics 176, scores 178, and thresholds 180 based on the patient parameter values 174 in the manner described above with respect to processing circuitry 160 of IMD 10 for determining patient functional status based on accelerometer-generated data.

As mentioned above, a medical device system according to certain features or aspects of this disclosure includes accelerometer circuitry configured to generate a number of signals including a sagittal (frontal) axis signal, as well as processing circuitry configured to calculate a patient-specific functional status parameter associated with a Sit-To-Stand test from the sagittal axis signal. Such an implementation may, among other things, provide an objective measure of change (or not) in well-being to help guide therapies, because a patient-specific functional status parameter associated with a Sit-To-Stand test can help determine whether health is improving, declining, or stable.

Figure 10:
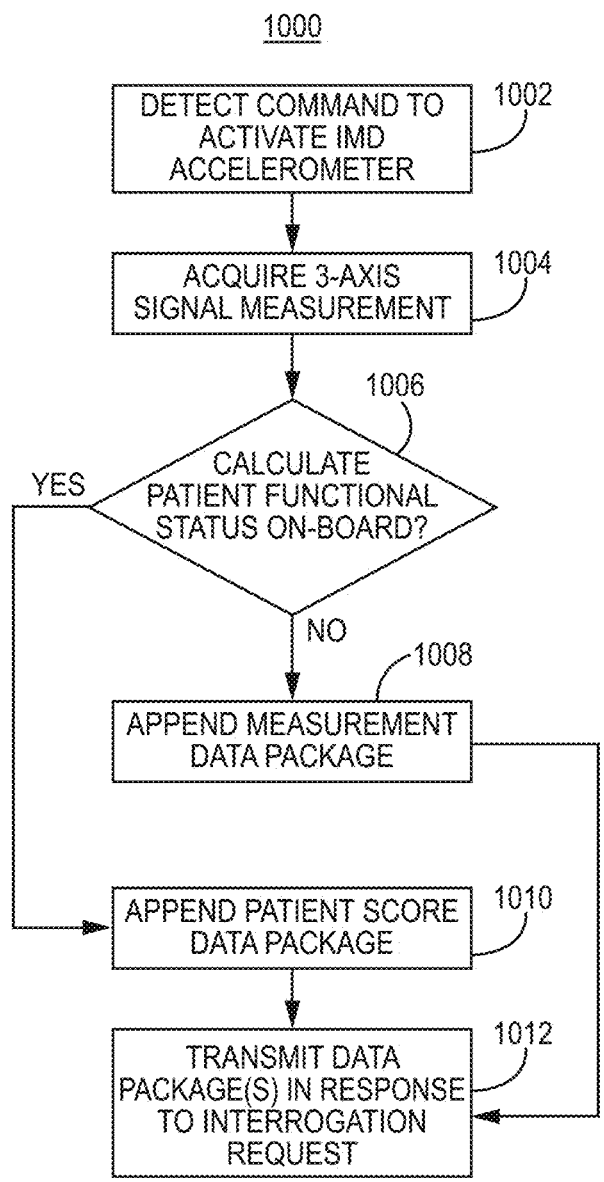
FIG. 10 is a flowchart illustrating a first example method for determining patient functional status based on accelerometer-generated data in accordance with the disclosure.

FIG. 10 is a flowchart illustrating a first example method 1000 for determining patient functional status based on accelerometer-generated data in accordance with the disclosure. Method 1000 may be implemented by any one of the implantable medical devices discussed above in connection with FIGS. 1-9, because each one of the same is configured to include at least one accelerometer (i.e., accelerometer circuitry), as well as communication and processing circuitry (see FIG. 7 and corresponding description) to facilitate determining patient functional status based on accelerometer-generated data. For example, and with reference to ICM 10B of FIG. 2, a command may be detected (1002) to activate or power-on an on-board accelerometer, and then a three-axis accelerometer signal measurement may be acquired (1004) over a finite interval of time. In other embodiments, the three-axis accelerometer measurement by be continuously monitored, and then a sit-to-stand transition may be identified based on the three-axis accelerometer. The three-axis accelerometer signal measurement may correspond to a sagittal axis signal, a vertical axis signal and a transverse axis signal each acquired over a common time window. Next, a patient-specific functional status parameter associated with a Sit-To-Stand test may be calculated from at least one of the sagittal axis signal, the vertical axis signal and the transverse axis signal.

In practice, the patient-specific functional status parameter may be calculated by the ICM 10B, then appended to a historical dataset of like status parameters, each uniquely identified by a timestamp and organized as a list, and then transmitted alone or together, with at least one status parameter in the historical dataset, to an external computing device or system for subsequent processing (branch 1006, 1010, 1012). The transmission may not necessarily be in response to a request however. For example, a transmission may occur automatically whenever a network connection becomes available, and/or at a particular time of day based upon a predefined schedule. Alternatively, raw data associated with each one of the sagittal axis signal, the vertical axis signal and the transverse axis signal acquired over the common time window may be stored, possibly in a modified form (e.g., compressed or encoded), and then transmitted alone or together with other like data to the at least one external computing device or system for subsequent processing (branch 1006, 1008, 1012). Such an implementation may be beneficial and/or advantageous in many respects.

For example, patient functional status can help determine whether health is improving, declining, or relatively steady. The 6 minute walk test (6MWT) is a standard for measuring patient-specific functional status. There may be a correlation in diagnostic benefit between the 6MWT and a Sit-To-Stand test (SST) for pulmonary disease patients that measures the time to perform multiple Sit-To-Stand-to-sit movements. The main component of a SST that takes the most effort for a patient typically is time-to-stand-up. Method 100 leverages at least the sagittal (frontal) axis of a 3D accelerometer to identify when a person stands up, and measurements are taken on the signal during the standing up period to assess patient functional status. As discussed in further detail below, a number of calculations may be made and then an SST measure may be produced that would provide clinical meaning.

Figure 11:
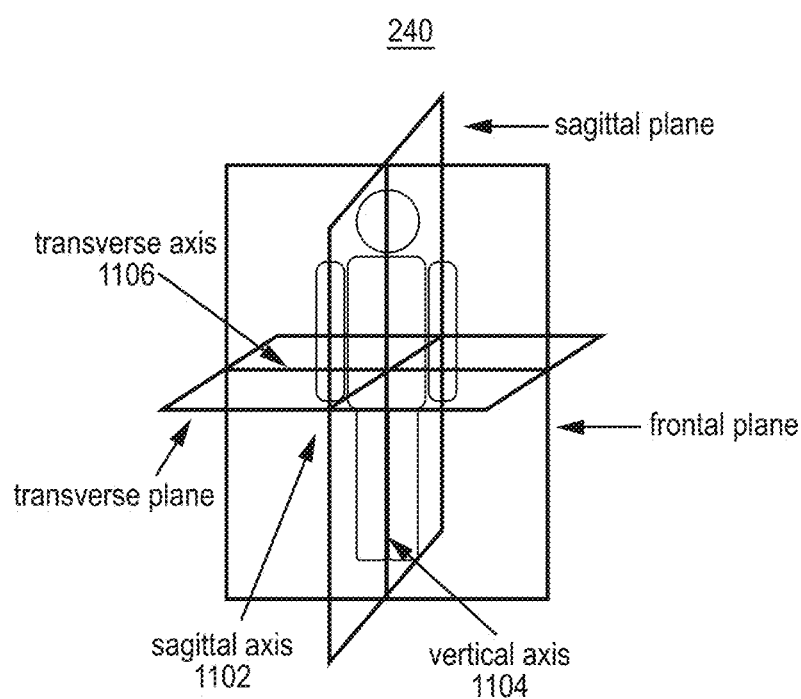
FIG. 11 is a conceptual diagram illustrating sagittal, vertical and transverse axes in a three-dimensional coordinate system.

FIG. 11 is a conceptual diagram 1100 illustrating a sagittal axis 1102, a vertical axis 1104 and transverse axis 1106 in a three-dimensional coordinate system.

Figure 12:
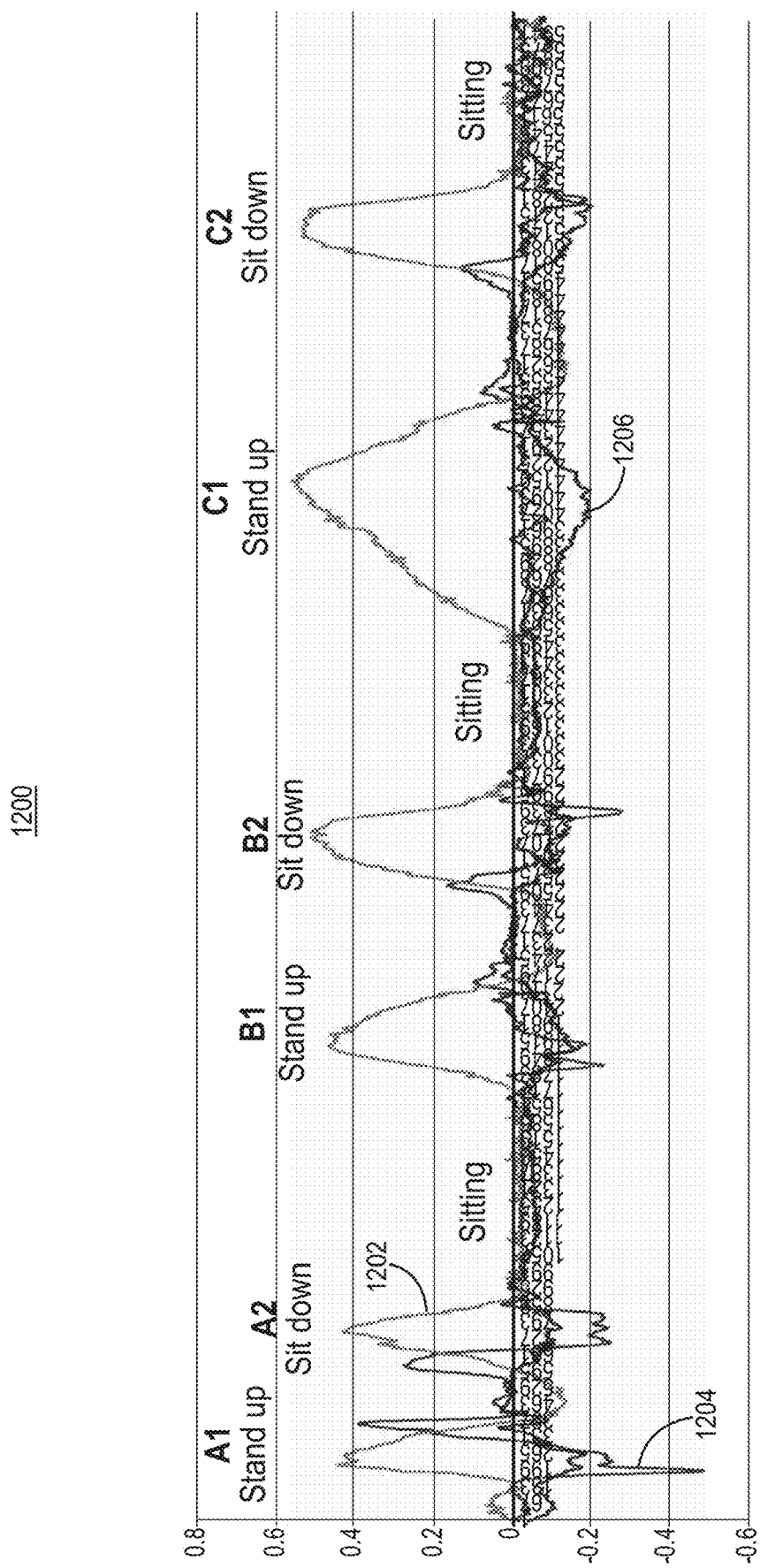
FIG. 12 is a plot illustrating sagittal, vertical and transverse axis signals produced by an accelerometer during a series of sit-stand and stand-sit movements.

FIG. 12 is a plot 1200 illustrating a sagittal axis signal 1202, a vertical axis signal 1204, and transverse axis signal 1206 produced by an accelerometer (see e.g., FIG. 7, element 166) during a series of sit-stand and stand-sit movements labeled A1-A2, B1-B2 and C1-C2, respectively. The sagittal axis signal 1202 corresponds to the trace or trend that exhibits the largest amplitude variations primarily on the (+) side of the y-axis (arbitrary units) across each one of A1-A2, B1-B2 and C1-C2. The vertical axis signal 1204 corresponds to the trace or trend that exhibits moderate amplitude variations on the (+) side and the (−) side of the y-axis across each one of A1-A2, B1-B2 and C1-C2. The transverse axis signal 1206 corresponds to the trace or trend that exhibits amplitude variations primarily on the (−) side of the y-axis across each one of A1-A2, B1-B2 and C1-C2, exhibits a number of zero-crossings that is less than a number of zero-crossings of the vertical axis signal 1204.

Figure 13:
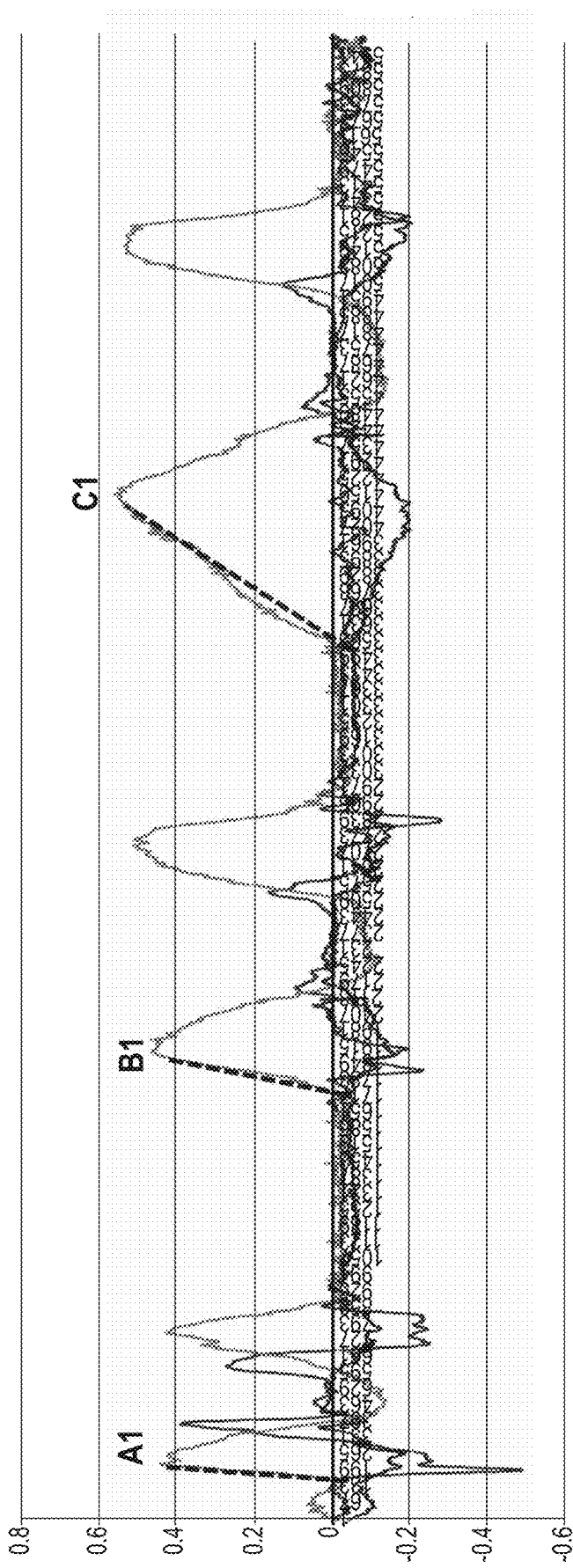
FIG. 13 is a plot illustrating the slopes of segments of the sagittal axis signal of FIG. 12.

FIG. 13 is a plot 1300 illustrating the slope of a segment of the sagittal axis signal 1202 of FIG. 12. More specifically, the slope of a segment corresponding to stand-up movement A1 is illustrated together with a representation of the area-under-curve taken over a time interval corresponding to an entirety of the stand-up movement A1, collectively "S1, I1" in FIG. 13. Further, the slope of a segment corresponding to stand-up movement B1 is illustrated together with a representation of the area-under-curve taken over a time interval corresponding to an entirety of the stand-up movement B1, collectively "S2, I2" in FIG. 13. Still further, the slope of a segment corresponding to stand-up movement C1 is illustrated together with a representation of the area-under-curve taken over a time interval corresponding to an entirety of the stand-up movement C1, collectively "S3, I3" in FIG. 13. As understood from the data, |S1|>|S2|>|S2|, and |I1|<|I2|<|I3|, indicating presence of increasing patient fatigue over the duration of the series of sit-stand and stand-sit movements. Accordingly, it is contemplated that the sagittal axis signal 1202 can be leveraged for measuring or determining patient functional status, as part of a SST performance test for example. Other features of the sagittal axis signal 1202 indicate patient fatigue as well.

Figure 14:
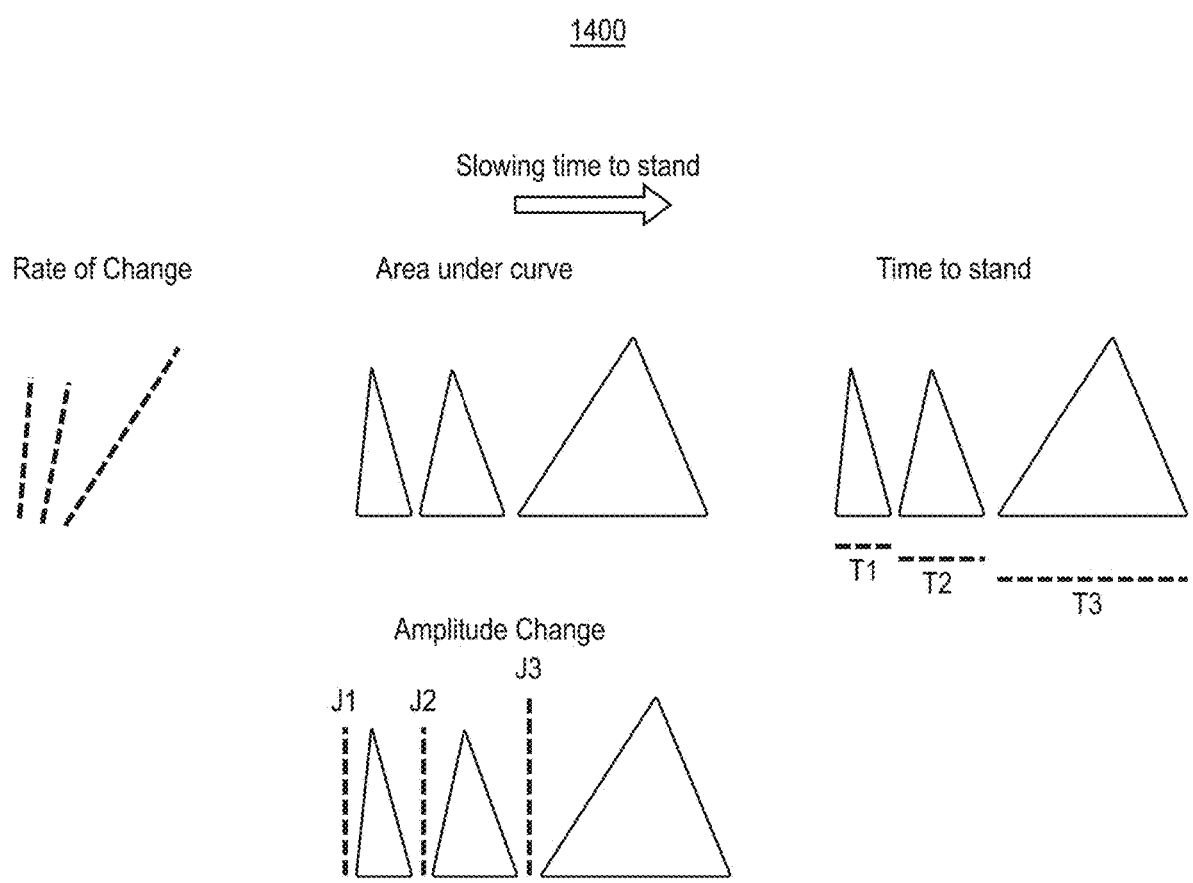
FIG. 14 is a conceptual diagram illustrating a change in several characteristics of the sagittal axis signal of FIG. 12 over the series of sit-stand and stand-sit movements.

FIG. 14 is a conceptual diagram 1400 illustrating a change in several characteristic of the sagittal axis signal 1202 of FIG. 12 over the series of sit-stand and stand-sit movements. More specifically, slope (rate of change) decreases over stand-up movements A1-C1 (see FIG. 12), area-under-curve (definite integral) increases over stand-up movements A1-C1, time to stand (T1-T3) increases over stand-up movements A1-C1, and amplitude (J1-J3) varies over stand-up movements A1-C1. Patient fatigue over the duration of the series of sit-stand and stand-sit movements is indicated due to such trends. Accordingly, it is contemplated that the sagittal axis signal 1202 can be leveraged for measuring or determining patient functional status, as part of a SST performance test for example. This is because 3D accelerometers in the ICM 10B, for example, which is implanted in the chest, and are relatively stationary over the lifetime of the implant. The stationary chest location presents an opportunity to monitor changes in the upper body that occur during various activities. As a person gets in and out of a chair for example the upper body has a reproducible motion (similar to a "bowing" motion) that may be identified with signals produced by the accelerometers. Accordingly, an algorithm may be developed for determining patient functional status based on at least the sagittal axis signal 1202.

Figure 15:
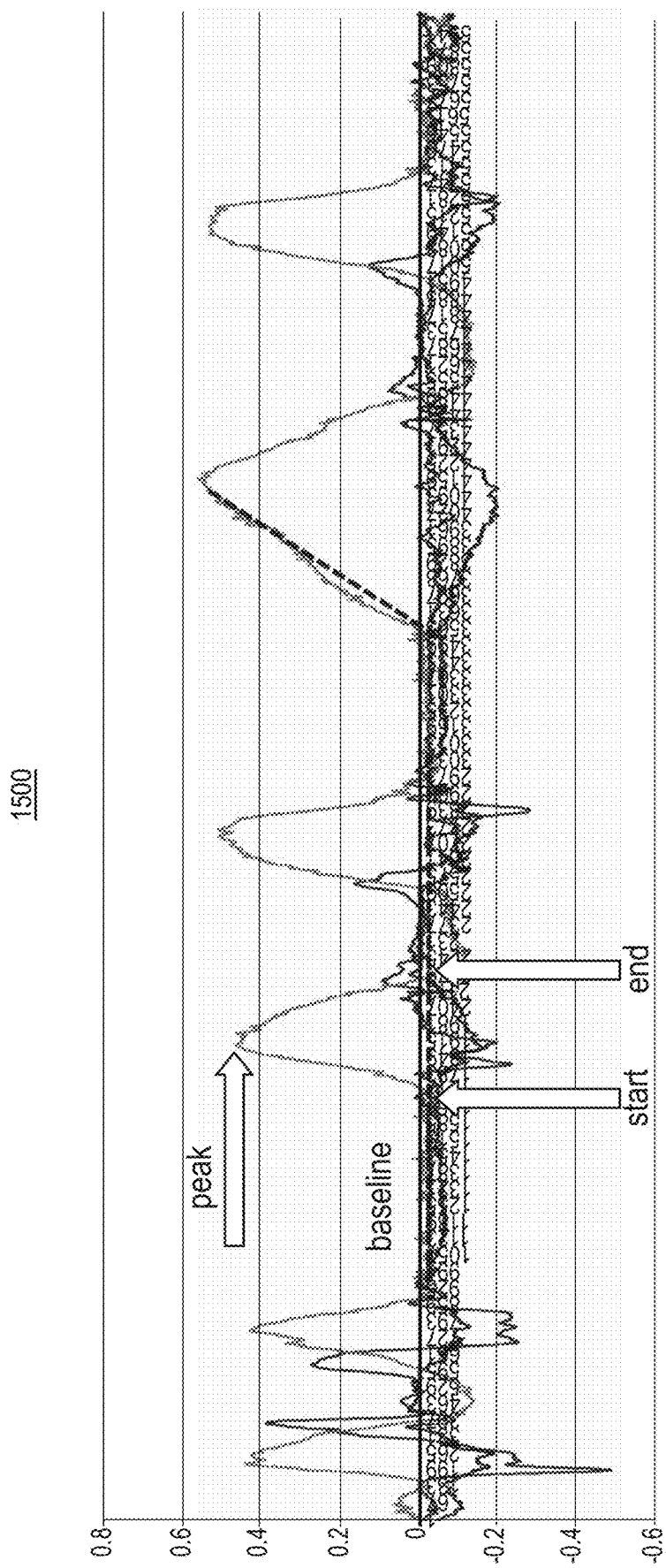
FIG. 15 is a plot illustrating several characteristic of the sagittal axis signal of FIG. 12.
Figure 16:
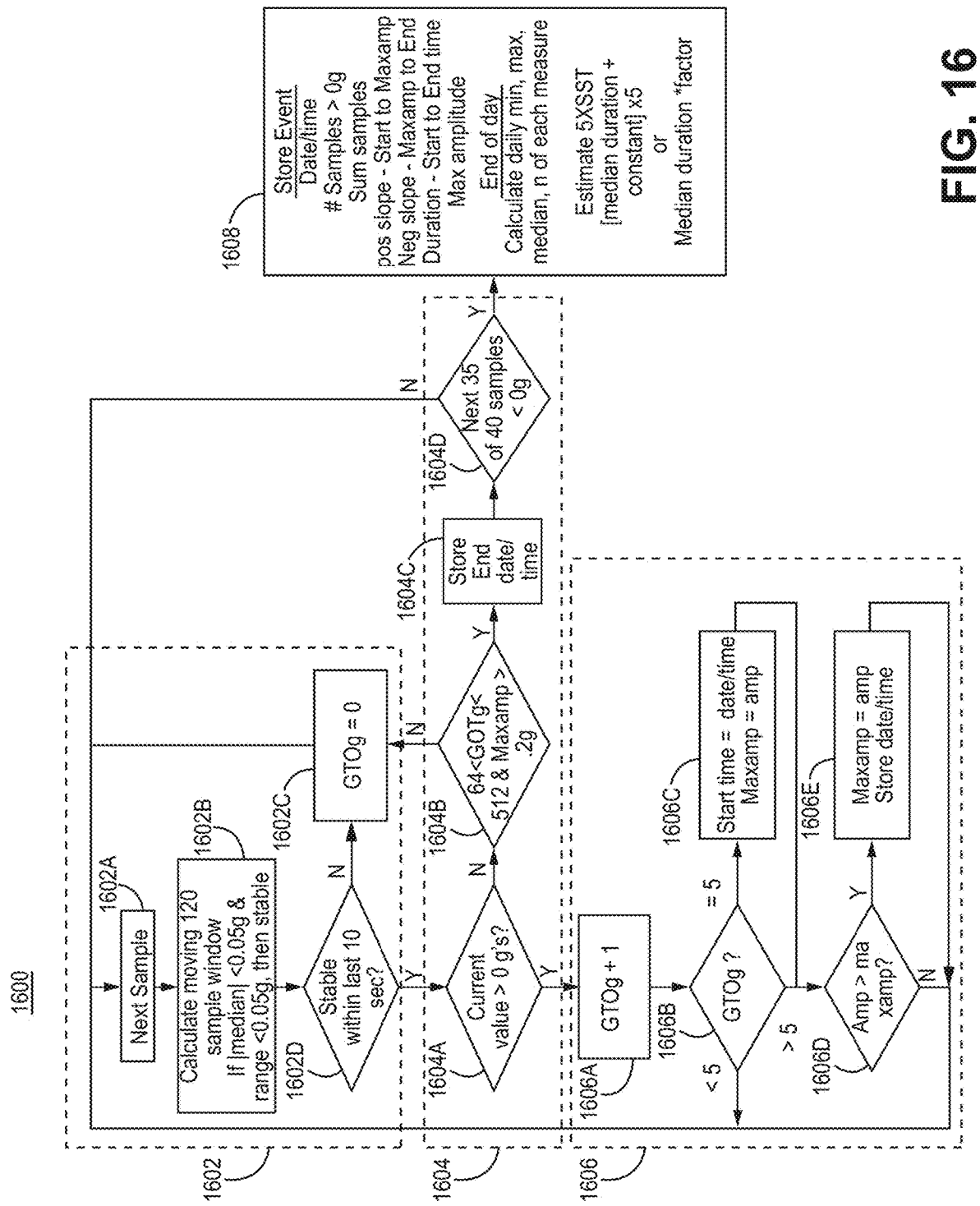
FIG. 16 is a flowchart illustrating a second example method for determining patient functional status based on accelerometer-generated data in accordance with the disclosure.

For example, FIG. 15 is a plot 1500 illustrating several characteristic of the sagittal axis signal of FIG. 12. And, FIG. 16 is a flowchart illustrating a second example method 1600 for determining patient functional status based on accelerometer-generated data in accordance with the disclosure. The method 1600 of FIG. 16 is also an example of how to detect sit-to-stand and stand-to-sit movements, and may be performed by any processing circuitry and/or IMD of any of medical device system described throughout.

With reference to FIGS. 15-16, an example algorithm may include:

Identify baseline (FIG. 15 "baseline"; FIG. 16 "loop 1602" where "GTOg=0" assigns a value of a current sample of the sagittal axis signal 1202 to value "0") by:

determining whether the current sample of the sagittal axis signal 1202 is within a certain number of units (e.g., 0.1 g) of baseline (e.g., 0 g), or another threshold different than baseline if determined applicable, for at least a certain number (e.g., 15) of seconds; as an alternative, since the waveform shape associated with sitting and the waveform shape associated with standing are similar, activity/steps before and after the shape may help differentiate the two, e.g., the waveform will have little to no variation prior to a standing movement and increased variation following completion of the standing movement, and an opposite effect will be visible in the sagittal axis signal over a stand-to-sit movement.

Identify start and end of standing up (FIG. 15 "start/end"; FIG. 16 "loop 1604") by:
  determining whether the amplitude of the sagittal axis signal 1202 amplitude increases over a threshold (e.g. 0.2 g) and decreases to less than the baseline within a certain time period (e.g. within 0.5 s-5 s).

Determine standing up characteristics (FIG. 16 "loop 1606" which searches for peak values in the signal and "element 1608") by:
  analyzing the sagittal axis signal 1202 from start to end of a particular time interval inclusive;
  calculating positive onset slope and following negative slope;
  calculating time to stand from start to end of stand movement (i.e., from sitting to full upright standing position);
  summing number of samples from slope increase to returning to below baseline;
  calculating peak amplitude;
  calculating number of events;
  storing date/time of each stand up with the standing up characteristic;
  calculating daily min, max, median values of any collected parameter;
  calculating estimated 5× Sit-To-Stand Test (5×SST) score=[Daily median of time to stand+constant sit time (e.g. 1 sec)]×5; in some instances, assume time to sit is fairly constant due the work of gravity; other examples are possible where the score may be calculated at any particular time or interval over any particular number of sit-to-stand movements Additionally, or alternatively, the example algorithm may leverage the following features:
  Symmetry: in order to stand the chest will lean forward then return to upright orientation; the symmetry between leaning forward versus return to upright might correlate with health based on a determined waveform shape;
  First integral of the sagittal axis signal: integration of acceleration is the velocity (v) therefore this feature tells the (instantaneous or average) velocity when a patient sits or stands;
  Second integral of the sagittal axis signal: integration of velocity is the distance, therefore this feature tells how far a patient leaned forward in order to stand up or sit, revealing at least balance capability;
  Kinetic energy. by assuming or measuring upper body mass (m) kinetic energy follows as $mv^2/2$, which quantifies or estimates how much energy is expended during sit or stand movements;
  Potential energy: this feature may require an acceleration sensor in feet to head direction which would enable us to calculate the potential energy=mgh, g is gravity. Alternatively, height, h, may be calculated from reference=0 (e.g., sitting position) to height=h as derived from a vertical axis signal (see below discussion) may be used. The energy transition between kinetic energy and potential energy may reveals health. For example, in a movement, a patient may spend 200 joules of kinetic energy to stand up and acquired 150 joules of potential energy. The ratio of 150/200 would be lowered when sick;
  First derivative; derivative of acceleration is known as the jerk, which reveals sudden movement, such as sudden drops that occur in heart failure patients during seating down;
  Max, min, difference, time evolution and other weighted functional combination of features above.

Figure 17:
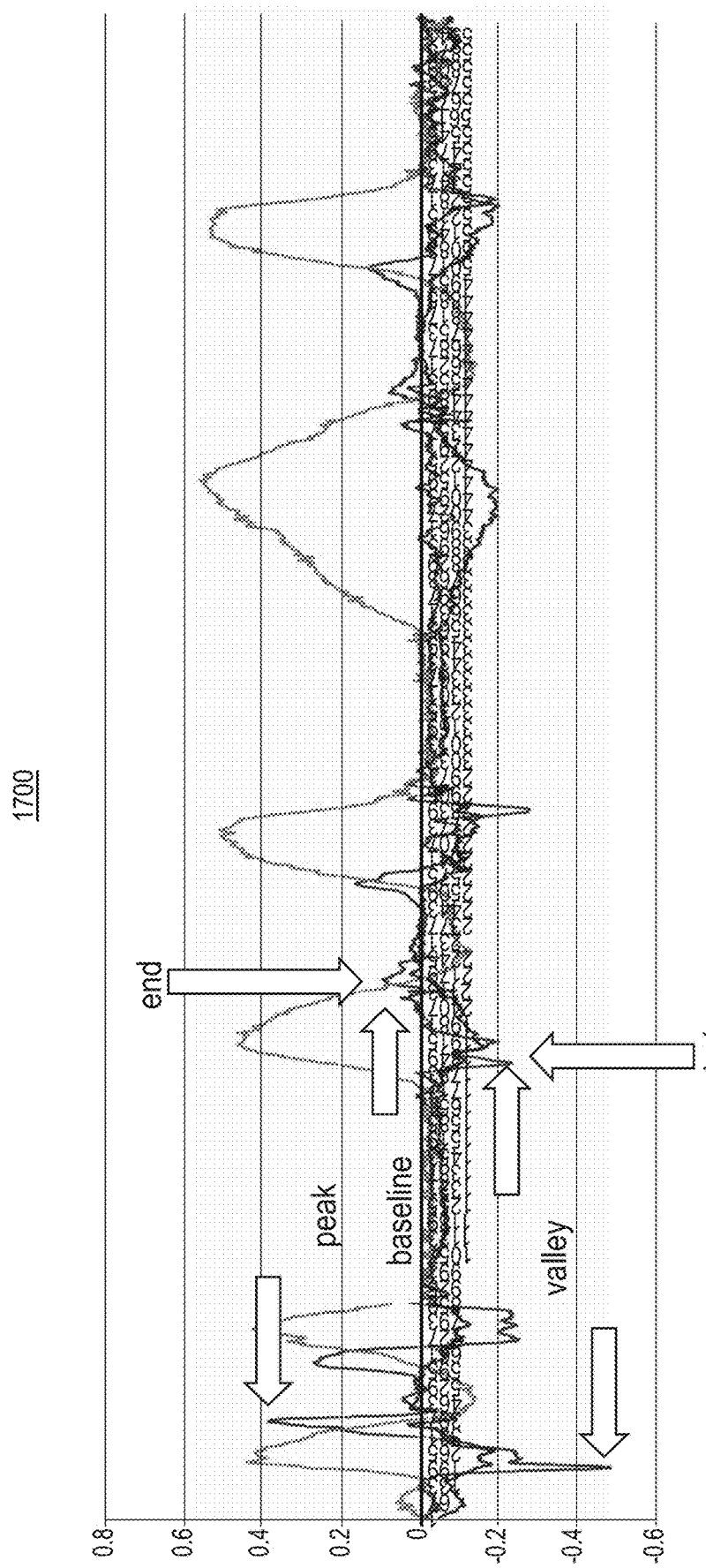
FIG. 17 is a plot illustrating characteristics of the vertical axis signal of FIG. 12.
Figure 18:
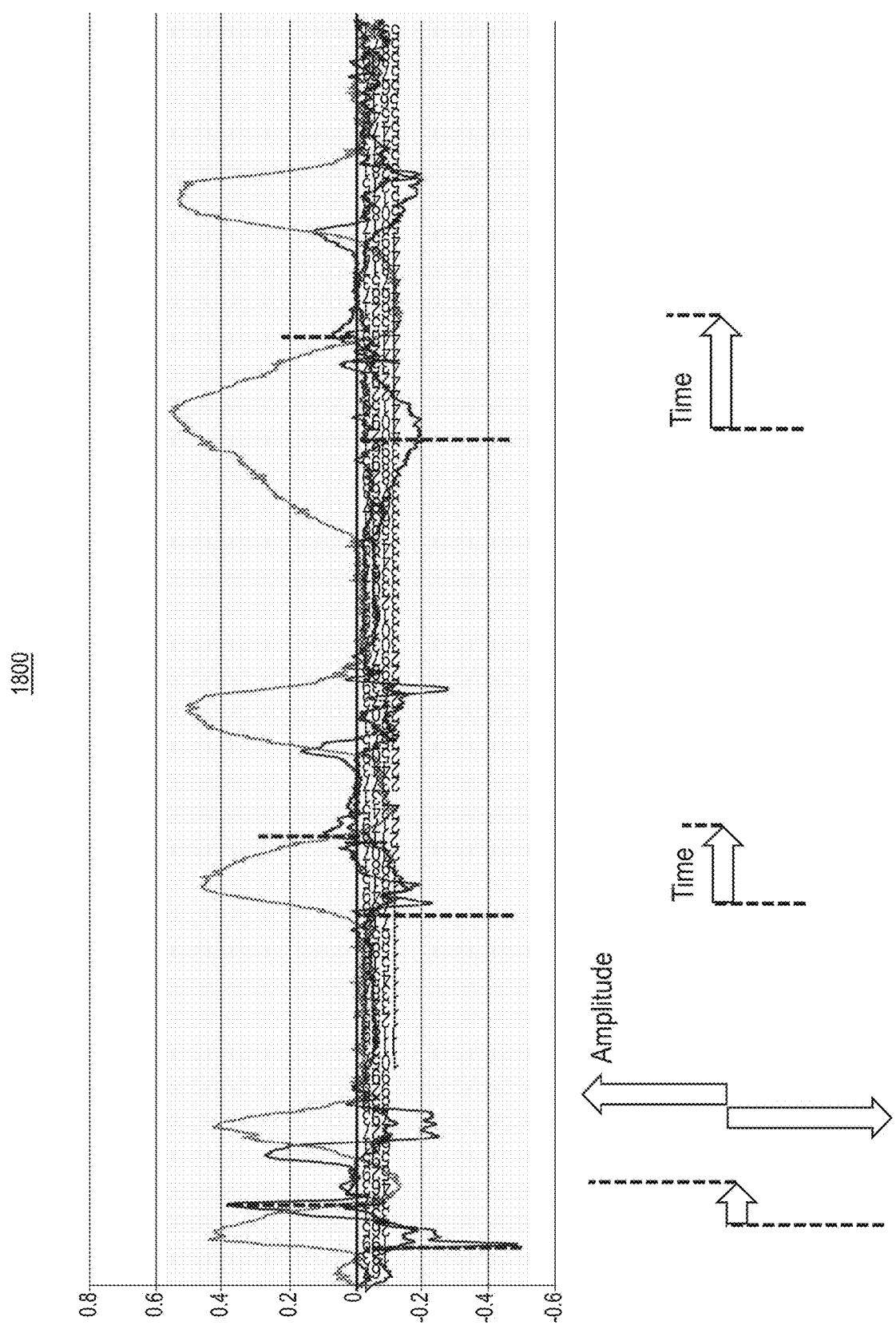
FIG. 18 is a plot illustrating characteristics of the vertical axis signal of FIG. 17.
Figure 19:
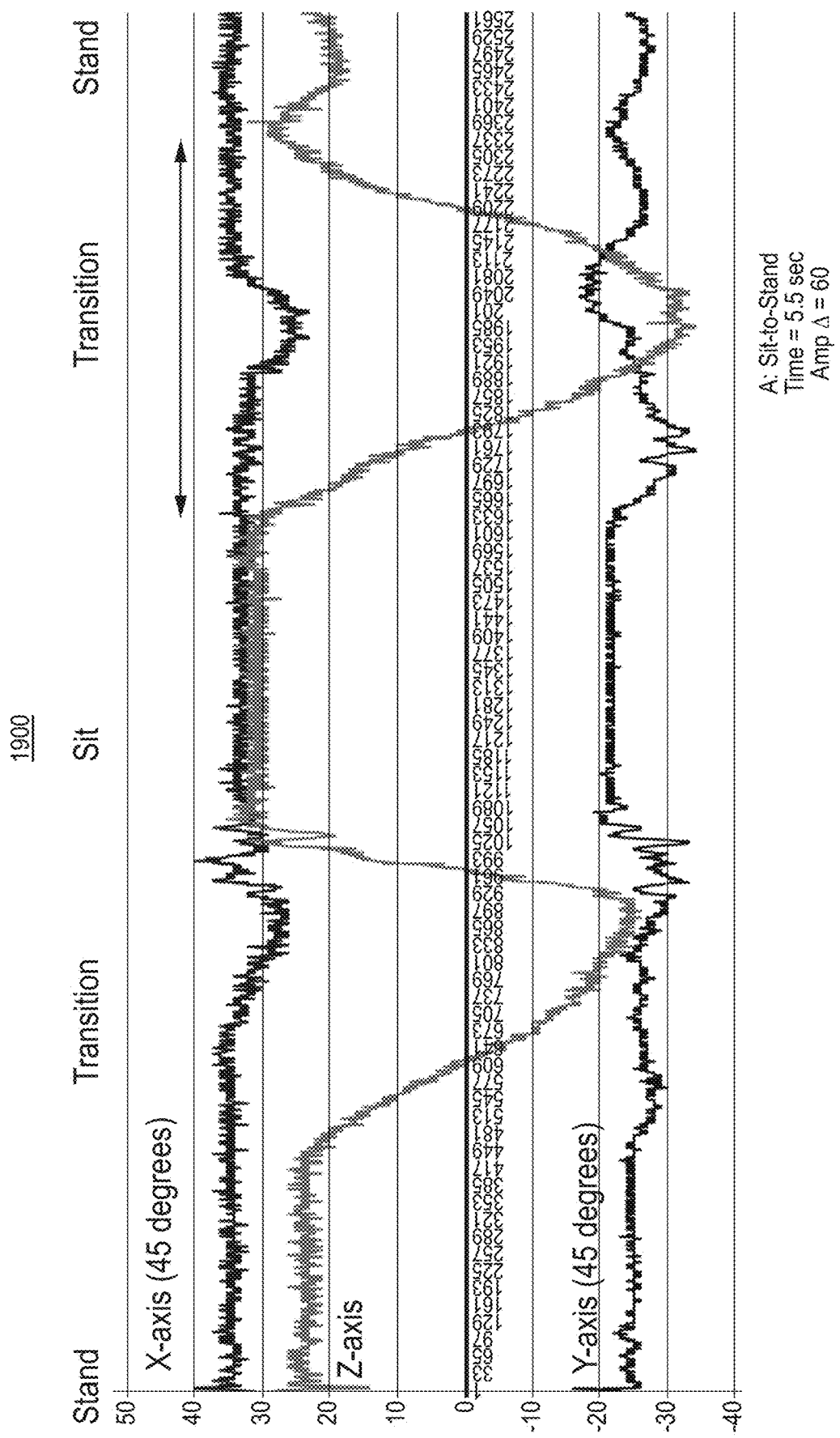
FIGS. 19-28 each is a plot of a series of plots illustrating sagittal, vertical and transverse axis signals produced by an accelerometer during at least one sit-stand movement.
Figure 20:
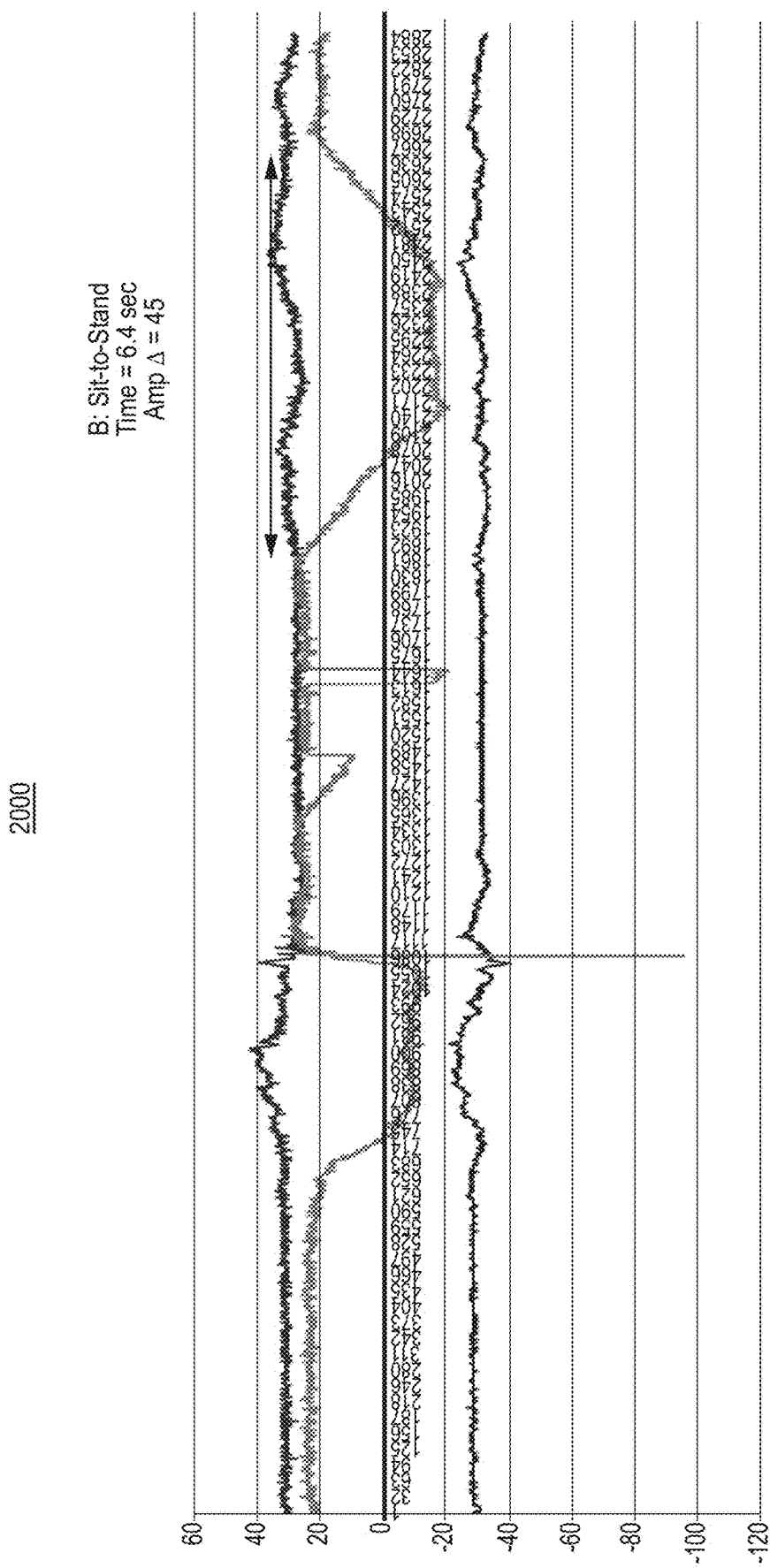
Figure 21:
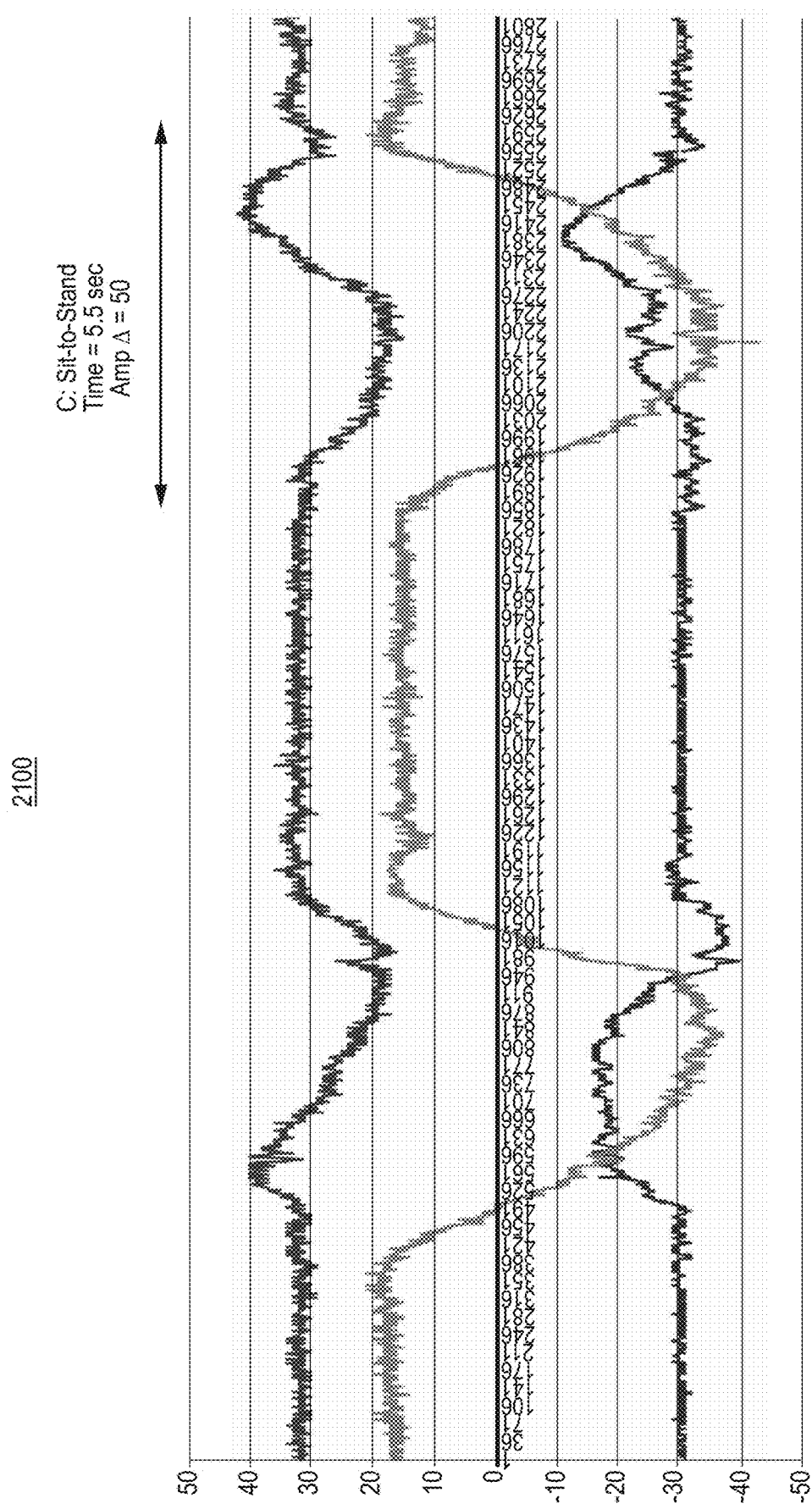
Figure 22:
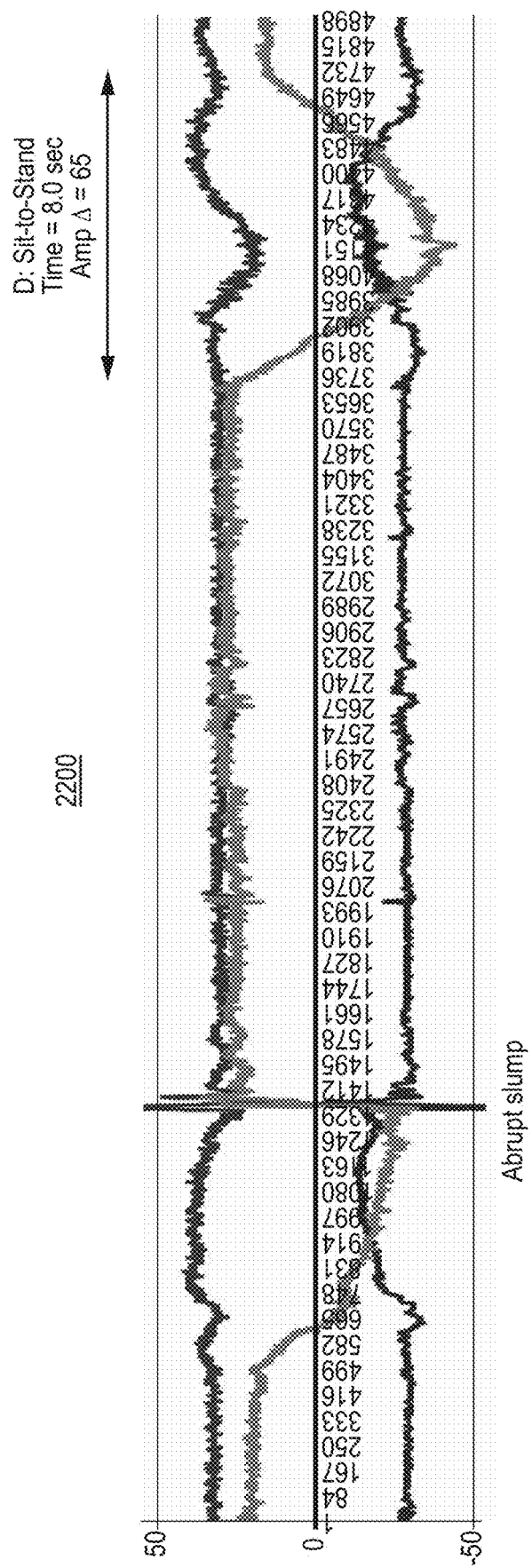
Figure 23:
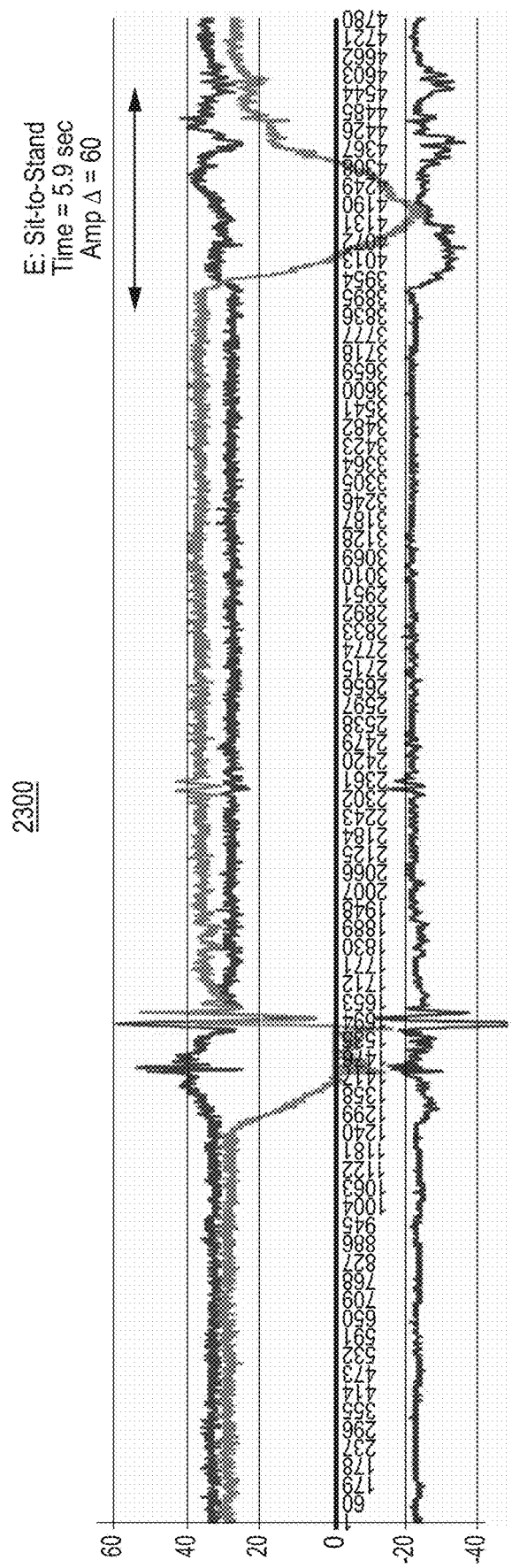
Figure 24:
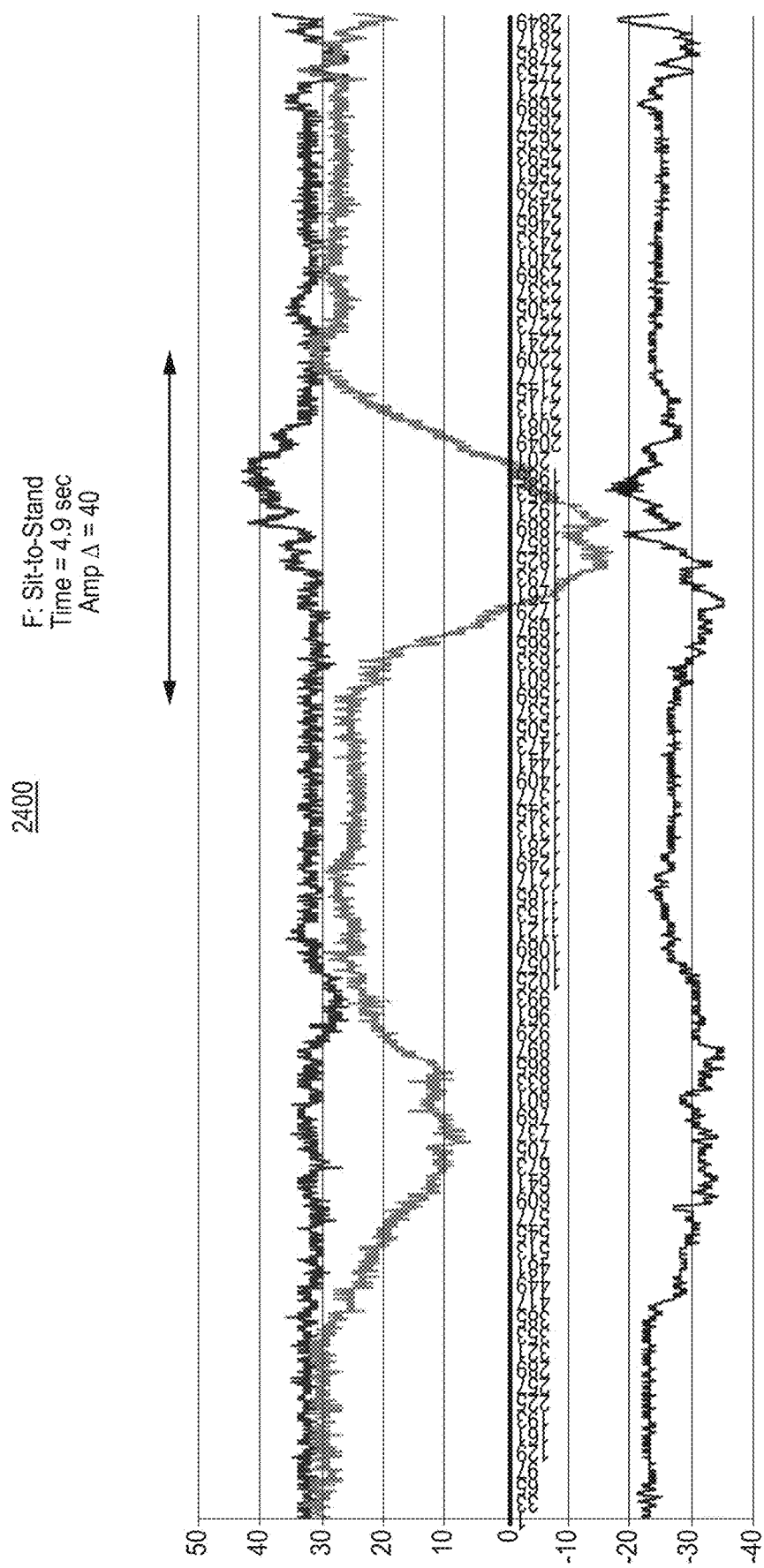
Figure 25:
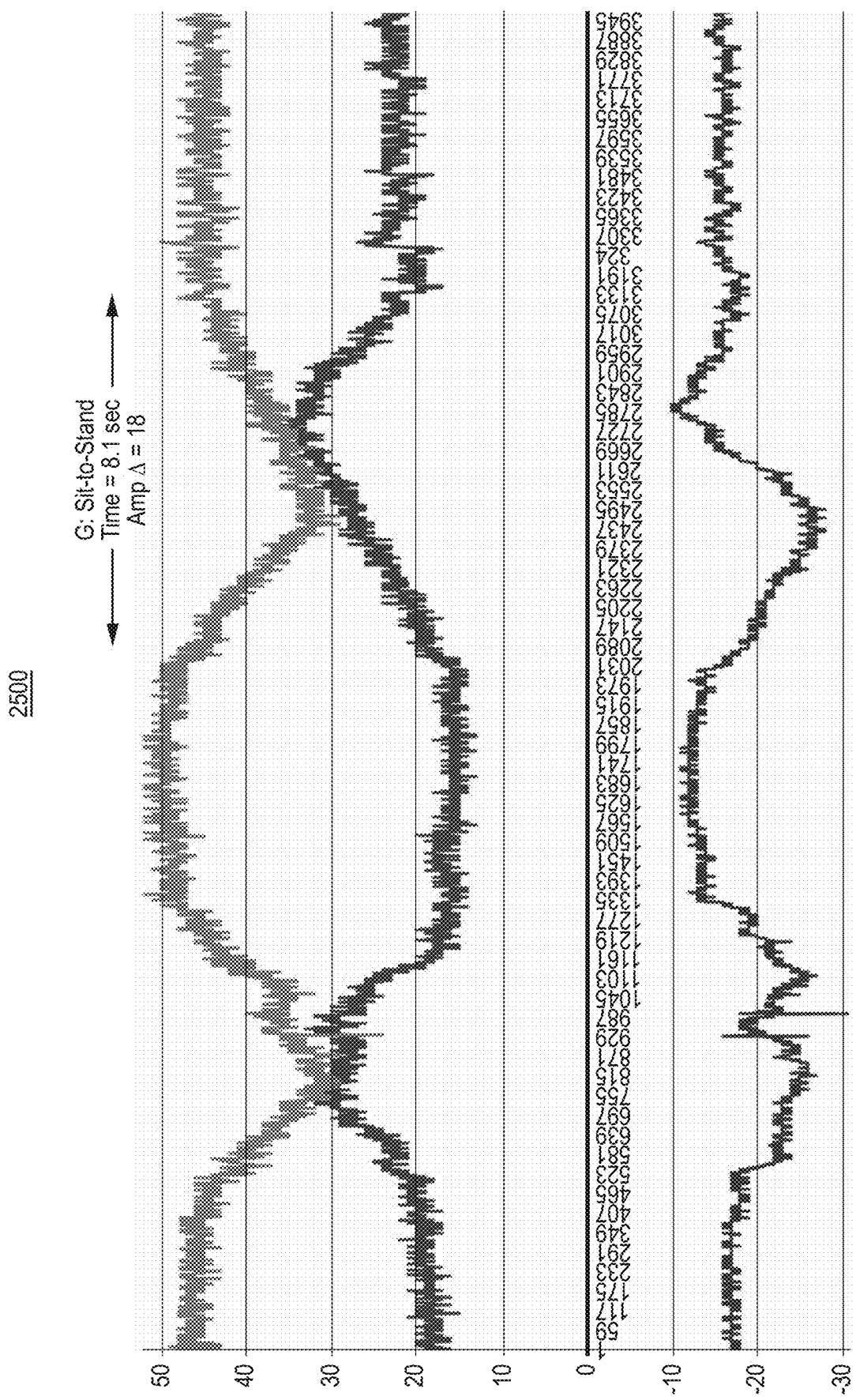
Figure 26:
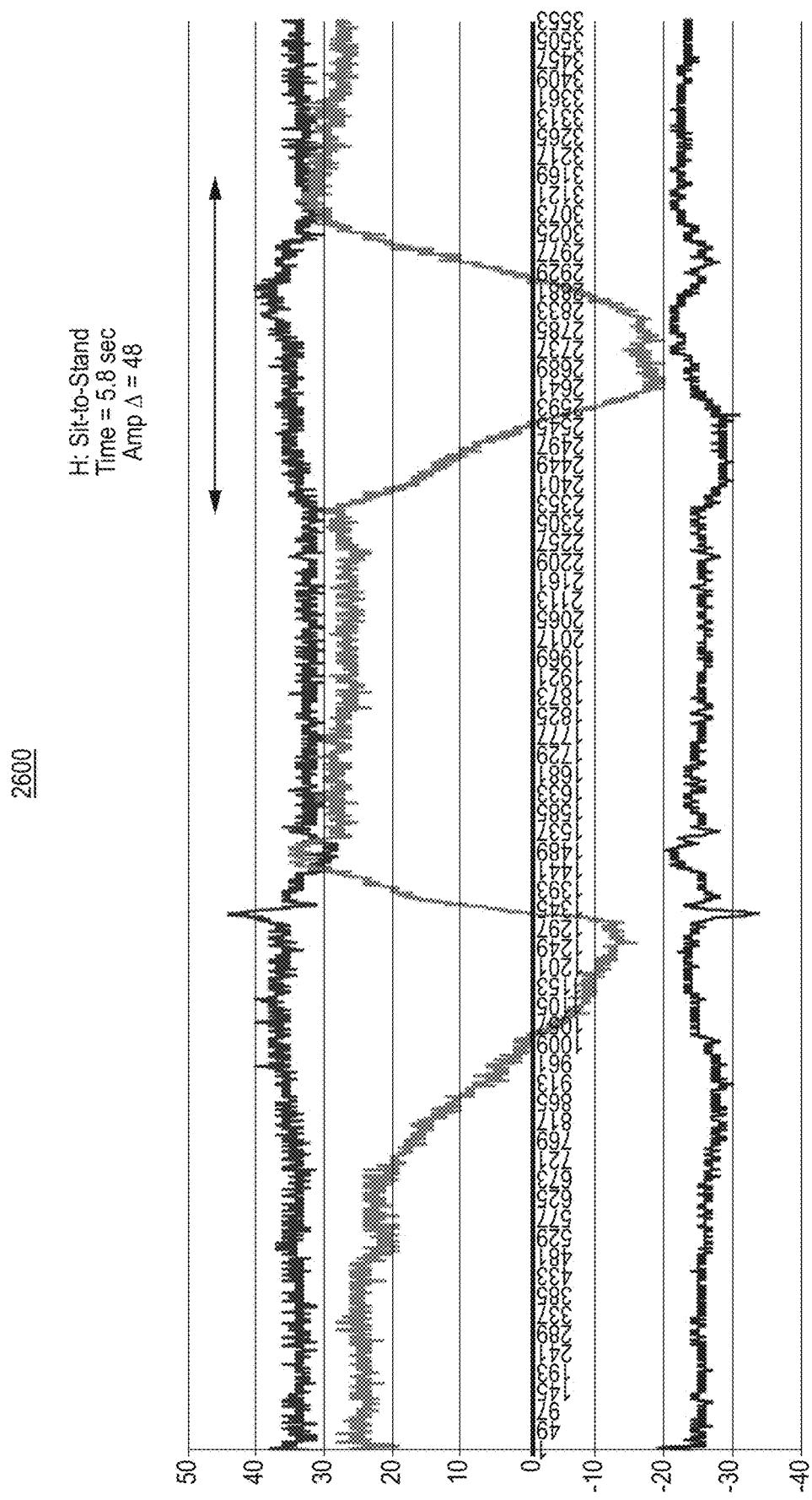
Figure 27:
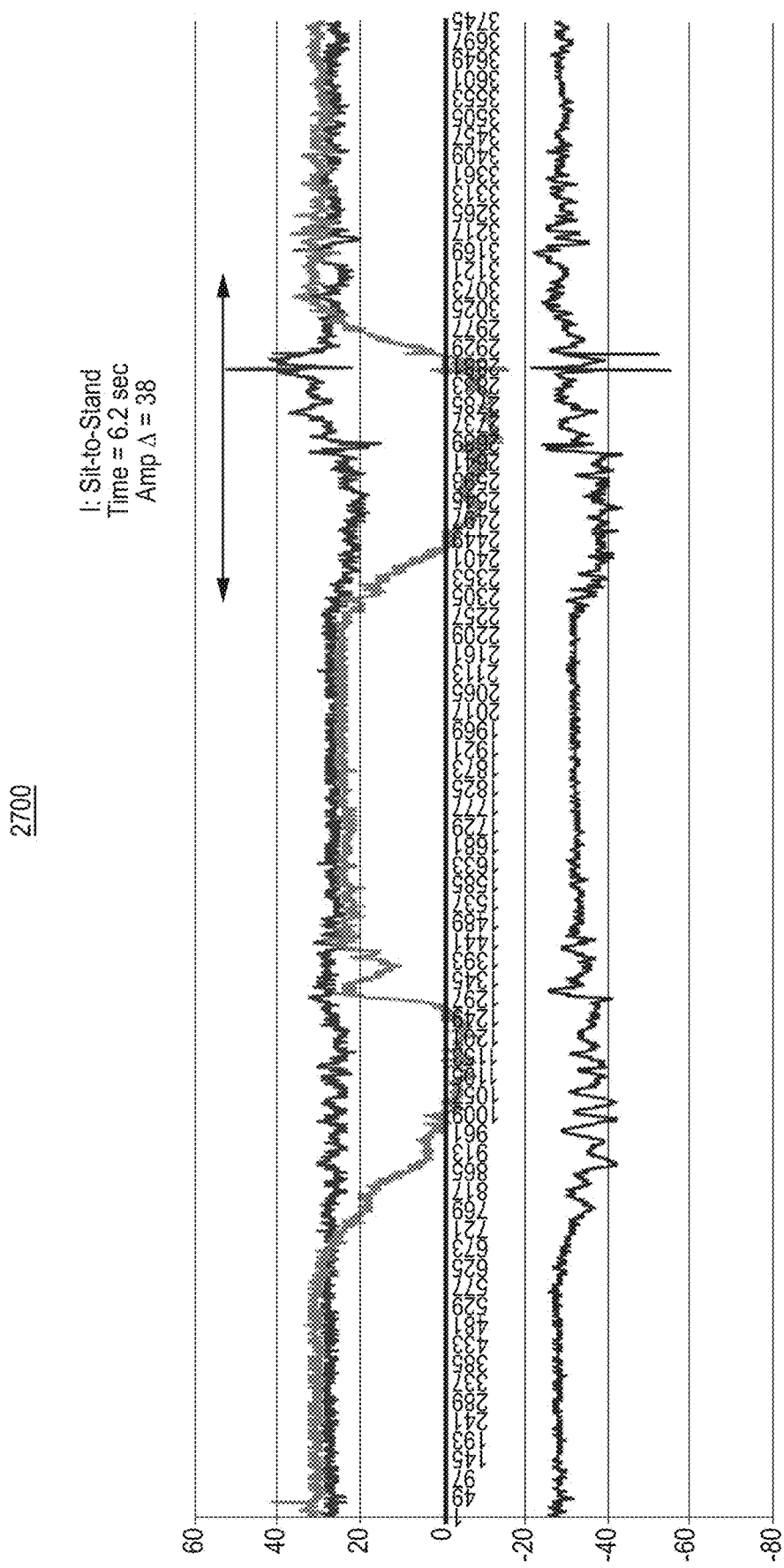
Figure 28:
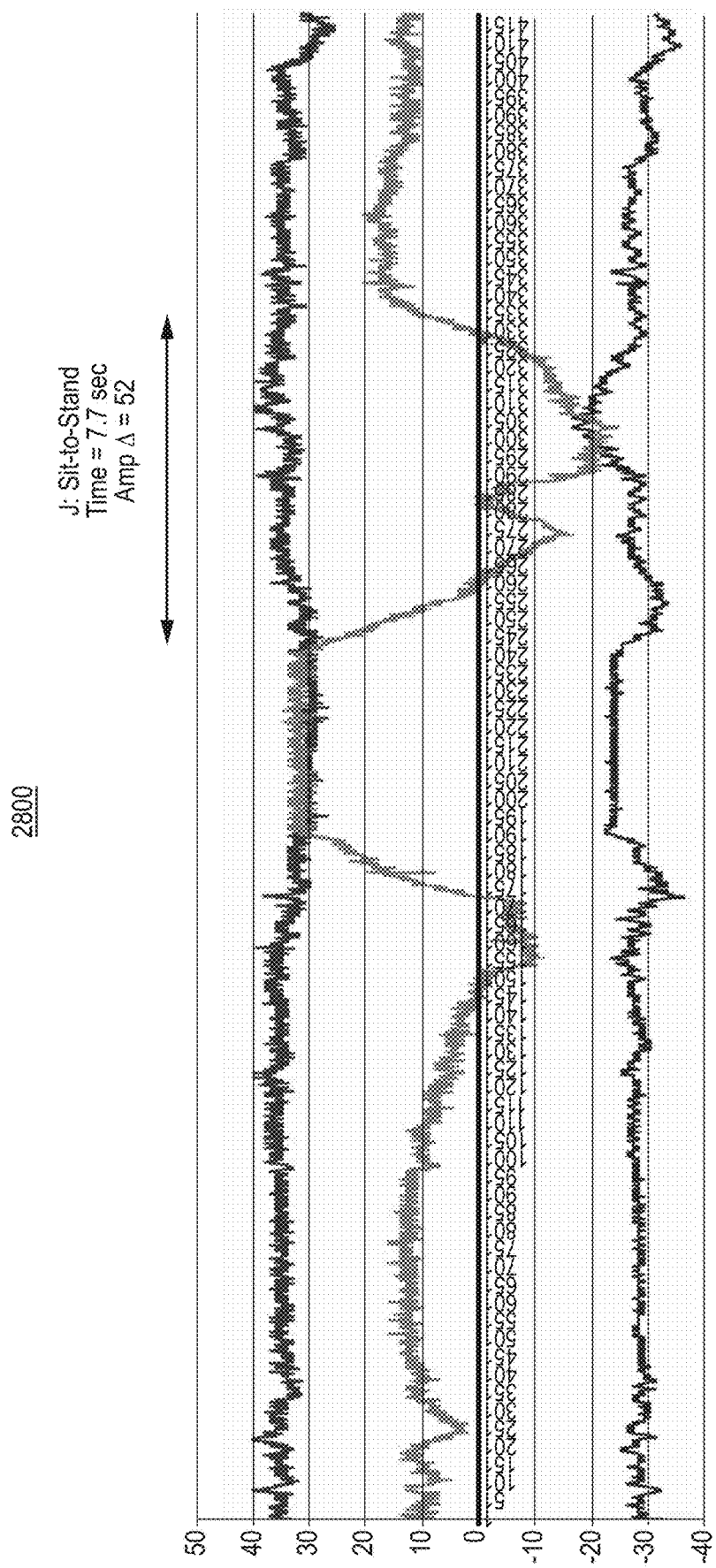

While the algorithm of FIG. 16 is directed to an analysis of the sagittal axis signal 1202 only to determine a Sit-To-Stand score, it is contemplated that one or both of the vertical axis signal 1204 and the transverse axis signal 1206 of FIG. 12 may be leveraged as well. For example, FIG. 17 is a plot 1700 illustrating first characteristics of the vertical axis signal 1204 of FIG. 12. FIG. 18 is a plot 1800 illustrating second characteristics of the vertical axis signal 1204 of FIG. 17. In practice, peak-valley information (equivalently, peak-peak information) and temporal interval information or determining patient functional status based on accelerometer-generated data in accordance with the disclosure.

With reference to FIGS. 17-18, an example algorithm may include:
  Identify valley (negative deflection) from baseline by:
    determining flat baseline (e.g., −1 g) for at least a certain number of second (e.g. 15 s) with a decrease of at least certain number of units (e.g. 0.2 g);
  Identify peak (positive deflection) following valley by:
    (if valley detected), checking for peak of similar amplitude from baseline within a certain time period (e.g. within 0.5 s-5 s);
  Determine standing up characteristics by:
    analyzing the vertical axis signal 1204 from start to end inclusive;
    determining vertical negative and positive deflections for boundary/range for confirming presence of a sit-to-stand segment from the sagittal axis signal; this may be beneficial since the stand-to-sit morphology can look similar; after the vertical axis signal confirms the sit-to-stand on the sagittal axis signal, then all the sagittal measurements can be made;
    calculating maximum absolute amplitude between the peak and valley;
    calculating time to stand from start to stop;
    calculating number of events;
    storing date/time of each stand up with the standing up characteristic;
    calculating daily min, max, median;
    calculating estimated 5× Sit to Stand Test (5×SST) score= [Daily median of time to stand+constant sit time (e.g. 1 sec)]×5; in some instance, assume time to sit is fairly constant due the work of gravity.

Referring now to FIGS. 19-28, each one is a plot of a series of plots 1900-2800 illustrating sagittal, vertical and transverse axis signals produced by an accelerometer during at least one sit-stand movement. The form or shape of the respective signals in each plot of a series of plots 1900-2800 are consistent with sagittal axis signal 1202, a vertical axis signal 1204 and transverse axis signal 1206 as shown in FIG. 12, and further demonstrate that the respective signals can be leveraged for measuring or determining patient functional status, as part of a SST performance test for example.

Figure 29:
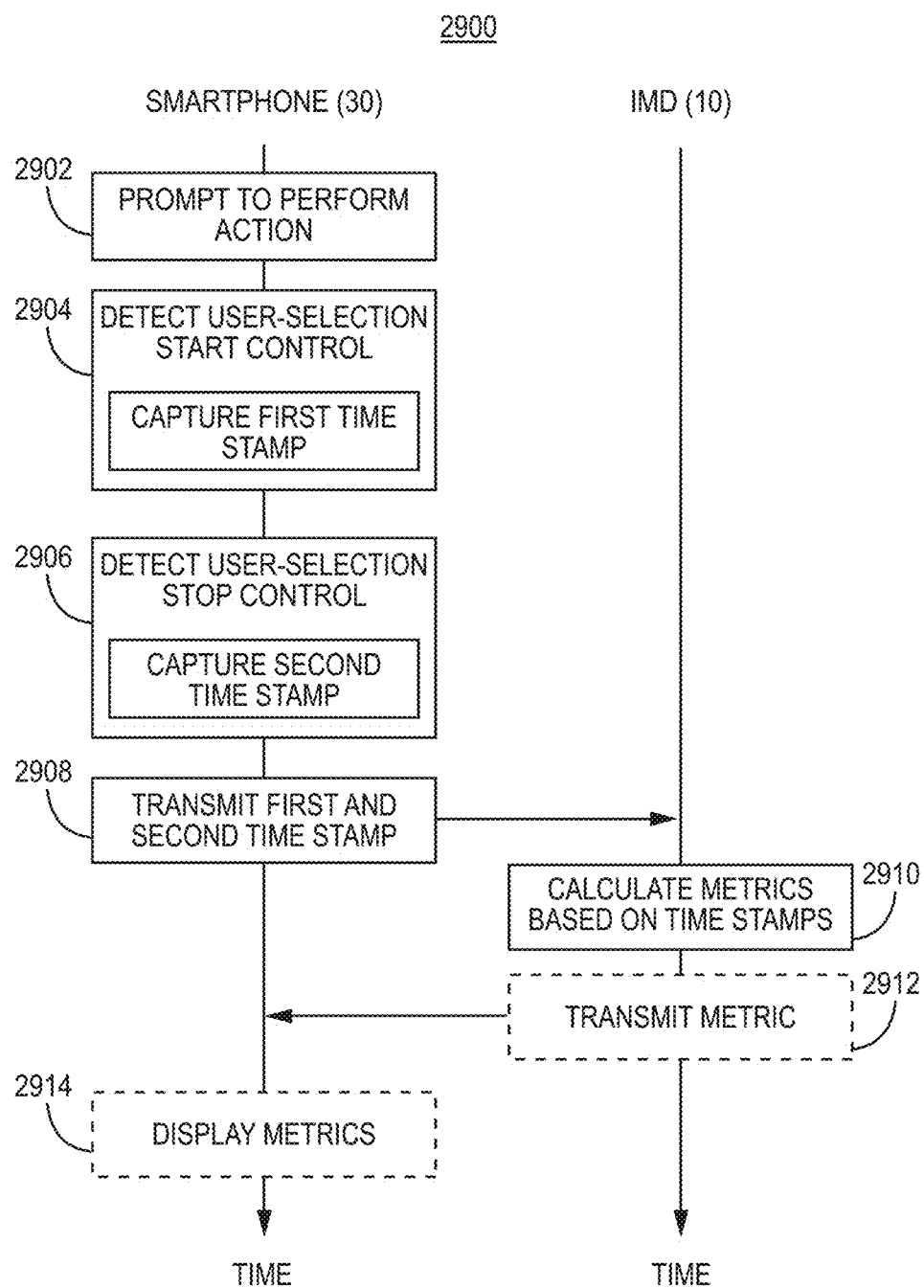
FIG. 29 is a flowchart illustrating a third example method for determining patient functional status based on accelerometer-generated data in accordance with the disclosure.
Figure 30:
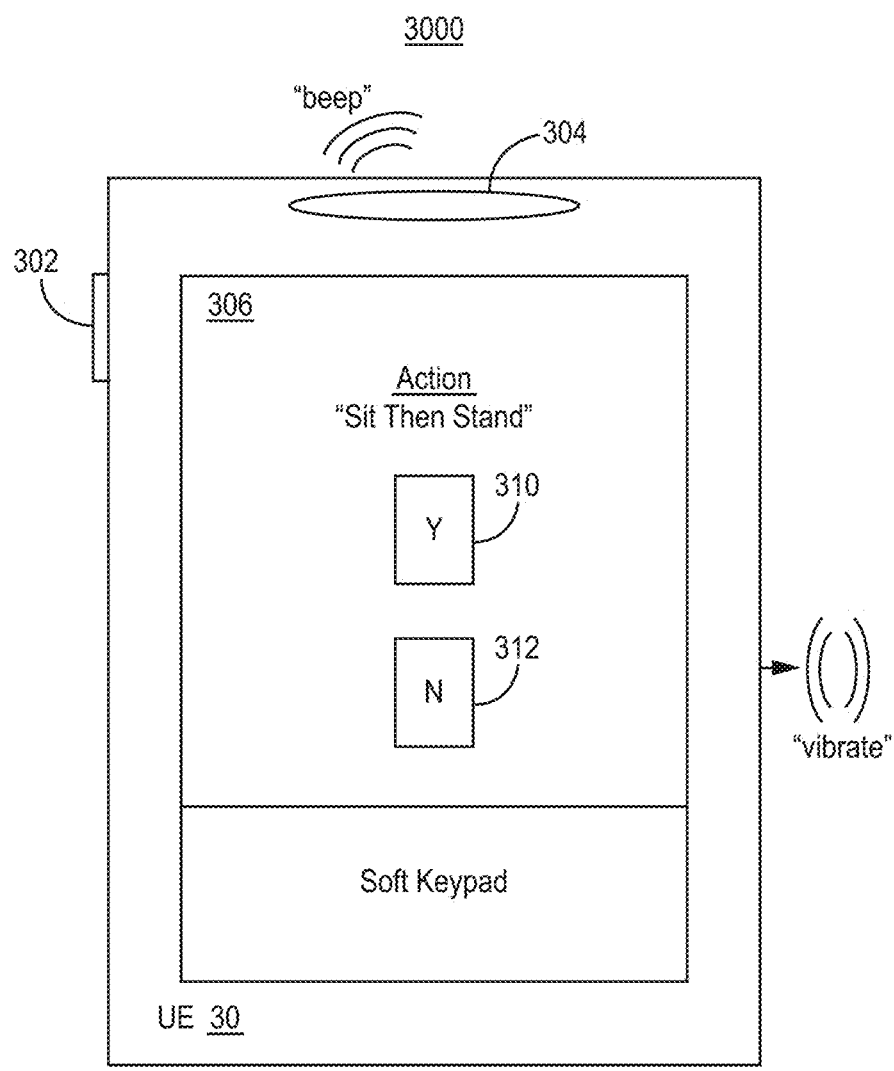
FIGS. 30-33 illustrate a sequence of graphical user interfaces for acquiring timestamps to mark a window for determining patient functional status based on accelerometer-generated data in accordance with the disclosure.
Figure 31:
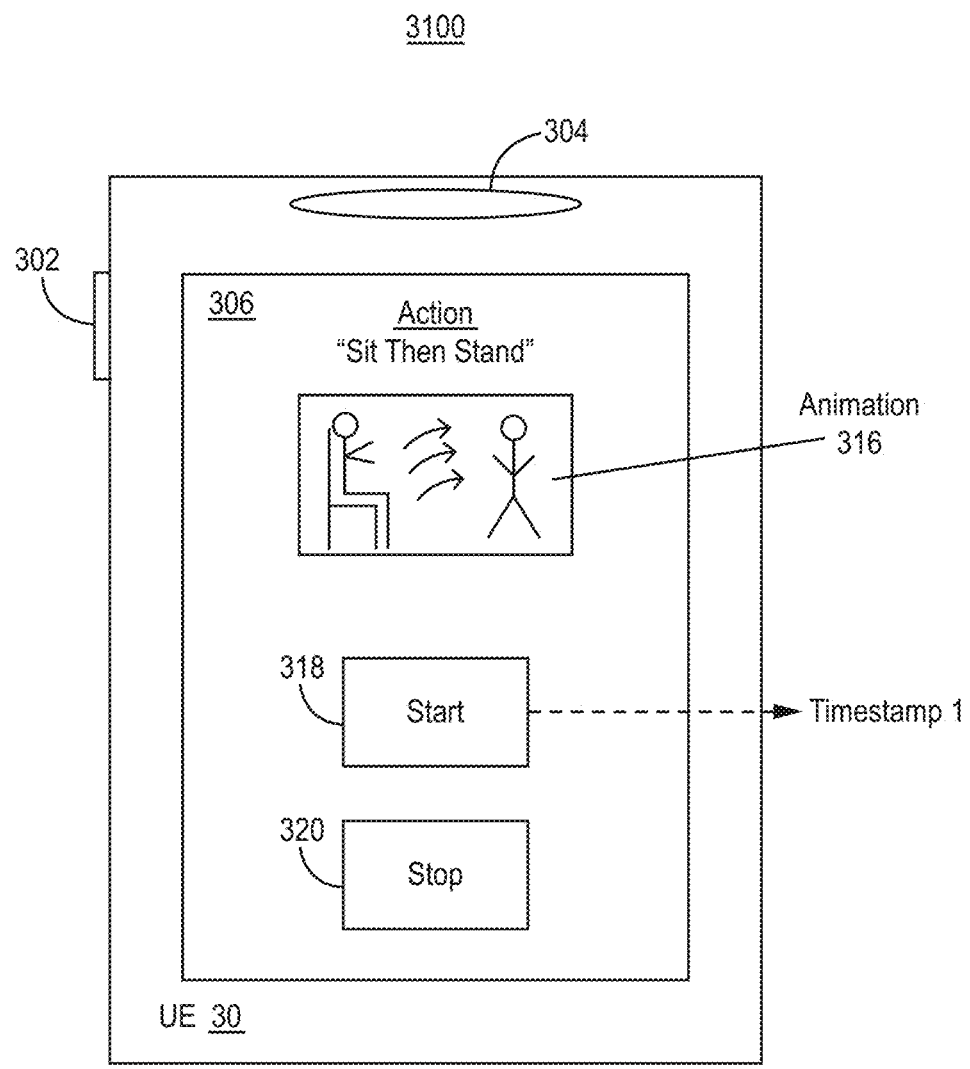
Figure 32:
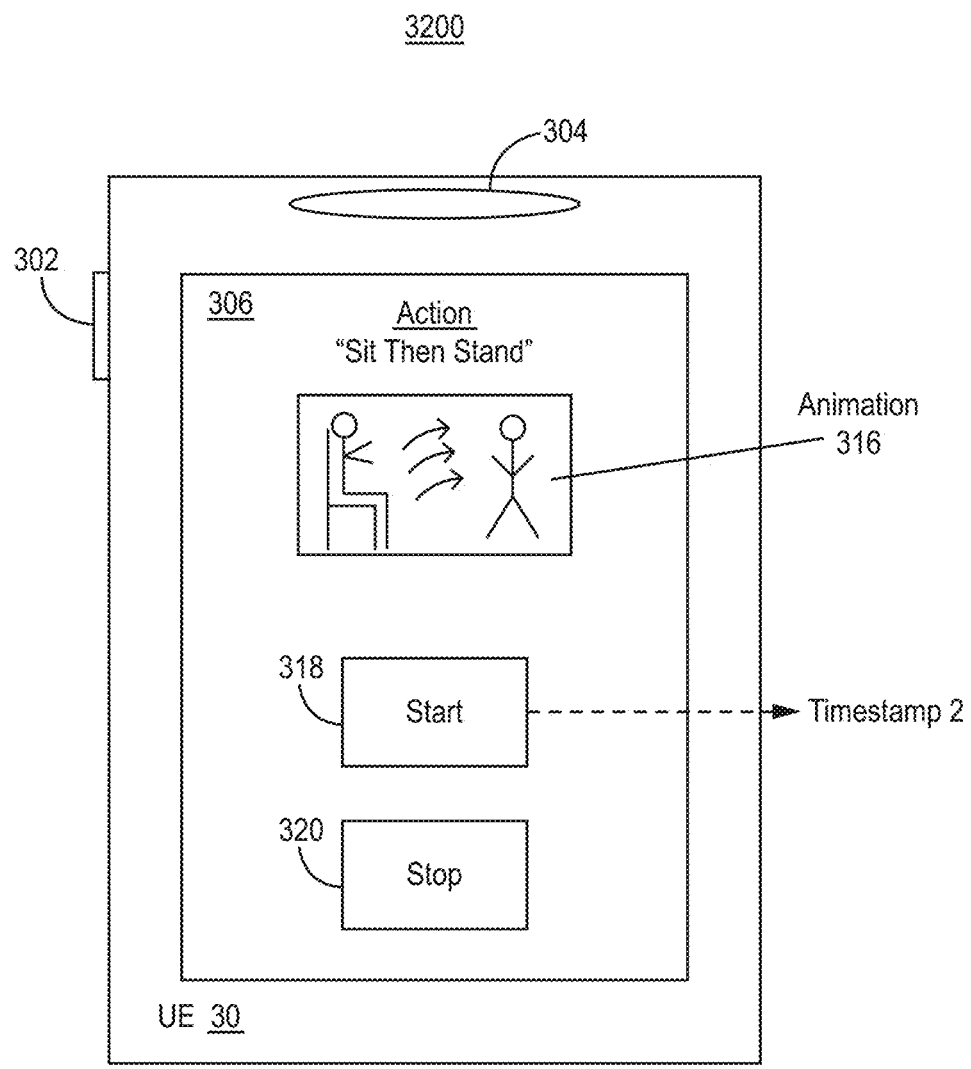

FIG. 29 is a flowchart illustrating a third example method 2900 for determining patient functional status based on accelerometer-generated data in accordance with the disclosure. Similar to method 1000, may be implemented by any one of the implantable medical devices discussed above in connection with FIGS. 1-9, because each one of the same is configured to include at least one accelerometer (i.e., accelerometer circuitry), as well as communication and processing circuitry (see FIG. 7 and corresponding description) to facilitate determining patient functional status based on accelerometer-generated data. Further, method 2900 may be implemented at least in part by any one of the external devices discussed above in connection with FIGS. 1-9, because each one of the same is configured to include a human-machine interface (e.g., touchscreen), as well as communication and processing circuitry (see FIG. 8 and corresponding description) to facilitate determining patient functional status based on accelerometer-generated data.

For example, and with reference to FIGS. 30-33 which illustrate a sequence of graphical user interfaces for acquiring timestamps to mark a window for determining patient functional status based on accelerometer-generated data in accordance with the disclosure, a smartphone 30 (FIG. 30) that comprises a pushbutton input 302, an audio output 304 and a touchscreen 306 may prompt (2902) an end-user (i.e., patient) to engage in a "Sit-To-Stand" test. In some examples, the prompt may include one or more of a visual, an audio and a tactile output or cue. For example, together with at least one of a "beep" and a preferentially-timed "vibrate" output by the smartphone 30, a graphic "Action: Sit-To-Stand" test in a first user interface (FIG. 30) may be output for display on the touchscreen 306. In this example, a control 310 and a control 312 may also be output for display, so that the end-user may "tap" to participate in (or not) the Sit-To-Stand test.

In response to a "tap" of the control 310, an animation 316 in a second user interface (FIGS. 31-32) may be output for display on the touchscreen 306, to guide the patient to perform an appropriate movement for the Sit-To-Stand test. In this example, a control 318 and a control 320 may also be output for display, so that the end-user may "tap" to start (or not) the Sit-To-Stand test. In response to a "tap" of the control 318, a first timestamp (FIG. 31) may be generated (2904) by the smartphone 300 to mark the beginning of the Sit-To-Stand test, and presumably the beginning of a "stand" movement as per the animation 316. Next, in response to a "tap" of the control 320, a second timestamp (FIG. 32) may be generated (2906) by the smartphone 300 to mark the end of the Sit-To-Stand test, and presumably the end of a "sit" movement as per the animation 316. In some examples, only a single control may be presented in the second user interface so that a patient could keep a finger above a same area of the touchscreen 306, and then perform a "tap" then "tap" action on the same area of the touchscreen 306, to simplify the process and provoke a more accurate timestamp generation procedure. In this example, the text "Start" on the control 318 may change to the text "Stop" following a first "tap". Other examples are possible.

Following acquisition of the first and second timestamp as described, corresponding data may be transmitted (2908) to the IMD 10 such that the IMD 10 may calculate (2910) a patient-specific functional status parameter associated with a Sit-To-Stand test from at least one of a sagittal axis signal, a vertical axis signal and a transverse axis signal over a time segment inclusively bounded by a first time defined by the first timestamp data and a second time defined by the second timestamp data, in a manner as discussed above. In some examples, the accelerometer(s) 166 is assumed to be powered-on and storing data associated with at least one of the sagittal axis signal, the vertical axis signal and the transverse axis signal throughout time, such as in a buffer memory of predetermined capacity (e.g., 10 minute rolling window). Accordingly, upon receipt of the first and second timestamp, the IMD 10 may access the buffer memory to access the proper time segment data to be used to calculate the patient-specific functional status parameter. In other examples, the smartphone 302 and the IMD 10 may transparently negotiate prior to the prompt (2902) mentioned above, and then the IMD 10 may power-on the accelerometer(s) 166 and/or or increase resolution of data acquired by the accelerometer(s) 166 over a forthcoming Sit-To-Stand test. Other examples are possible.

In some examples, data corresponding to the patient-specific functional status parameter may then be transmitted (2908) to the smartphone 302 such that a graphic "Your current score is 7 on a scale of 10" in a third user interface (FIG. 33) may be output for display on the touchscreen 306. Such an implementation may be beneficial and/or advantageous in many respects. For example, such an implementation may be used to identify changes in behavior and health, to get medical attention sooner rather than later and improving the chances of earlier recovery. Prompting an individual user will provide greater confidence that the user is performing the activity (with their unique sensor signal morphology) than a "one-size-fits-all" solution. It is contemplated that patient-specific morphology may also be used as a template to identify similar morphologies while continuously monitoring the accelerometer signal, to identify similar occurrences of sit-to-stand movements to then be analyzed with any or all of the disclosed metrics.

Figure 34:
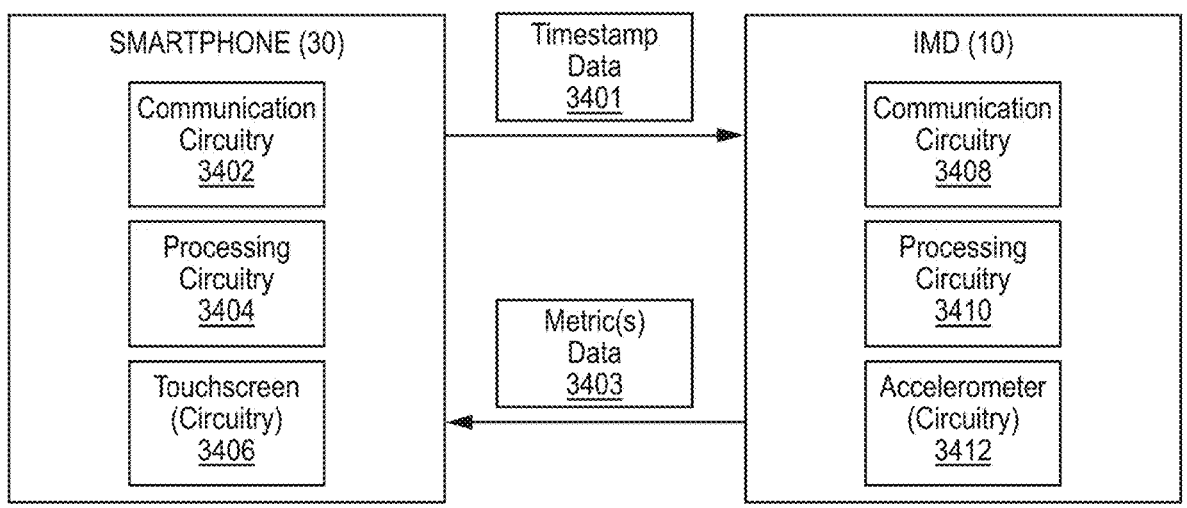
FIG. 34 is a functional block diagram illustrating an example communication sequence between an implantable medical device and an external device in accordance with the disclosure.

FIG. 34 is a functional block diagram 3400 illustrating an example communication sequence between the smartphone 30 (equivalently, "user equipment") and the IMD 10 of FIG. 29. Although not so limited, timestamp data 3401 may be transmitted from the smartphone 30 to the IMD 10, and at a subsequent time metric data 3403 may be transmitted to from the IMD 10 to the smartphone 30 in a manner as discussed above in connection with FIG. 29. As would be understood by one of skill in the art, the smartphone 30 may include communication circuitry 3402, processing circuitry 3404, and a touchscreen 3406. An example of such a smartphone includes as the iPhone® by Apple Inc. of Cupertino, Calif. Regarding the smartphone 30, additional details may be found in above discussion in connection with at least FIG. 8. The IMD 10 may include communication circuitry 3408, processing circuitry 3410, and at least one accelerometer 3412. Regarding the IMD 10, additional details may be found in above discussion in connection with at least FIG. 7, including details to the sensing circuitry 162, processing circuitry 160, accelerometers 167, etc.

A medical device or system, method, and non-transitory computer-readable storage medium comprising executable instructions, for determining patient-specific functional status from accelerometer data is contemplated throughout.

For example, an implantable medical device (IMD) for determining patient-specific functional status from accelerometer data may include or comprise communication circuitry configured to establish a communication link and transfer data between the IMD intra-corpus and a computing device extra-corpus. The IMD may further include or comprise accelerometer circuitry configured to generate a plurality of signals including a sagittal axis signal, a vertical axis signal and a transverse axis signal. An example of such an implementation is discussed above in connection with at least FIG. 9. The IMD may further include or comprise processing circuitry configured to: acquire first timestamp data and second timestamp data each one generated by the computing device and received by the IMD via the communication circuitry; calculate a patient-specific functional status parameter associated with a Sit-To-Stand test from at least one of the sagittal axis signal, the vertical axis signal and the transverse axis signal over a time segment inclusively bounded by a first time defined by the first timestamp data and a second time defined by the second timestamp data; and in response to a command, activate the communication circuitry to transmit the patient-specific functional status parameter from the IMD to the computing device. An example of such an implementation is discussed above in connection with and shown in at least FIGS. 10 and 29.

Additionally, or alternatively, the processing circuitry is configured to: calculate rate of change of a segment of at least one of the sagittal axis signal, the vertical axis signal and the transverse axis signal within the time segment; and calculate the patient-specific functional status parameter based on the calculated rate of change. An example of such an implementation is discussed above in connection with and shown in at least FIG. 14.

Additionally, or alternatively, the processing circuitry is configured to: calculate a definite integral over a segment of at least one of the sagittal axis signal, the vertical axis signal and the transverse axis signal within the time segment; and calculate the patient-specific functional status parameter based on the calculated definite integral. An example of such an implementation is discussed above in connection with and shown in at least FIG. 14.

Additionally, or alternatively, the processing circuitry is configured to: calculate a length of time of a segment of at least one of the sagittal axis signal, the vertical axis signal and the transverse axis signal within the time segment; and calculate the patient-specific functional status parameter based on the calculated length of time. An example of such an implementation is discussed above in connection with and shown in at least FIG. 16.

Additionally, or alternatively, the processing circuitry is configured to: calculate a peak amplitude of a segment of at least one of the sagittal axis signal, the vertical axis signal and the transverse axis signal within the time segment; and calculate the patient-specific functional status parameter based on the calculated peak amplitude. An example of such an implementation is discussed above in connection with and shown in at least FIG. 16.

Additionally, or alternatively, the processing circuitry is configured to: calculate a peak-peak amplitude of a segment of at least one of the sagittal axis signal, the vertical axis signal and the transverse axis signal within the time segment; and calculate the patient-specific functional status parameter based on the calculated peak-peak amplitude. An example of such an implementation is discussed above in connection with and shown in at least FIG. 17.

Additionally, or alternatively, the processing circuitry is configured to: calculate at least one baseline characteristic from the at least one of the sagittal axis signal, the vertical axis signal and the transverse axis signal, wherein the at least one baseline characteristic is associated with a movement-free sitting position posture; and calculate the patient-specific functional status parameter based on the at least one baseline characteristic. An example of such an implementation is discussed above in connection with and shown in at least FIG. 15.

Additionally, or alternatively, the processing circuitry is configured to: calculate the patient-specific functional status parameter from at least one characteristic of at least one of the sagittal axis signal, the vertical axis signal and the transverse axis signal over multiple distinct time intervals; calculate an averaged patient-specific functional status parameter from each interval-specific calculated patient-specific functional status parameter; and activate the communication circuitry to transmit the averaged patient-specific functional status parameter from the IMD to the computing device. An example of such an implementation is discussed above in connection with and shown in at least FIG. 16.

Additionally, or alternatively, the processing circuitry is configured to: calculate a time occurrence of at least one inflection point of at least one of the sagittal axis signal, the vertical axis signal and the transverse axis signal within the time segment; and calculate the patient-specific functional status parameter based on the calculated time occurrence. An example of such an implementation is discussed above in connection with and shown in at least FIG. 15 (i.e., time at which "peak" occurs Additionally, or alternatively, the processing circuitry is configured to: in response to an activation command, power-on the accelerometer circuitry to generate the plurality of signals including the sagittal axis signal, the vertical axis signal and the transverse axis signal. An example of such an implementation is discussed above in connection with and shown in at least FIG. 10.

Additionally, or alternatively, the processing circuitry is configured to: in response to a deactivation command, power-down the accelerometer circuitry for a predetermined period of time to conserve power of the IMD. An example of such an implementation is discussed above in connection with and shown in at least FIG. 10.

Additionally, or alternatively, the processing circuitry is configured to: calculate a symmetry characteristic metric from at least one segment of the at least one of the sagittal axis signal, the vertical axis signal and the transverse axis signal within the time segment, wherein the at least one segment is associated with a Sit-To-Stand or stand-to-sit movement of the Sit-To-Stand test; and calculate the patient-specific functional status parameter based on the calculated symmetry characteristic metric. An example of such an implementation is discussed above in connection with and shown in at least FIGS. 15-16.

Additionally, or alternatively, the processing circuitry is configured to: calculate a velocity metric from the at least one of the sagittal axis signal, the vertical axis signal and the transverse axis signal within the time segment to determine an average or instantaneous velocity associated with a Sit-To-Stand or stand-to-sit movement of the Sit-To-Stand test; and calculate the patient-specific functional status parameter based on the calculated velocity metric. An example of such an implementation is discussed above in connection with and shown in at least FIGS. 15-16.

Additionally, or alternatively, the processing circuitry is configured to: calculate a distance metric from the at least one of the sagittal axis signal, the vertical axis signal and the transverse axis signal within the time segment to determine a total or intermediate displacement associated with a Sit-To-Stand or stand-to-sit movement of the Sit-To-Stand test; and calculate the patient-specific functional status parameter based on the calculated distance metric. An example of such an implementation is discussed above in connection with and shown in at least FIGS. 15-16.

Additionally, or alternatively, the processing circuitry is configured to: calculate a kinetic energy metric from the at least one of the sagittal axis signal, the vertical axis signal and the transverse axis signal within the time segment to determine a total or intermediate energy expenditure associated with a Sit-To-Stand or stand-to-sit movement of the Sit-To-Stand test; and calculate the patient-specific functional status parameter based on the calculated kinetic energy metric. An example of such an implementation is discussed above in connection with and shown in at least FIGS. 15-16.

Additionally, or alternatively, the processing circuitry is configured to: calculate a potential energy metric from the at least one of the sagittal axis signal, the vertical axis signal and the transverse axis signal within the time segment and the distance metric to determine a total or intermediate increase or decrease in potential energy associated with a Sit-To-Stand or stand-to-sit movement of the Sit-To-Stand test; and calculate the patient-specific functional status parameter based on the calculated potential energy metric. An example of such an implementation is discussed above in connection with and shown in at least FIGS. 15-16.

Additionally, or alternatively, the processing circuitry is configured to: calculate a derivative metric from a segment of the at least one of the sagittal axis signal, the vertical axis signal and the transverse axis signal within the time segment to determine erratic movement associated with a Sit-To-Stand or stand-to-sit movement of the Sit-To-Stand test; and calculate the patient-specific functional status parameter based on the calculated derivative metric. An example of such an implementation is discussed above in connection with and shown in at least FIGS. 15-16.

Additionally, or alternatively, the processing circuitry is configured to: identify, from a template defined by the at least one of the sagittal axis signal, the vertical axis signal and the transverse axis signal over the time segment inclusively bounded by the first time defined by the first timestamp data and the second time defined by the second timestamp data, morphologies obtained or derived from one or more of the sagittal axis signal, the vertical axis signal and the transverse axis signal, over another time segment different than the time segment, that are similar to morphologies obtained or derived from the template, as an indication of at least one of a sit-to-stand movement and a stand-to-sit movement. An example of such an implementation is discussed above in connection with and shown in at least FIG. 12 and FIGS. 30-33.

As another example, a user equipment for determining patient-specific functional status from accelerometer data may include or comprise communication circuitry configured to establish a communication link and transfer data between the user equipment extra-corpus and an implantable medical device (IMD) intra-corpus. The user equipment may further include or comprise processing circuitry configured to: generate first timestamp data based upon detection of a first touch event on a touchscreen of the user equipment; generate second timestamp data based upon detection of a second touch event on the touchscreen; and in response to a command, activate the communication circuitry to transmit the patient-specific functional status parameter to the IMD for calculation of a patient-specific functional status parameter associated with a Sit-To-Stand performance test over a time segment inclusively bounded by a first time defined by the first timestamp data and a second time defined by the second timestamp data. An example of such an implementation is discussed above in connection with and shown in at least FIGS. 10 and 29.

Additionally, or alternatively, the processing circuitry is configured to: generate for rendering by the touchscreen time-static image data. An example of such an implementation is discussed above in connection with and shown in at least FIGS. 30-33.

Additionally, or alternatively, the processing circuitry is configured to: generate for rendering by the touchscreen time-dynamic image data. An example of such an implementation is discussed above in connection with and shown in at least FIGS. 30-33.

Additionally, or alternatively, the processing circuitry is configured to: generate for rendering by the touchscreen data for buttons or icons for initiating mobile application-specific actions. An example of such an implementation is discussed above in connection with and shown in at least FIGS. 30-33.

Additionally, or alternatively, the processing circuitry is configured to: generate for rendering by the touchscreen animation data that represents an action to be performed by a user of the user equipment. An example of such an implementation is discussed above in connection with and shown in at least FIGS. 30-33.

Additionally, or alternatively, the processing circuitry is configured to: access data, received from the medical device system via the communication circuitry, that represents the patient-specific functional status parameter associated with the Sit-To-Stand performance test; generate, from the received data and for rendering by the touchscreen, data that represents the patient-specific functional status parameter. An example of such an implementation is discussed above in connection with and shown in at least FIGS. 30-33.

Additionally, or alternatively, the processing circuitry is configured to: access a mobile application software installed to the user equipment to generate interface object data for rendering by the touchscreen objects for initiating actions both specific and non-specific to the mobile application software; and generate, for rendering by the touchscreen, interface objects for initiating actions both specific and non-specific to the mobile application software. An example of such an implementation is discussed above in connection with and shown in at least FIGS. 30-33.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

EXEMPLARY EMBODIMENTS

Embodiment 1 is a medical device system comprising:
accelerometer circuitry configured to generate a plurality of signals including a sagittal axis signal, a vertical axis signal and a transverse axis signal; and
processing circuitry configured to:
calculate a patient-specific functional status parameter associated with a Sit-To-Stand test from at least one of the sagittal axis signal, the vertical axis signal and the transverse axis signal over a time segment inclusively bounded by a first and second time each generated by a user equipment and received by the system as timestamp data from the user equipment over a communication link.

Embodiment 2 is a method comprising:
generating, by a medical device system, a plurality of signals including a sagittal axis signal, a vertical axis signal and a transverse axis signal; and
calculating, by the medical device system, a patient-specific functional status parameter associated with a Sit-To-Stand test from at least one of the sagittal axis signal, the vertical axis signal and the transverse axis signal over a time segment inclusively bounded by a first and second time each generated by a user equipment and received by the system as timestamp data from the user equipment over a communication link.

Embodiment 3 is a medical device system comprising means for performing the method of embodiment 2.

Embodiment 4 is a non-transitory computer-readable storage medium comprising instructions, that when executed by processing circuitry of a medical device system, cause the medical device system to perform the method of embodiment 2.

Embodiment 5 is a medical device system, method, and non-transitory computer-readable storage medium comprising executable instructions, for determining patient-specific functional status from accelerometer data based on timestamp data generated by a user equipment as described in the specification and/or shown in any of the drawings.

Embodiment 6 is a user equipment comprising:
a touchscreen; and
at least one processor configured to:
generate first timestamp data based upon detection of a first touch event on the touchscreen, and second timestamp data based upon detection of a second touch event on the touchscreen, for calculation by a medical device system of a patient-specific functional status parameter associated with a Sit-To-Stand performance test over a time segment inclusively bounded by a first time defined by the first timestamp data and a second time defined by the second timestamp data.

Embodiment 7 is a method comprising:
by a user equipment,
generating first timestamp data based upon detection of a first touch event on a touchscreen of the user equipment, and second timestamp data based upon detection of a second touch event on the touchscreen, for calculation by a medical device system of a patient-specific functional status parameter associated with a Sit-To-Stand performance test over a time segment inclusively bounded by a first time defined by the first timestamp data and a second time defined by the second timestamp data.

Embodiment 8 is a user equipment comprising means for performing the method of embodiment 7.

Embodiment 9 is a non-transitory computer-readable storage medium comprising instructions, that when executed by processing circuitry of a user equipment, cause the user equipment to perform the method of embodiment 7.

Embodiment 10 is a user equipment, method, and non-transitory computer-readable storage medium comprising executable instructions, for generating timestamp data for calculation of a patient-specific functional status parameter as described in the specification and/or shown in any of the drawings.

Embodiment 11 is a user equipment comprising:
communication circuitry configured to establish a communication link and transfer data between the user equipment extra-corpus and an implantable medical device (IMD) intra-corpus; and
processing circuitry configured to:
generate first timestamp data based upon detection of a first touch event on a touchscreen of the user equipment;
generate second timestamp data based upon detection of a second touch event on the touchscreen; and
in response to a command, activate the communication circuitry to transmit the patient-specific functional status parameter to the IMD for calculation of a patient-specific functional status parameter associated with a Sit-To-Stand performance test over a time segment inclusively bounded by a first time defined by the first timestamp data and a second time defined by the second timestamp data.

Embodiment 12 is the user equipment of embodiment 11, wherein the processing circuitry is configured to:
generate for rendering by the touchscreen time-static image data.

Embodiment 13 is the user equipment of any of embodiments 11 to 12, wherein the processing circuitry is configured to:
generate for rendering by the touchscreen time-dynamic image data.

Embodiment 14 is the user equipment of any of embodiments 11 to 13, wherein the processing circuitry is configured to:
generate for rendering by the touchscreen data for buttons or icons for initiating mobile application-specific actions.

Embodiment 15 is the user equipment of any of embodiments 11 to 14, wherein the processing circuitry is configured to:
generate for rendering by the touchscreen animation data that represents an action to be performed by a user of the user equipment.

Embodiment 16 is the user equipment of any of embodiment 11 to 15, wherein the processing circuitry is configured to:
access data, received from the medical device system via the communication circuitry, that represents the patient-specific functional status parameter associated with the Sit-To-Stand performance test;
generate, from the received data and for rendering by the touchscreen, data that represents the patient-specific functional status parameter.

Embodiment 17 is the user equipment of any of claims 11 to 16, wherein the processing circuitry is configured to:

access a mobile application software installed to the user equipment to generate interface object data for rendering by the touchscreen objects for initiating actions both specific and non-specific to the mobile application software; and generate, for rendering by the touchscreen, interface objects for initiating actions both specific and non-specific to the mobile application software.

Embodiment 18 is a method comprising:
by a user equipment,
generating first timestamp data based upon detection of a first touch event on a touchscreen of the user equipment;
generating second timestamp data based upon detection of a second touch event on the touchscreen; and
in response to a command, transmitting the patient-specific functional status parameter to an implantable medical device (IMD) for calculation of a patient-specific functional status parameter associated with a Sit-To-Stand performance test over a time segment inclusively bounded by a first time defined by the first timestamp data and a second time defined by the second timestamp data.

Embodiment 19 is the method of embodiment 18, further comprising:
generating time-static image data for rendering by the touchscreen.

Embodiment 20 is the method of any of embodiments 18 to 19, further comprising:
generating time-dynamic image data for rendering by the touchscreen.

Embodiment 21 is the method of any of embodiments 18 to 20, further comprising:
generating data for buttons or icons for rendering by the touchscreen and for initiating mobile application-specific actions.

Embodiment 22 is the method of any of embodiments 18 to 21, further comprising:
generating for rendering by the touchscreen animation data that represents an action to be performed by a user of the user equipment.

Embodiment 23 is the method of any of embodiments 18 to 22, further comprising:
receiving data from the medical device system that represents the patient-specific functional status parameter associated with the Sit-To-Stand performance test;
generating, from the received data and for rendering by the touchscreen, data that represents the patient-specific functional status parameter.

Embodiment 24 is the method of any of embodiments 18 to 23, further comprising:
accessing a mobile application software installed to the user equipment to generate interface object data for rendering by the touchscreen objects for initiating actions both specific and non-specific to the mobile application software; and
generating, for rendering by the touchscreen, objects for initiating actions both specific and non-specific to the mobile application software.

Embodiment 25 is a user equipment comprising means for performing any of the methods of embodiments 18 to 24.

Embodiment 26 is a non-transitory computer-readable storage medium comprising instructions, that when executed by processing circuitry of a user equipment, cause the user equipment system to perform any of the methods of embodiments 18-26.

Embodiment 27 is the device of any of embodiments 1 to 6, wherein the processing circuitry is configured to:

identify, from a template defined by the at least one of the sagittal axis signal, the vertical axis signal and the transverse axis signal over the time segment inclusively bounded by the first time defined by the first timestamp data and the second time defined by the second timestamp data, morphologies obtained or derived from one or more of the sagittal axis signal, the vertical axis signal and the transverse axis signal, over another time segment different than the time segment, that are similar to morphologies obtained or derived from the template, as an indication of at least one of a sit-to-stand movement and a stand-to-sit movement.

Embodiment 28 is the method of any of embodiments 18 to 24, further comprising:
identifying, from a template defined by the at least one of the sagittal axis signal, the vertical axis signal and the transverse axis signal over the time segment inclusively bounded by the first time defined by the first timestamp data and the second time defined by the second timestamp data, morphologies obtained or derived from one or more of the sagittal axis signal, the vertical axis signal and the transverse axis signal, over another time segment different than the time segment, that are similar to morphologies obtained or derived from the template, as an indication of at least one of a sit-to-stand movement and a stand-to-sit movement.

Embodiment 29 is an implantable medical device comprising means for performing any of the methods of embodiments 18 to 24.

Embodiment 30 is a non-transitory computer-readable storage medium comprising instructions, that when executed by processing circuitry of an implantable medical device, cause the implantable medical device to perform any of the methods of embodiments 18 to 24.

Embodiment 31 is a method comprising:
by an implantable medical device, intra-corpus,
generating a plurality of signals including a sagittal axis signal, a vertical axis signal and a transverse axis signal;
receiving, from a computing device extra-corpus, first timestamp data and second timestamp data each one generated by the computing device and received by the implantable medical device over a communication link;
calculating a patient-specific functional status parameter associated with a Sit-To-Stand test from at least one of the sagittal axis signal, the vertical axis signal and the transverse axis signal over a time segment inclusively bounded by a first time defined by the first timestamp data and a second time defined by the second timestamp data; and
in response to a command, transmitting the patient-specific functional status parameter to the computing device.

Embodiment 32 is the method of embodiment 31, further comprising:
calculating a length of time of a segment of at least one of the sagittal axis signal, the vertical axis signal and the transverse axis signal within the time segment; and
calculating the patient-specific functional status parameter based on the calculated length of time.

Embodiment 33 is the method of any of embodiments 31 to 32, further comprising:
calculating a peak amplitude of a segment of at least one of the sagittal axis signal, the vertical axis signal and the transverse axis signal within the time segment; and
calculating the patient-specific functional status parameter based on the calculated peak amplitude.

Embodiment 34 is the method of any of embodiments 31 to 33, further comprising:

calculating a peak-peak amplitude of a segment of at least one of the sagittal axis signal, the vertical axis signal and the transverse axis signal within the time segment; and calculating the patient-specific functional status parameter based on the calculated peak-peak amplitude.

Embodiment 35 is the method of any of embodiments 31 to 34, further comprising:

calculating at least one baseline characteristic from the at least one of the sagittal axis signal, the vertical axis signal and the transverse axis signal, wherein the at least one baseline characteristic is associated with a movement-free sitting position posture; and calculating the patient-specific functional status parameter based on the at least one baseline characteristic.

Embodiment 36 is the method of any of embodiments 31 to 35, further comprising:

calculating the patient-specific functional status parameter from at least one characteristic of at least one of the sagittal axis signal, the vertical axis signal and the transverse axis signal over multiple distinct time intervals;

calculating an averaged patient-specific functional status parameter from each interval-specific calculated patient-specific functional status parameter; and transmitting the averaged patient-specific functional status parameter to the computing device.

Embodiment 37 is the method of any of embodiments 31 to 36, further comprising:

calculating a time occurrence of at least one inflection point of at least one of the sagittal axis signal, the vertical axis signal and the transverse axis signal within the time segment; and calculating the patient-specific functional status parameter based on the calculated time occurrence.

Embodiment 38 is the method of any of embodiments 31 to 37, further comprising:

in response to an activation command, powering-on accelerometer circuitry of the implantable medical device to generate the plurality of signals including the sagittal axis signal, the vertical axis signal and the transverse axis signal.

Embodiment 39 is the method of any of embodiments 31 to 38, further comprising:

in response to a deactivation command, powering-down accelerometer circuitry of the implantable medical device for a predetermined period of time to conserve power of the implantable medical device.

Embodiment 40 is the method of embodiment 31, further comprising:

calculating a symmetry characteristic metric from at least one segment of the at least one of the sagittal axis signal, the vertical axis signal and the transverse axis signal within the time segment, wherein the at least one segment is associated with a Sit-To-Stand or stand-to-sit movement of the Sit-To-Stand test; and calculating the patient-specific functional status parameter based on the calculated symmetry characteristic metric.

Embodiment 41 is the method of embodiment 31, further comprising:

calculating a velocity metric from the at least one of the sagittal axis signal, the vertical axis signal and the transverse axis signal within the time segment to determine an average or instantaneous velocity associated with a Sit-To-Stand or stand-to-sit movement of the Sit-To-Stand test; and calculating the patient-specific functional status parameter based on the calculated velocity metric.

Embodiment 42 is the method of any of embodiments 40 to 41, further comprising:

calculating a distance metric from the at least one of the sagittal axis signal, the vertical axis signal and the transverse axis signal within the time segment to determine a total or intermediate displacement associated with a Sit-To-Stand or stand-to-sit movement of the Sit-To-Stand test; and calculating the patient-specific functional status parameter based on the calculated distance metric.

Embodiment 43 is the method of any of embodiments 40 to 42, further comprising:

calculating a kinetic energy metric from the at least one of the sagittal axis signal, the vertical axis signal and the transverse axis signal within the time segment to determine a total or intermediate energy expenditure associated with a Sit-To-Stand or stand-to-sit movement of the Sit-To-Stand test; and calculating the patient-specific functional status parameter based on the calculated kinetic energy metric.

Embodiment 44 is the method of any of embodiments 40 to 43, further comprising:

calculating a potential energy metric from the at least one of the sagittal axis signal, the vertical axis signal and the transverse axis signal within the time segment and the distance metric to determine a total or intermediate increase or decrease in potential energy associated with a Sit-To-Stand or stand-to-sit movement of the Sit-To-Stand test; and calculating the patient-specific functional status parameter based on the calculated potential energy metric.

Embodiment 45 is the method of any of embodiments 40 to 44, further comprising:

calculating a derivative metric from a segment of the at least one of the sagittal axis signal, the vertical axis signal and the transverse axis signal within the time segment and the distance metric to determine erratic movement associated with a Sit-To-Stand or stand-to-sit movement of the Sit-To-Stand test; and calculating the patient-specific functional status parameter based on the calculated derivative metric.

Various aspects of the disclosure have been described. These and other aspects are within the scope of the following claims.

What is claimed is:

1. A system comprising:
   an implantable medical device (IMD) comprising:
      communication circuitry configured to establish a communication link and transfer data between the IMD intra-corpus and a computing device extra-corpus; and
      accelerometer circuitry configured to generate a plurality of signals including a sagittal axis signal, a vertical axis signal and a transverse axis signal; and
   processing circuitry configured to:
      output, for display by the computing device, a first prompt for a user to indicate a start of a Sit-To-Stand test;
      output, for display by the computing device, a second prompt for the user to indicate a completion of the Sit-To-Stand test;
      receive first timestamp data and second timestamp data each one generated by the computing device based on user input;
      calculate a patient-specific functional status parameter associated with a Sit-To-Stand test from at least one of the sagittal axis signal, the vertical axis signal and the transverse axis signal over a time segment inclusively bounded by a first time defined by the first timestamp data and a second time defined by the second timestamp data, wherein the first timestamp data is generated by the computing device based on a user input indicating the start of the Sit-To-Stand test, and wherein the second timestamp data is generated by the computing device based on a user input indicating the completion of the Sit-to-Stand test; and in response to a command, activate the communication circuitry to transmit the patient-specific functional status parameter from the IMD to the computing device.

2. The system of claim 1, wherein the processing circuitry is configured to:

calculate rate of change of a segment of at least one of the sagittal axis signal, the vertical axis signal and the transverse axis signal within the time segment; and calculate the patient-specific functional status parameter based on the calculated rate of change.

3. The system of claim 1, wherein the processing circuitry is configured to:

calculate a definite integral over a segment of at least one of the sagittal axis signal, the vertical axis signal and the transverse axis signal within the time segment; and calculate the patient-specific functional status parameter based on the calculated definite integral.

4. The system of claim 1, wherein the processing circuitry is configured to:

calculate a length of time of a segment of at least one of the sagittal axis signal, the vertical axis signal and the transverse axis signal within the time segment; and calculate the patient-specific functional status parameter based on the calculated length of time.

5. The system of claim 1, wherein the processing circuitry is configured to:

calculate a peak amplitude of a segment of at least one of the sagittal axis signal, the vertical axis signal and the transverse axis signal within the time segment; and calculate the patient-specific functional status parameter based on the calculated peak amplitude.

6. The system of claim 1, wherein the processing circuitry is configured to:

calculate a peak-peak amplitude of a segment of at least one of the sagittal axis signal, the vertical axis signal and the transverse axis signal within the time segment; and calculate the patient-specific functional status parameter based on the calculated peak-peak amplitude.

7. The system of claim 1, wherein the processing circuitry is configured to:

calculate at least one baseline characteristic from the at least one of the sagittal axis signal, the vertical axis signal and the transverse axis signal, wherein the at least one baseline characteristic is associated with a movement-free sitting position posture; and calculate the patient-specific functional status parameter based on the at least one baseline characteristic.

8. The system of claim 1, wherein the processing circuitry is configured to:

calculate the patient-specific functional status parameter from at least one characteristic of at least one of the sagittal axis signal, the vertical axis signal and the transverse axis signal over multiple distinct time intervals;

calculate an averaged patient-specific functional status parameter from each interval-specific calculated patient-specific functional status parameter; and activate the communication circuitry to transmit the averaged patient-specific functional status parameter from the IMD to the computing device.

9. The system of claim 1, wherein the processing circuitry is configured to:

calculate a time occurrence of at least one inflection point of at least one of the sagittal axis signal, the vertical axis signal and the transverse axis signal within the time segment; and calculate the patient-specific functional status parameter based on the calculated time occurrence.

10. The system of claim 1, wherein the processing circuitry is configured to:

in response to an activation command, power-on the accelerometer circuitry to generate the plurality of signals including the sagittal axis signal, the vertical axis signal and the transverse axis signal.

11. The system of claim 1, wherein the processing circuitry is configured to:

in response to a deactivation command, power-down the accelerometer circuitry for a predetermined period of time to conserve power of the IMD.

12. The system of claim 1, wherein the processing circuitry is configured to:

calculate a symmetry characteristic metric from at least one segment of the at least one of the sagittal axis signal, the vertical axis signal and the transverse axis signal within the time segment, wherein the at least one segment is associated with a Sit-To-Stand or stand-to-sit movement of the Sit-To-Stand test; and calculate the patient-specific functional status parameter based on the calculated symmetry characteristic metric.

13. The system of claim 12, wherein the processing circuitry is configured to:

calculate a velocity metric from the at least one of the sagittal axis signal, the vertical axis signal and the transverse axis signal within the time segment to determine an average or instantaneous velocity associated with a Sit-To-Stand or stand-to-sit movement of the Sit-To-Stand test; and calculate the patient-specific functional status parameter based on the calculated velocity metric.

14. The system of claim 12, wherein the processing circuitry is configured to:

calculate a distance metric from the at least one of the sagittal axis signal, the vertical axis signal and the transverse axis signal within the time segment to determine a total or intermediate displacement associated with a Sit-To-Stand or stand-to-sit movement of the Sit-To-Stand test; and calculate the patient-specific functional status parameter based on the calculated distance metric.

15. The system of claim 12, wherein the processing circuitry is configured to:

calculate a kinetic energy metric from the at least one of the sagittal axis signal, the vertical axis signal and the transverse axis signal within the time segment to determine a total or intermediate energy expenditure associated with a Sit-To-Stand or stand-to-sit movement of the Sit-To-Stand test; and calculate the patient-specific functional status parameter based on the calculated kinetic energy metric.

16. The system of claim 15, wherein the processing circuitry is configured to:

calculate a potential energy metric from the at least one of the sagittal axis signal, the vertical axis signal and the transverse axis signal within the time segment and the distance metric to determine a total or intermediate increase or decrease in potential energy associated with a Sit-To-Stand or stand-to-sit movement of the Sit-To-Stand test; and calculate the patient-specific functional status parameter based on the calculated potential energy metric.

17. The system of claim 12, wherein the processing circuitry is configured to:

calculate a derivative metric from a segment of the at least one of the sagittal axis signal, the vertical axis signal and the transverse axis signal within the time segment to determine erratic movement associated with a Sit-To-Stand or stand-to-sit movement of the Sit-To-Stand test; and calculate the patient-specific functional status parameter based on the calculated derivative metric.

18. A method comprising:

establishing, by communication circuitry of an implantable medical device (IMD), a communication link and transfer data between the IMD intra-corpus and a computing device extra-corpus;

generating, by accelerometer circuitry of the IMD, a plurality of signals including a sagittal axis signal, a vertical axis signal and a transverse axis signal;

receiving, by processing circuitry from the computing device, first timestamp data and second timestamp data each one generated by the computing device based on user input;

calculating, by the processing circuitry, a patient-specific functional status parameter associated with a Sit-To-Stand test from at least one of the sagittal axis signal, the vertical axis signal and the transverse axis signal over a time segment inclusively bounded by a first time defined by the first timestamp data and a second time defined by the second timestamp data, wherein the first timestamp data is generated by the computing device based on a user input indicating the start of the Sit-To-Stand test, and wherein the second timestamp data is generated by the computing device based on a user input indicating the completion of the Sit-to-Stand test; and in response to a command, transmitting, by the processing circuitry, the patient-specific functional status parameter to the computing device.

19. The method of claim 18, further comprising:

calculating, by the processing circuitry, a rate of change of a segment of at least one of the sagittal axis signal, the vertical axis signal and the transverse axis signal within the time segment; and calculating, by the processing circuitry, the patient-specific functional status parameter based on the calculated rate of change.

20. The method of claim 18, further comprising:

calculating, by the processing circuitry, a definite integral over a segment of at least one of the sagittal axis signal, the vertical axis signal and the transverse axis signal within the time segment; and calculating, by the processing circuitry, the patient-specific functional status parameter based on the calculated definite integral.

* * * * *